United States Patent [19]
Buchsbaum et al.

[11] Patent Number: 6,001,329
[45] Date of Patent: Dec. 14, 1999

[54] RADIOLABELED FUSION TOXINS FOR CANCER THERAPY

[75] Inventors: Donald J. Buchsbaum, Birmingham, Ala.; Bruce R. Blazar, Golden Valley; Daniel A. Vallera, St. Louis Park, both of Minn.

[73] Assignee: UAB Research Foundation, Birmingham, Ala.

[21] Appl. No.: 08/851,749

[22] Filed: May 6, 1997

Related U.S. Application Data

[60] Provisional application No. 60/016,982, May 6, 1996.

[51] Int. Cl.$^6$ ............................ A61K 51/00; A61M 36/14
[52] U.S. Cl. ........................ 424/1.41; 424/1.11; 424/1.53; 424/9.1; 424/183.1
[58] Field of Search ................................. 424/1.11, 1.17, 424/1.37, 1.53, 1.61, 1.65, 9.1, 9.2, 1.41, 1.49, 178.1, 183.1; 534/7, 10–16; 530/391.3, 388.3, 391.7, 388.15, 409

[56] References Cited

U.S. PATENT DOCUMENTS

| | | | |
|---|---|---|---|
| 4,962,188 | 10/1990 | Frankel | 530/389 |
| 5,169,933 | 12/1992 | Anderson et al. | 530/391.3 |
| 5,518,888 | 5/1996 | Waldman | 435/7.23 |
| 5,776,427 | 7/1998 | Thorpe et al. | 424/1.49 |

*Primary Examiner*—Jose' G. Dees
*Assistant Examiner*—Dameron Jones
*Attorney, Agent, or Firm*—Benjamin Aaron Adler

[57] ABSTRACT

The present invention provides the synthesis and purification of a new class of compounds known as radiolabeled fusion toxins (RFT), in which both toxin and radionuclide tags are contained on the same growth factor, for example, murine granulocyte macrophage colony stimulating factor, mGM-CSF, epidermal growth factor, or murine interleukin-4, mIL-4.

11 Claims, 30 Drawing Sheets

RADIOLABELED FUSION TOXINS FOR CANCER THERAPY

CROSS REFERENCE TO RELATED APPLICATION

The present application claims priority to provisional application U.S. Ser. No. 60/016,982, filed May 16, 1996, now abandoned.

BACKGROUND OF THE MENTION

1. Field of the Invention

The present invention relates generally to the fields of immunology and radiation oncology. More specifically, the present invention relates to radiolabeled fusion toxins for cancer therapy.

2. Description of the Related Art

Colorectal cancer is the second most common malignancy in the United States. It accounts for approximately 160,000 cases each year, which results in nearly 60,000 deaths (1). The treatment of metastatic disease remains particularly unsatisfactory. Many patients with colorectal cancer have disease that is at least microscopically disseminated when they are initially seen. Surgery can control their local disease if detected early, but because these cancers are relatively resistant to chemotherapy, another systemic treatment is needed to control metastatic disease. Although the introduction of intraarterial hepatic chemotherapy has led to an improvement in the disease-free survival of patients with colorectal cancer with metastatic disease limited to the liver (2,3), the survival of patients with metastatic colorectal cancer has improved little over the last 20 years.

Radiation therapy has been demonstrated to be an effective modality in the local and regional treatment of colorectal cancer when adequate doses are delivered. For instance, 4,500–5,000 cGy has been shown to control subclinical disease, and doses of 5,500–6,500 cGy can control gross disease in many instances (4,5). However, in the common setting of systemic metastatic disease, such doses cannot be safely delivered to the tumor because of the large volume of normal tissue that would be treated (4,5).

The use of external beam radiation therapy has produced curative treatment programs for several tumor types. However, this technique has practical limitations in regards to limited field of therapy, normal tissue toxicity, and radioresistance mechanisms. Considerable research efforts have been directed at ways to "target" radioactive isotopes to sites of malignant disease. Currently, the use of monoclonal antibodies (MoAbs) directed to "tumor-associated" antigens on cancer cells represents one approach which has had success in animal model systems (6–9) and is the subject of current phase I and II trials in man (10–15). Such a strategy provides the ability to localize radioactive isotopes to multiple sites of disease with hopefully adequate amounts of radiation to produce an antitumor effect and/or radioimmune imaging for diagnostic purposes. A second strategy is to use radioactively labeled peptides able to bind to receptor positive tumor cells, e.g. octreotide to somatostatin receptors in malignant carcinoid (16,17). Research efforts which provide better radioactive isotope delivery systems and/or targeting strategies will enhance the ability to apply targeted radiation therapy to human cancer.

Radiolabeled monoclonal antibodies (single-step radioimmunotherapy) have serious limitations in treating human cancer. Successful application of radiolabeled MoAbs in a single-step protocol for radioimmunodetection and radioimmunotherapy of tumors has been hindered in man by problems related to the low percentage uptake of injected radioactivity in tumors (0.001 to 0.1% ID/g), the slow penetration of relatively large (160 kDa) intact antibodies into tumors and heterogeneous distribution, their long persistence times in normal tissues leading to high background radioactivity and bone marrow suppression, and the development of human anti-mouse antibody (HAMA) responses. To overcome these problems, the use of antibody fragments and single chain antibodies (18–23), regional administration (24–26), the use of various radionuclides (6), the use of more stable (27) or enzymatically cleavable chelating agents (28), the use of cytokines to upregulate tumor-associated antigen expression (29,30), irradiation of the tumor to increase vascular permeability (15,31–33), the use of cytokines to protect against bone marrow suppression (34,35), and the use of autologous bone marrow transplantation (12,36) have been considered. Despite these efforts, the results of clinical radioimmunotherapy of solid tumors have been disappointing but antitumor efficacy has been demonstrated in clinical trials for therapy of the radiosensitive lymphoma types of tumors.

To maximize targeting molecule (e.g. MoAb) deposition into tumor sites while minimizing radioactive isotope exposure to the bone marrow, investigators have designed strategies to separate these two components. One strategy has been to develop bifunctional MoAbs with one combining site for tumor and a second binding site for the radioactive ligand (37–47). The bifunctional antibody is administered and allowed to circulate for several days (optimal tumor deposition) and then the radioligand is administered with a rapid tissue distribution and short plasma half-life. This strategy allows tumor localization of the isotope to occur rapidly (matter of a few hours) with limited radiation doses to the bone marrow. The major limitation of this strategy has been the reduced affinity of the individual antigen combining sites (single rather than dual binding sites similar to Fab fragments), variable kinetics/distribution of the separate components making optimal schedules of therapy difficult to standardize, and normal tissue extravascular distribution of the targeting molecule.

A second approach is to take advantage of the high affinity avidin-biotin system by conjugating one of the pair to a MoAb for targeting and the other member of the pair in a radioligand preparation. In this way, the MoAb retains its affinity for tumor antigen while the short-lived radioligand has high binding affinity to the MoAb conjugate. Systems using either streptavidin radioligand (37,48–53) or biotin radioligand (37,48,54,55) have been described. These studies have generally used radioactive metal chelates ($^{111}$In, $^{90}$Y and $^{186}$Re) but Del Rosario and Wahl (56) developed a multivalent biotinylated radioiodinated polylysine peptide as well. A major drawback of this system is that the high affinity binding of radioligand to MoAb conjugate occurs with any residual MoAb in the plasma or extravascular space. The use of an additional step (39,49,57) to clear circulating antibody conjugates improves the distribution of the radioligand but results in a complex and variable schedule of MoAb conjugate infusion, plasma conjugate clearing reagent administration, and radioligand infusion.

The physical and chemical properties of a radionuclide are important in its selection for radiotherapy, e.g., the type of particulate emission must be considered (58). The potent lethality of Auger and low-energy conversion electrons has been demonstrated (59–62). This effect can best be realized with intranuclear localization of the radionuclide, which does not generally occur with radiolabeled MoAbs, but may occur with certain membrane receptor-radioligand interactions. Of course, alpha particles have a high linear energy transfer (LET) effective in cell killing and a range of several cell diameters, 40–80 µm. They may have a role for therapy of micrometastases, leukemia, and intracavitary administration (180). Beta particles are less densely ionizing and have a range longer than alpha particle emitters so that the tumor distribution requirements are less restrictive. On the other hand, for micro-metastases, the absorbed fraction for higher energy beta particles (range>tumor size) is decreased, leading to a less favorable tumor absorbed dose. The gamma-ray energies and abundances are also important physical properties, because the presence of gamma rays offers the possibility of external imaging but also adds to the whole-body radiation dose.

These physical and chemical factors must then be viewed in light of available biological information (58,63). There is substantial variation in radioligand uptake, macro- and micro-distribution, kinetics and metabolism/catabolism depending on the particular radioligand, radioligand dose, the variability of antigen/receptor expression in the tumor, its size and stage, etc. (64–77). This may be due to cell type heterogeneity, heterogeneity of antigen/receptor expression, heterogenous vascularity and capillary permeability, elevated interstitial pressure, the binding site barrier, and spatial inaccessibility (15,58,64–78). The expected nonuniform distribution of radioligand discussed above reduces the attractiveness of short-ranged alpha-emitting radionuclides for solid tumor radiotherapy. A role for alpha emitters may be feasible in specific cases such as for micrometastases or intracavitary administration for some types of cancers, such as peritoneal injection for colorectal or ovarian carcinoma (58,79,80). The longer range of beta particles can still permit uniform tumor irradiation despite a marked heterogeneity of distribution of radioactivity within the tumor. It appears desirable to deliver ionizing radiation with a range of one to several millimeters in solid tumors, as from intermediate to high-energy beta particles.

Beta emitters offer a wide choice of candidates with a selection of particle ranges and chemical properties. The use of radionuclides with some gamma emission would allow diagnostic low-dose experiments to determine biodistribution prior to administering a therapeutic dose of the exact same preparation.

Most therapeutic trials to date using radioimmunotherapy have utilized $^{131}$I, largely due to its ready availability at moderate cost, the ease of radioiodination techniques for proteins, and its long history of use in treating thyroid malignancy, rather than any careful analysis of its suitability for radioimmunotherapy. $^{131}$I has a physical half-life of 8.04 days, maximum beta energy of 0.6 MeV, average beta energy of 0.2 MeV, and is considered a medium-range beta emitter (mean range about 500 µm) with a maximum range of 1.5 mm in soft tissue. However, the yield of penetrating gamma radiation with $^{131}$I (average energy of 0.36 MeV) constitutes two-thirds of the total absorbed dose equivalent of this source in humans, resulting in higher total body doses away from the tumor volume thereby contributing to bone marrow toxicity. There is also a problem with dehalogenation producing a further loss in specific targeting, retention in tumor, and an increase in toxicity.

$^{90}$Yttrium is being studied as a radioimmunotherapy isotope (6,15,78, 81–88) because of its characteristics which include a 64 h half-life and an intermediate beta energy (2.3 MeV maximum). Since $^{90}$Y is unsuitable for quantitative imaging, $^{111}$In biodistribution data can be used to predict dose for $^{90}$Y administrations (81,82). However, even though there are similarities in tumor uptake, blood clearance and normal tissue uptake, there may be substantial differences in retention and clearance from kidney, bone, and the reticuloendothelial system.

$^{186}$Rhenium has some attractive features for radioimmunotherapy. The energy contribution from gamma rays of $^{186}$Re is 137 keV with only 8.65% abundance, which should result in a lower dose to the whole-body than with $^{131}$I. The gamma radiation from $^{186}$Re is high enough to be efficiently used for external imaging. Finally, the x-rays from $^{186}$Re are low energy radiations (59–73 keV, 9.2% abundance) and there is only a small contribution from this source to the whole body dose. Even though imaging photons in $^{186}$Re can be used particularly at therapeutic dose levels (89,90) the "matched pair" approach using $^{99m}$Tc and $^{186}$Re (the former for imaging and the latter for therapy) is a very attractive option (58,90). These can both be attached to antibodies via similar chemistry (58,91) and generally produce similar biodistributions. Rhenium-186 requires a high flux reactor to achieve adequate specific activity and it is available commercially.

Copper-64 is a positron emitting isotope ($\beta$+max=656 keV; 19% abundance) that has been used for diagnostic imaging. However, it also has a 573 keV maximum $\beta^-$ emission (38% abundance) and has been shown to be effective as a therapeutic radionuclide. This isotope has a 12.8 hour half-life, making it ideal for labeling peptides which have a short tumor localization time. Copper-64 is available from the University of Missouri Research Reactor (MURR) on a bimonthly basis in high specific activity (4,000–10,000 Ci/mmol). Copper-67 is a pure beta emitter (P-max=570 keV) with a 62 h half-life and has been used in several therapy studies. It also has a gamma emission of 185 keV (40% abundance) for imaging. It can be purchased from Brookhaven National Laboratory or Los Alamos National Laboratory; however, it is of much lower specific activity than $^{64}$Cu. Protracted lysosomal retention following cellular internalization has been reported for $^{67}$Cu.

Alpha particles and other heavy particles interact with matter producing dense trails of ionization. This effect, known as high linear energy transfer (LET), produces a greater relative biological effectiveness (RBE) than low LET radiation, principally photons and electrons. When faced with a limited number of receptors on cells, this improves the cytotoxic efficacy with the high LET emitters.

There are two additional important advantages of high LET radiation that are important for their use in radiotherapy. The first is the independence of cytotoxicity from the rate at which dose is delivered. Dose rates typically quoted for radioimmunotherapy are on the order of 20 cGy/hour or lower. These dose rates have been shown to be suboptimal in their cytotoxic effect on adenocarcinomas for low LET radiation (94). Implant therapy and brachytherapy strive to maintain dose rates of 40 cGy/hour or greater to minimize the dose rate effects (95). By comparison, dose delivered in a clinical radiation therapy external beam unit is in the range of 12,000 cGy/hour. High LET emitters have the same cytotoxicity independent of the dose rate (96,97). This is critical for radiotherapy where the dose rate begins low and is continuously decreasing. In some systems, like hepatoma (194), low dose rate does not seem to be the limitation that it is in adenocarcinomas.

The second advantage of high LET emitters is their cytotoxicity in the absence of oxygen (96). Low LET radiation requires the presence of oxygen to form free radicals that inflict the damage to the cell components that result in cell killing. Because high LET radiation is so densely ionizing, the free radicals can be formed directly and do not require the presence of oxygen. This is an advantage of high LET radiation in treatment of tumors that have areas of hypoxia. The ability to kill cells in these regions with the same dose of radiation is an advantage in therapy.

One of the disadvantages of high LET emitters for radiotherapy has been the limited selection of appropriate radionuclides. Given constraints on the half-life, photon emission and stability of daughter products, there are few candidate radionuclides for therapy. One radionuclide, Astatine-211, has the disadvantage of requiring a cyclotron that can accelerate He-4 ions in order to produce it. This, coupled with its 7.2 hour half-life, creates serious problems in supply.

With this in mind, one investigator developed a new generator system that is capable of producing Lead-212 (98). Lead-212 has a 10.6 hour half-life and decays by beta emission to $^{212}$Bi. Bismuth-212 has a 1 hour half-life and decays by beta and alpha emission to stable $^{208}$Pb. This system combines some of the most attractive aspects of radionuclides for therapy. Lead-212 is produced from Radium-224 which has a 3.6 day half-life, on the order of Molybdenum-99. The $^{212}$Pb can be generated on site in a no-carrier-added form ideal for conjugating to small amounts of reagent, thus insuring high specific activity. The half-life is ideal for therapy, long enough to insure that localization can occur, but short enough to not present serious problems in redistribution in vivo.

The advantages of high LET radiation have been exploited by using alpha-emitting radionuclides for therapy (99–104). Bloomer et al. (99) used a colloid to keep $^{211}$At in the peritoneal cavity with the hope that the superior cytotoxicity of this radiopharmaceutical would replace $^{32}$P colloid. Link and Carpenter tested a small molecule that was chemically attached to $^{211}$At (100). The combination of monoclonal antibodies and high LET emitters, directing the radiation to the tumor cell surface, has been studied (101–104). In this case, the short range of the alpha particle in vivo necessitates keeping the emission near the cell surface or inside the cell (105). Subsequently, a $^{211}$At-labeled antibody was used to treat a meningioma successfully (101).

Gansow et al. have experimented extensively with chelate systems that could be used to radiolabel antibodies with $^{212}$Bi and its parent, $^{212}$Pb (106–109). They have found that a derivative of DTPA can bind $^{212}$Bi effectively but this chelate does not bind $^{212}$Pb. DOTA, a macrocycle that contains amine and carboxylate groups, can be used to bind the $^{212}$Pb.

Little is known about the destructive effects of nuclear transformation of beta emitters in aqueous solutions. In a recent in vitro study of the chemical fate of $^{212}$Bi(DOTA)$^{1-}$ formed by beta decay of $^{212}$Pb(DOTA)$^{2-}$, the fraction of $^{212}$Bi radioactivity not complexed to DOTA was found to be 36±2% (107). Analysis of various processes responsible for excitation of the $^{212}$Bi daughter, breakup of the $^{212}$Bi-DOTA complex was ascribed to the internal conversion of gamma rays emitted by the excited $^{212}$Bi nuclide. In the case of conventional, directly labeled antibody or fusion toxin in which the majority of the protein is in the circulation, the released $^{212}$Bi is bioavailable to localize to normal organs. In a control biodistribution study of $^{212}$Bi, high levels were found in the kidney (110). In the intraperitoneal model, tumor localization and internalization takes place within the first few minutes following injection, before significant decay to $^{212}$Bi can take place. Thus, release of the $^{212}$Bi in the peritoneum should be limited considering the relatively short half life of $^{212}$Bi and uptake in normal organs may be minimal.

Targeted therapy with immunotoxins has serious limitations in treating solid cancers. Immunotoxins (IT) are a class of pharmacological reagents produced by conjugating MoAbs to potent catalytic toxins (111,114–118) which should selectively bind to and kill cancer cells while not harming normal cells. The first generation of such IT were conjugates of MoAbs to toxins such as ricin, diphtheria toxin (DT), or Pseudomonas exotoxin (PE). The plant toxin ricin, one of the most toxic substances known, is a lectin with specificity for galactose terminating glycoproteins. Ricin consists of a 30 kDa A chain and a 30 kDa B chain joined by a disulfide bond. The A chain subunit is an enzyme which inactivates 28S components of the 60S subunit of ribosomes. The B chain subunit binds whole ricin to native receptors on the cell surface. The native receptors are galactose-containing glycoproteins that are present on all eukaryotic cells. The conjugation of A chain alone to MoAbs circumvents the risk of nonspecific binding. Intact ricin conjugates have limited utility in vivo. This is attributable to the galactose binding site of ricin having a high affinity for the galactose receptor on the cell surface of normal cells. IT consisting of ricin A chain conjugated to MoAbs with reactivity against human colon cancer have been synthesized and shown to inhibit protein synthesis and to be cytotoxic to human colon cancer cells in vitro (119–126), and to inhibit the growth of human tumor xenografts (127). Investigators have constructed IT that contain B chain with its native binding site chemically blocked (125,128–130). The obstruction of the B chain binding site is meant to prevent nonspecific toxicity to normal cells. Cattel et al. (125) reported that blocked intact ricin B chain IT displayed more selective cytotoxicity to target human colorectal adenocarcinoma cell lines than non-blocked IT and was much more potent than the ricin A chain IT.

Although there are reports describing the in vitro killing of tumor cells by IT, there are few papers reporting the successful use of IT against carcinomas in vivo. IT with reactivity against human colon and pancreatic tumors have been synthesized (119–127,131–133). Other IT have been used in therapeutic studies in animal tumor xenograft models (reviewed in 134,135) and recently in clinical studies in patients with leukemia, breast cancer, and melanoma (136–140). Initial clinical trials have not thus far shown significant activity of IT in patients with solid tumors (112,141,142). A pattern of mixed regression, which is defined as a 50% or greater reduction in size in one or more metastases combined with an increase in the size of one or more concurrent lesions or the appearance of a new lesion after the initiation of therapy, occurred in a minority of patients with metastatic malignant melanoma and colorectal cancer treated with IT specific for each of these cancers (141). Clinical responses in patients with hematologic malignancies have been more encouraging. In patients with B-cell lymphoma, IT containing MoAbs reactive with B-cell antigens coupled to either ricin A chain or blocked ricin produced partial regressions, which are defined as a 50% or more reduction of the overall tumor burden, in about 40% of patients (141). Problems in therapeutic applications, particularly toxicity, make it clear that simply conjugating an antibody to a toxin will not cure cancer. Some of the antibodies used for the preparation of IT to treat solid tumors had cross-reactivity with neural tissue or bone marrow which resulted in toxicity to these tissues (142).

In the clinical trials using ricin-based IT, the nonspecific toxicity of the toxin moiety remains the major problem (112). Capillary leak syndrome and liver dysfunction are the limiting toxicities for deglycosylated ricin A chain and blocked ricin, respectively (112). With PE, the dose-limiting toxicity is damage to the liver. The inability to deliver repeated doses of IT to patients due to antibody formation is a major concern. Although the formation of HAMA can be avoided by the use of humanized antibodies or humanized forms of single-chain Fv-IT, the problem of formation of antibodies against the toxin moiety remains unsolved (112). Antibodies to DT already exist in most individuals who received immunizations with diphtheria, pertussis, and tetanus. These factors may limit the therapeutic efficacy of IT.

Recombinant fusion toxins may be useful for therapy of solid cancers. Progress in the knowledge of the structure and function of several toxins, advanced cloning and preparation technologies, and the development of recombinant antibodies has made it possible to construct new kinds of IT. Protein toxins such as PE, DT, and ricin may be useful in cancer therapy because they are among the most potent cell-killing agents. The genes encoding these three toxins have been cloned (112,145) and expressed in *Escherichia coli* (*E. coli*). Both DT and PE inhibit protein synthesis by catalytically inactivating elongation factor 2 in the cytosol which is necessary for protein synthesis (111,145,146). To get to the cytosol, toxins must first bind to the target cell, be internalized by endocytosis, and translocate to the cytosol. Only a few molecules need reach the cytosol to kill a cell. A major advance in the IT field has been the production of recombinant fusion toxins (111,145,146); these were created by fusing DNA elements encoding binding regions of antibodies, growth factors, or cytokines to a mutant form of a toxin gene. Recombinant fusion toxins bind to cells, undergo endocytosis, and kill cells that are recognized by the antigen- or receptor-binding domain. Although these molecules are not IT in a strict sense, because they do not contain an antibody moiety, they are closely related to IT in their mode of targeting and killing of cells.

A number of recombinant fusion toxins have been developed recently for use in receptor-targeted cancer therapy (111,112,145,146). Many tumors express higher levels of growth factor receptors or antigens than normal cells, and often they express receptors for more than one ligand. These genetically engineered chimeric fusion toxins have been generated by deleting the portion of the toxin gene encoding the cell binding domain and replacing it with DNA encoding an alternative cell binding peptide such as a growth factor, lymphokine, or single chain antibody.

In 1988, it was shown that recombinant forms of antibodies consisting of variable domains of the heavy and light chains linked together via a peptide linker were able to bind antigen (111). Such proteins were termed single chain antibodies, or Fv domains. Anti-Tac(Fv) reactive with the interleukin-2 receptor (IL-2R) was fused to a mutant form of PE called PE40 in which the binding domain of the native toxin has been deleted (111,146). This recombinant IT killed leukemia cells in vitro.

DT is a single-chain polypeptide of 535 residues produced by *Corynebacterium diphtheriae*. DT and recombinant forms of DT have been coupled to antibodies, growth factors, and cytokines and have been shown to have cytotoxic activity in vitro. The receptor-binding domain of native DT has been replaced with IL-2, the Fv region of anti-Tac antibody, IL-4, IL-6, or EGF. The resulting recombinant fusion toxins are selectively toxic to cells that express the specific receptor.

Limited transvascular diffusion of IT into solid tumors represents a problem. Penetration is mainly dependent on size; the smaller the IT, the better its tumor penetration (111). Affinity also influences tumor penetration (111). Fv fragments of antibodies (22 kDa) penetrate tumors better than Fab fragments (45 kDa) which in turn penetrate better than intact antibodies (188). Due to their larger size, the ability of IT to penetrate into solid tumors by diffusion and convection is impaired, although they have a half-life in the circulation of 4–8 hours or more. Therefore, first-generation IT (200 kDa) should take much longer to penetrate a 1 cm diameter solid tumor than a recombinant fusion toxin (60 kDa). Tumor penetration is much more effective for small recombinant fusion toxins, but they are also cleared very rapidly from the circulation ($T_{1/2}$=20–40 minutes).

The prior art is deficient in the lack of effective means of inhibiting the growth of various cancers. The present invention fulfills this longstanding need and desire in the art.

SUMMARY OF THE INVENTION

The present invention describes the synthesis and purification of a new class of compounds known as radiolabeled fusion toxins (RFT), in which both toxin and radionuclide tags are contained on the same growth factor (murine granulocyte macrophage colony stimulating factor (mGM-CSF) or murine interleukin-4 (mIL-4)), that are tested for binding reactivity, protein synthesis inhibition and cytotoxicity in in vitro studies with mouse and human colon cancer cell lines and for in vivo binding and therapy in a syngeneic colon cancer model and in athymic nude mice bearing human colon cancer xenografts. The killing of cells by radiolabeled antibodies occurs at a distance from the antibody binding site, and is a function of the energy and type of emission of the radionuclide. The cytotoxic activity of recombinant fusion toxins occurs after internalization of toxin into the cell, enzymatic inactivation of cellular ribosomes, and termination of protein synthesis. Radiolabeling the entire recombinant fusion toxin molecule produces a radiolabeled fusion toxin through the synthesis of a hybrid molecule that retains the cytotoxic advantages of both the radionuclide and the fusion toxin. RFT are capable of killing tumor cells by two different mechanisms, inhibition of protein synthesis and DNA damage. The addition of the radionuclide to the fusion toxin allows for the killing of cells to which the fusion toxin does not bind or internalize.

Despite the efficacy of IT, genetically engineered recombinant fusion toxins have several advantages over IT which include: 1) large amounts of recombinant fusion toxins can be produced easily and at a lower cost by *E. coli* expression systems and purified to near homogeneity by standard column chromatography in comparison to most IT which are heterogeneous products; 2) the protein product and its binding characteristics are uniform and are not affected by chemical derivatization; 3) recombinant fusion toxins are more easily modified by mutating the genes that encode them to increase chemical stability; 4) recombinant fusion toxins appear to be more effective in producing tumor regressions in animal models; and 5) they have a lower molecular weight leading to a shorter plasma half-life and better tumor penetration.

The recombinant fusion toxin $DT_{390}$-mGM-CSF that targets DT to the murine receptors for granulocyte macrophage colony stimulating factor (mGM-CSF) has been produced. The high affinity receptor for GM-CSF consists of two components designated as α and β subunits. The binding of GM-CSF to the high affinity GM-CSF receptor forms a high affinity receptor complex. The binding of GM-CSF to this receptor causes rapid internalization of the ligand-receptor complex. The receptors for GM- CSF are abundantly expressed on the surface of acute myeloid leukemia (AML) cells and malignant cells from solid tumors, including melanoma, small-cell carcinoma of the lung, breast cancer, renal carcinoma, gastric carcinoma, ovarian carcinoma, and colon cancer. GM-CSF-DT would be useful in the treatment of AML and solid tumors.

The present invention uses gene therapy techniques to induce expression of high affinity mGM-CSF or mIL-4 receptors on human colon cancer or lung cancer cell surfaces which bind radioisotope-labeled $DT_{390}$-mGM-CSF or $DT_{390}$-mIL-4. In order to accomplish this, one must: 1) produce a mouse colon cancer cell line which has stable expression of the high affinity mGM-CSF receptor; 2) design and produce radiolabeled fusion toxins consisting of $DT_{390}$-mGM-CSF linked to radionuclides ($^{131}$I, $^{90}$Y, $^{186}$Re, $^{212}$Bi, $^{212}$Pb, $^{64}$Cu, $^{67}$Cu and many others as are known in the art) and show their therapeutic activity, toxicity, biodistribution, pharmacokinetics, and dosimetry in a regional model of intraperitoneal disease; 3) develop methods to genetically induce surface membrane expression of mGM-CSF or mIL-4 receptors in human colon and lung cancer cells; 4) utilize an animal model of human colon cancer cells transplanted into the peritoneum of athymic nude mice for intraperitoneal transduction of mGM-CSF receptor followed by treatment with the optimal radiolabeled fusion toxin developed herein. This approach could be utilized for the treatment of patients with gastrointestinal cancer that have peritoneal disease. The $DT_{390}$-mGM-CSF or $DT_{390}$-mIL-4 would not bind to human hematopoietic cells and result in toxicity since mGM-CSF does not bind to the human GM-CSF or human IL-4 receptor. Furthermore, human GM-CSF does not bind to the mGM-CSF receptor, so that there would not be any inhibition of binding of $DT_{390}$-mGM-CSF to mGM-CSF receptor transduced human colon cancer cells by hGM-CSF. The same situation would exist with respect to the binding of $DT_{390}$-mIL-4 to mIL-4 receptor transduced human colon or lung cancer cells.

To illustrate a treatment strategy which combines gene therapy techniques to induce expression of high affinity mGM-CSF or mIL-4 receptors on tumor cell surfaces and optimal radioisotope-labeled fusion toxin to deliver therapeutic doses of radiation, the following studies were conducted. Using mouse colon cancer cell lines which have stable or transient expression of the high affinity receptor mGM-CSF or mIL-4 to: produce appropriate radioactive fusion toxins using mGM-CSF or mIL-4 linked to DT capable of binding to the receptor expressing tumor cells in vitro and in vivo; optimize in vivo delivery of radioactive fusion toxins in animal tumor models composed of receptor expressing tumor cells; develop methods to genetically induce tumor cell surface membrane expression of mGM-CSF or mIL-4 receptors (xenogeneic receptors in human colon cancer cells); utilize animal models to demonstrate the antitumor efficacy of Genetic Radio-Isotope Targeting Strategy using intraperitoneal transduction and optimal radiolabeled fusion toxin.

In one embodiment of the present invention, there is provided a composition of matter comprising radiolabeled fusion toxins (RFT), in which both toxin and radionuclide tags are contained on the same growth factor such as murine granulocyte macrophage colony stimulating factor, mGM-CSF or murine interleukin-4, mIL-4.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DT$_{390}$-mIL-4 fusion toxin was mixed with 11B11 antibody for 15 min and then added at various concentrations to C1498 cells for 24, 48, or 72. Control untreated cells were cultured also. The number of cells/well was determined.

Figure 21:
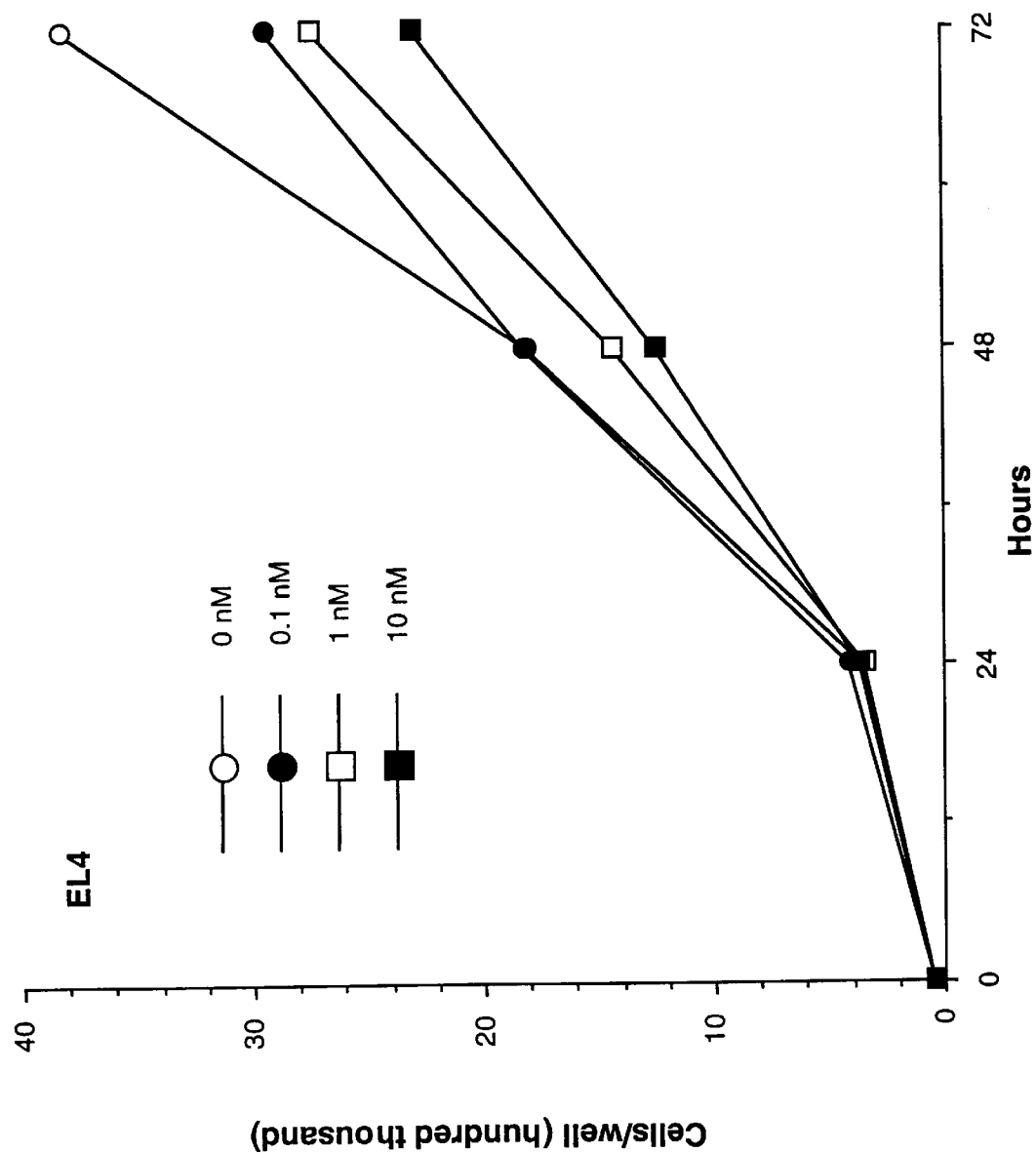

FIG. 21 shows cell proliferation inhibition activity of DT$_{390}$-mIL-4 fusion toxin on EL4 cells. DT$_{390}$-mIL-4 fusion toxin was added at various concentrations to EL4 cells for 24, 48, or 72 hours. Control untreated cells were cultured also. The number of cells/well was determined.

Figure 22:
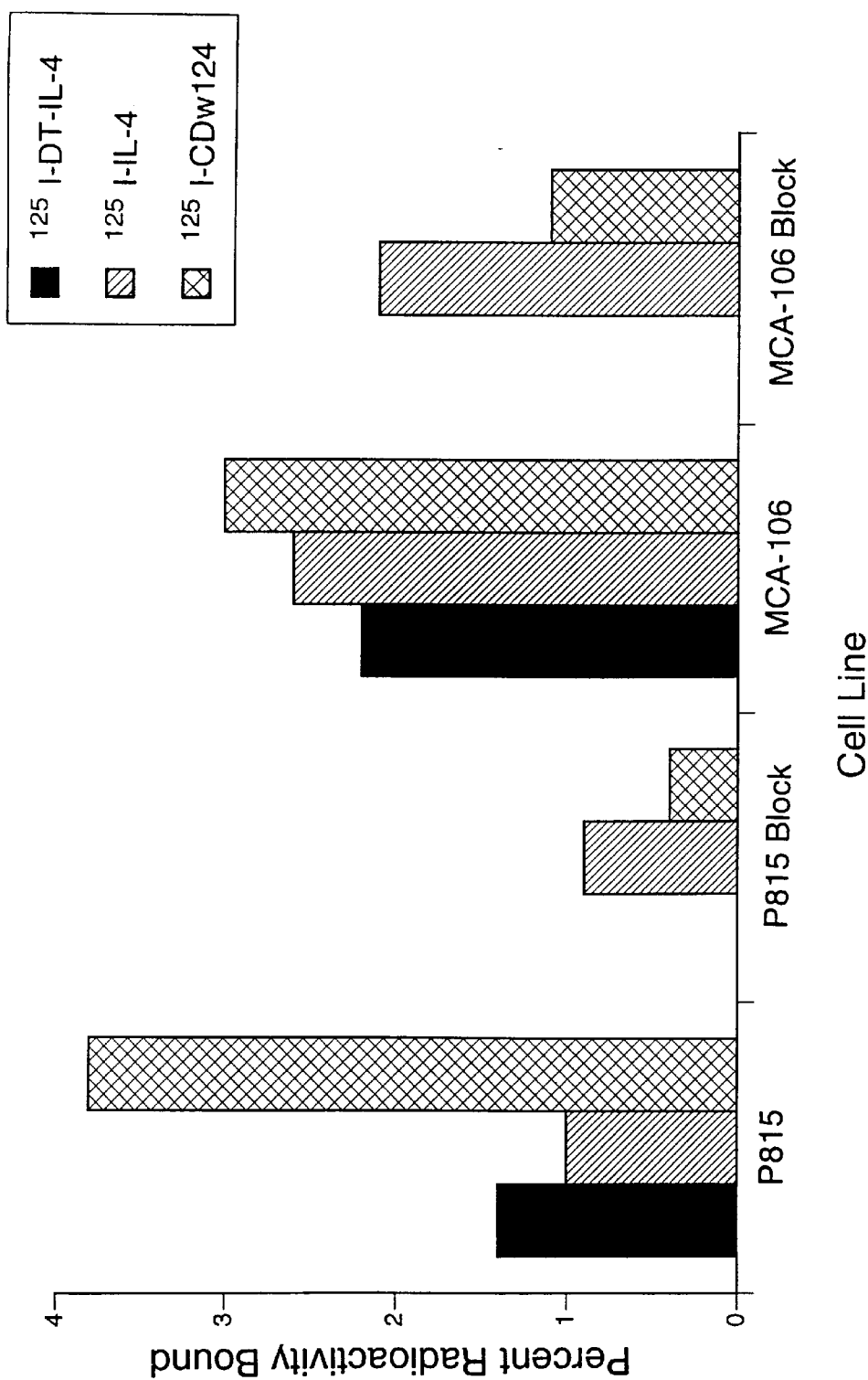

FIG. 22 shows an analysis of binding activity of $^{125}$I-labeled DT$_{390}$-mIL-4, mIL-4, and CDw124 antibody to P815 and MCA-106 cells. The bars depict percent radioligand bound/cell in triplicate samples., Nonspecific binding of $^{125}$I-labeled ligands was measured in the presence of excess unlabeled CDw124 antibody.

Figure 23:
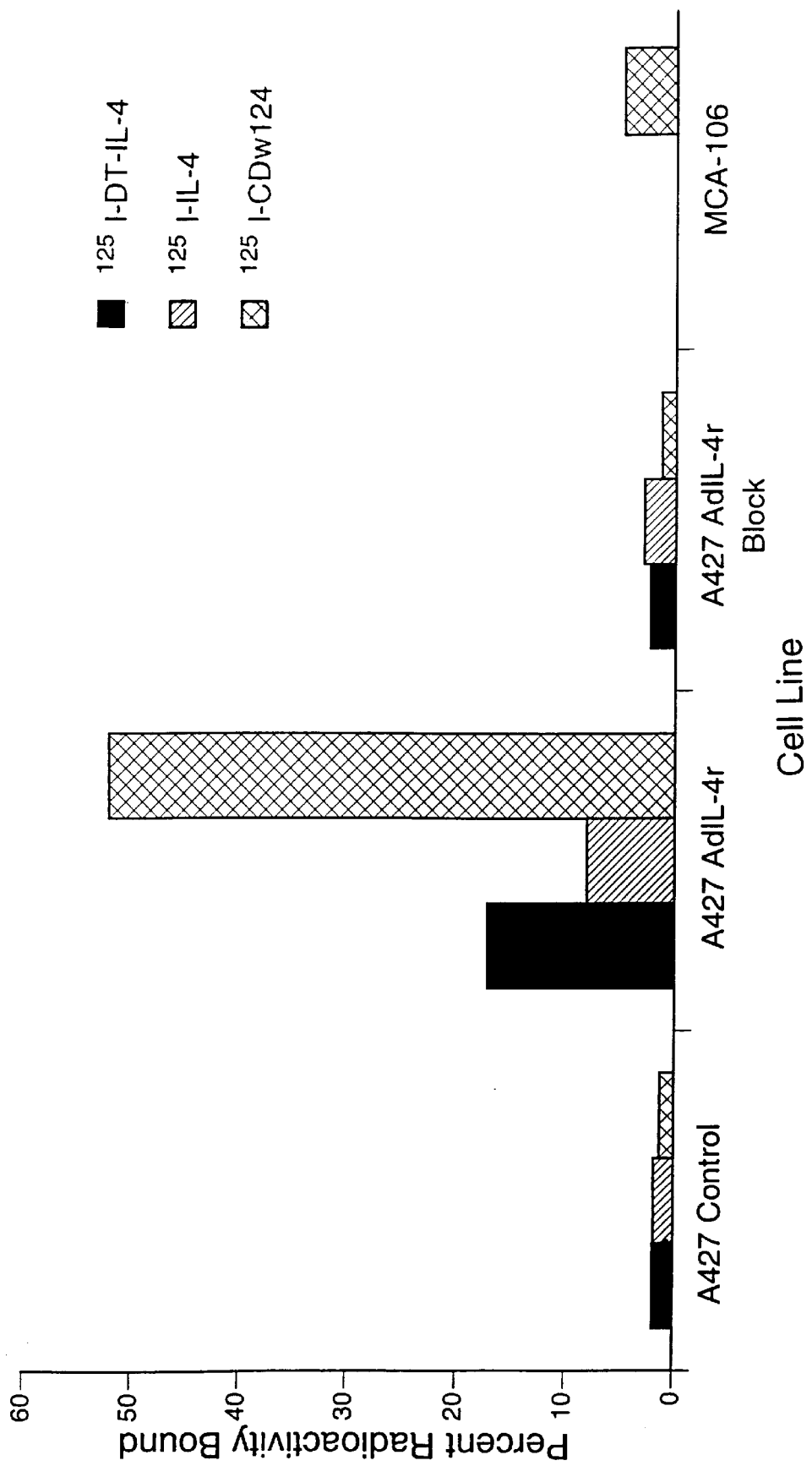

FIG. 23 shows an analysis of binding activity Of $^{125}$I labeled DT$_{390}$-mIL-4, mIL-4, and CDw124 antibody to AdCMVmIL-4r transduced A427 cells. A427 cells were infected with 10 pfu/cell and assayed 48 hours post-infection. Uninfected A427 cells were analyzed in comparison. The bars depict the percent radioligand bound/cell for a representative experiment run in triplicate. Binding to uninfected A427 control cells and MCA-106 cells was also analyzed. Nonspecific binding of $^{125}$I-labeled ligands was measured in the presence of excess unlabeled CDw124 antibody.

Figure 24:
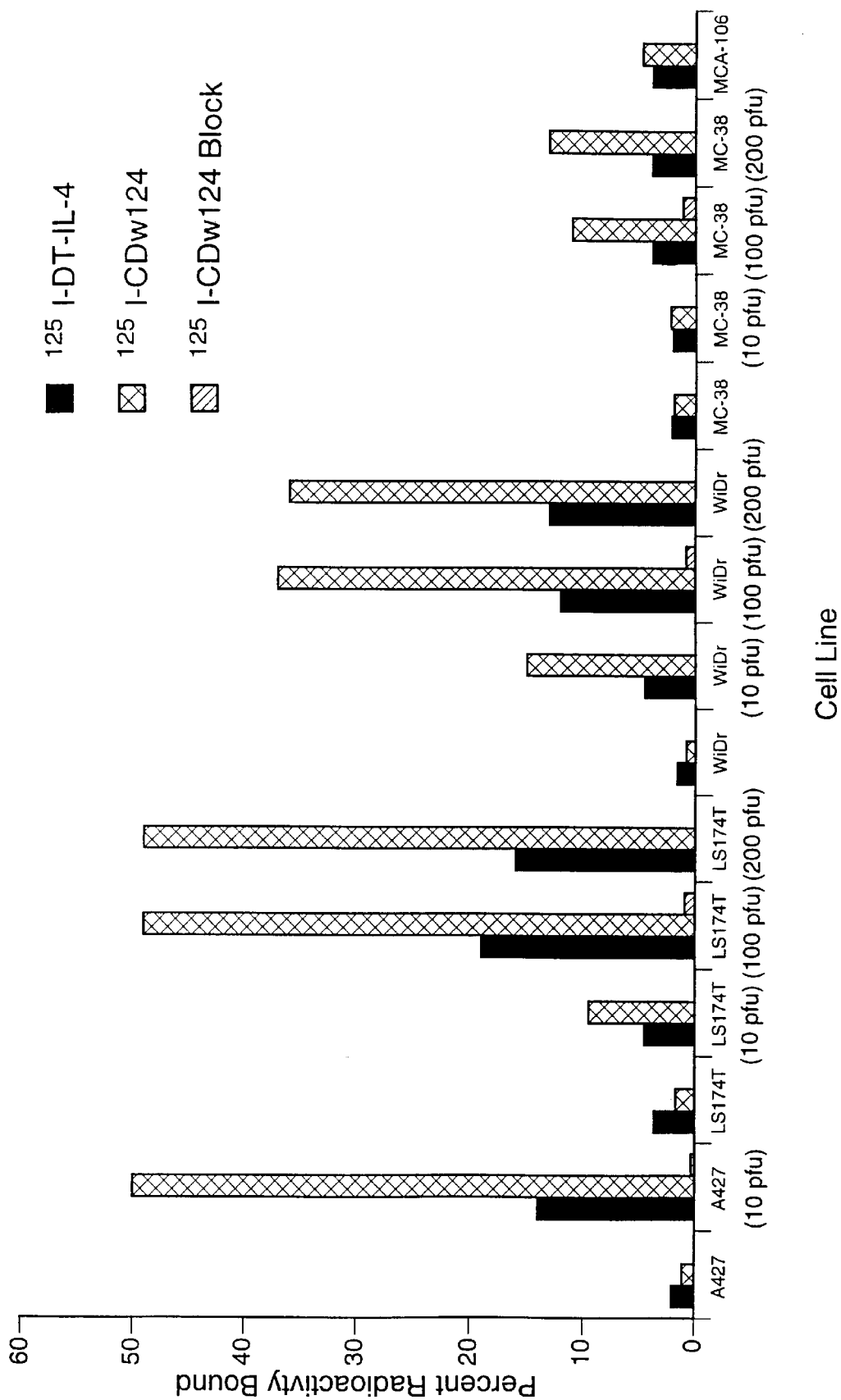

FIG. 24 shows an analysis of binding activity of 125I-labeled DT$_{390}$-mIL-4 and CDw124 to LS174T, WiDr, and MC-38 cells transfected with different viral plaque forming units ranging from 10 to 200 pfu/cell. Uninfected A427 cells as well as MCA-106 cells constitutively expressing mIL-4 receptor were analyzed in comparison. The bars depict percent radioligand bound/cell in triplicate samples. Nonspecific binding of $^{125}$I-labeled CDw124 antibody was measured in the presence of excess unlabeled CDw124 antibody.

Figure 25:
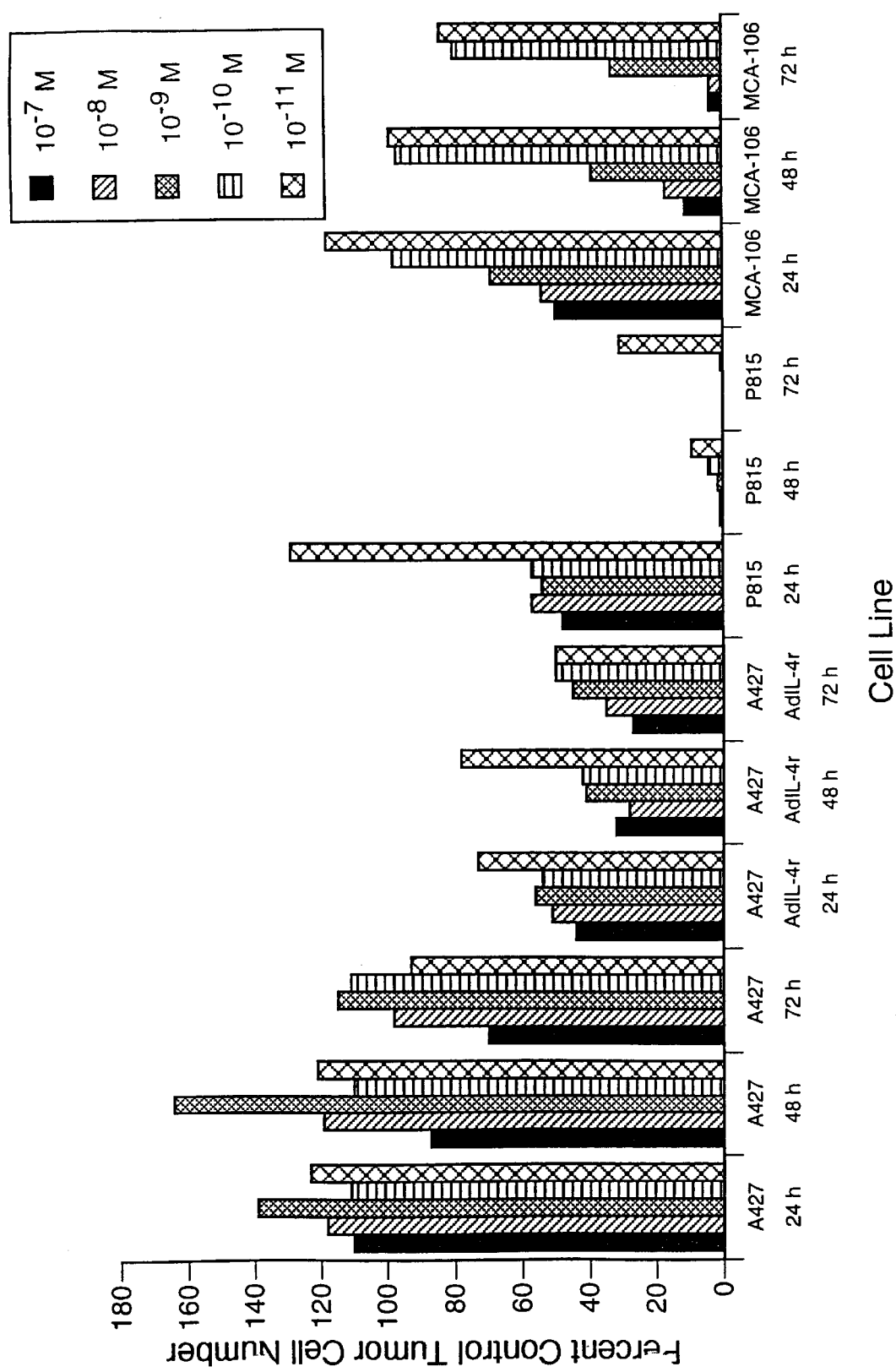

FIG. 25 shows inhibition of cell proliferation of DT$_{390}$-mIL-4 fusion toxin at various concentrations on AdCMVmIL-4r infected A427 cells at 10 pfu/cell. Uninfected A427, P815, and MCA-106 cells were used as controls. Cell numbers relative to untreated cells were determined at 24, 48, and 72 hours after fusion toxin treatment.

Figure 26:
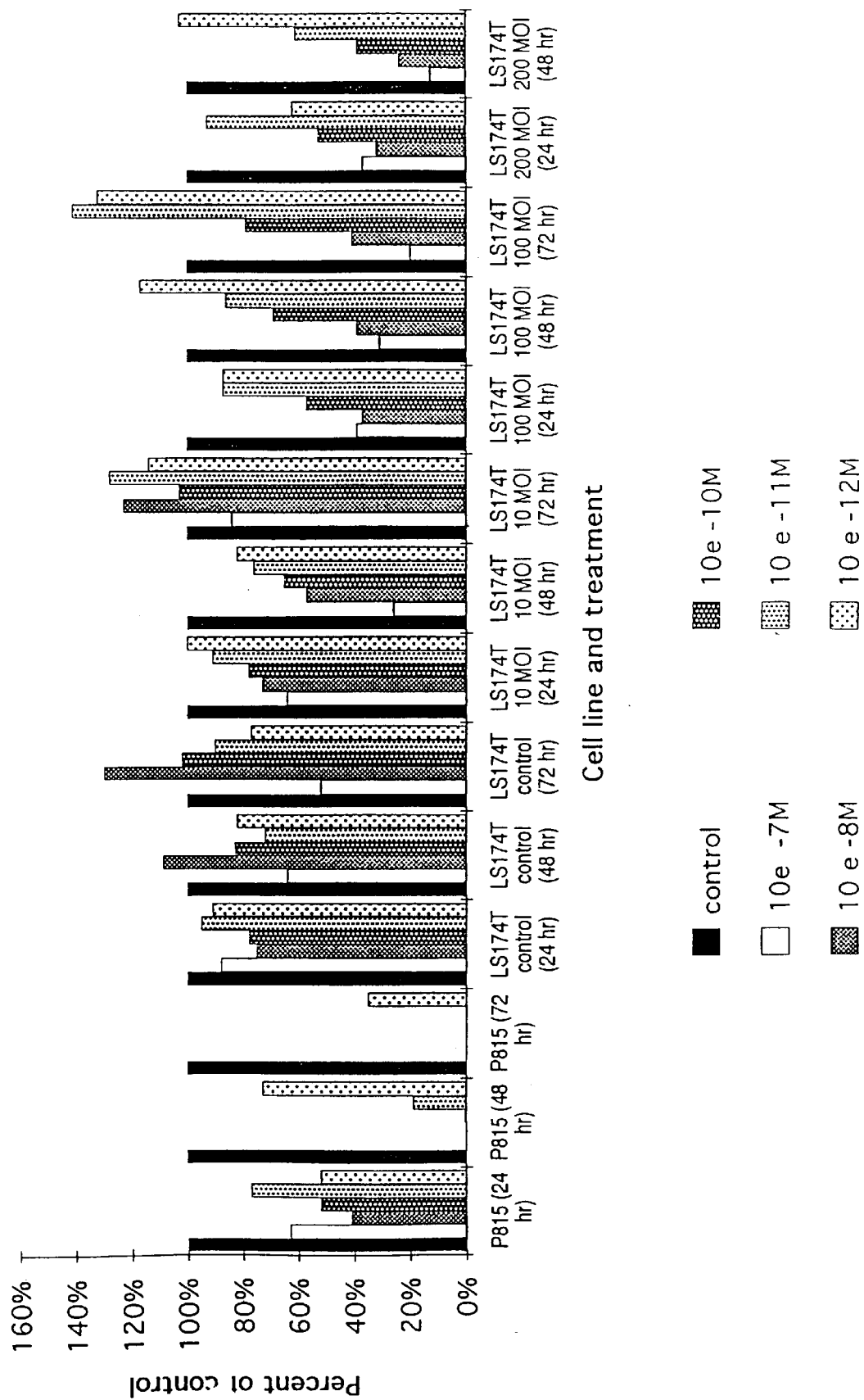

FIG. 26 shows inhibition of cell proliferation of DT$_{390}$-mIL-4 fusion toxin at various concentrations on AdCMVmIL-4r infected LS174T cells with viral pfu/cell ranging from 10 to 200 (MOI). Uninfected LS174T and P815 cells were used as controls. Cell numbers relative to untreated control cells were determined at 24, 48, and 72 hours after fusion toxin treatment.

Figure 27:
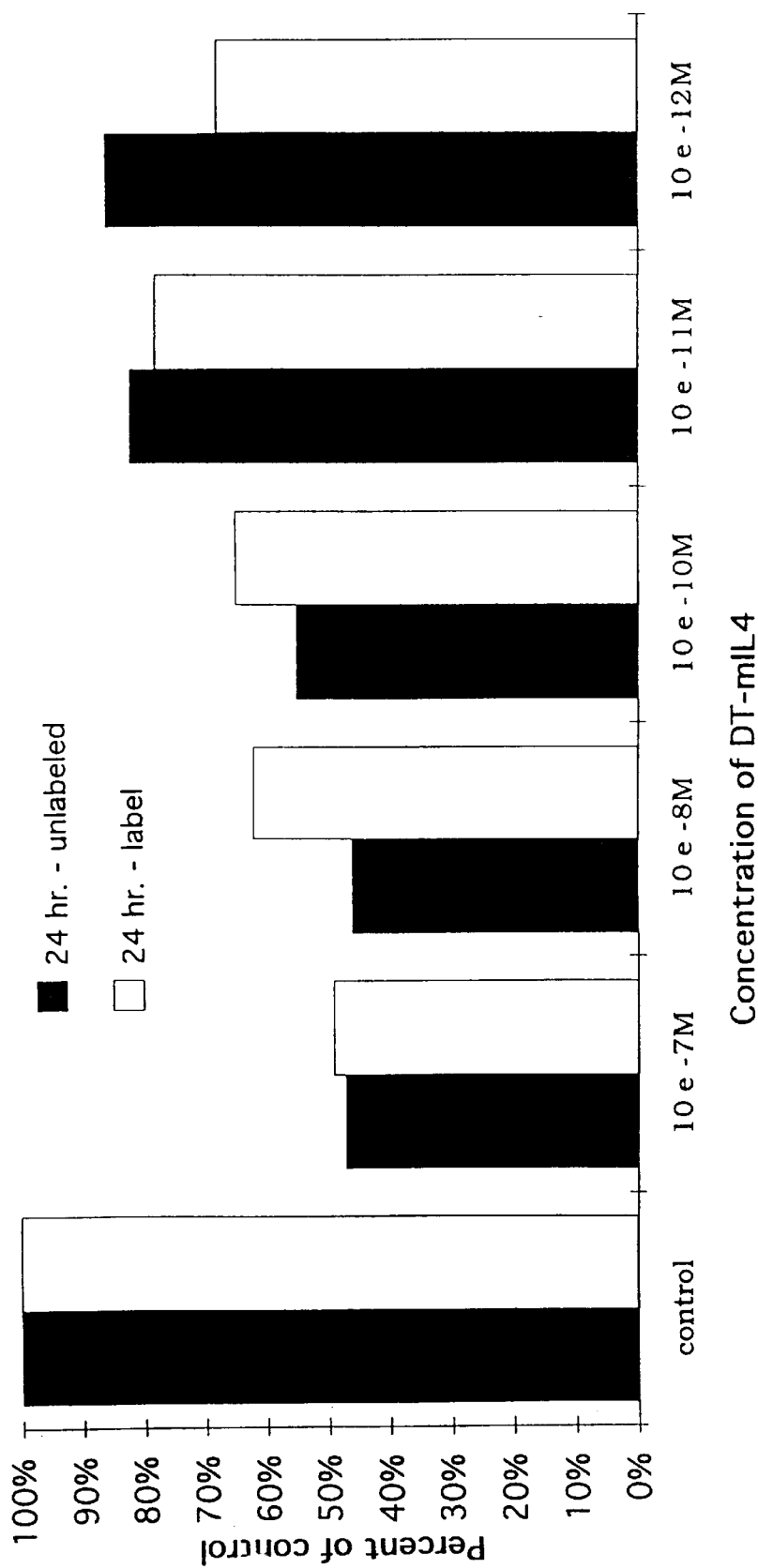

FIG. 27 shows inhibition of cell proliferation of $DT_{390}$-mIL-4 and $^{125}$I-labeled $DT_{390}$-mIL-4 fusion toxins at various concentrations on P815 cells. Cell numbers relative to untreated control cells were determined at 24 hours after fusion toxin treatment.

Figure 28:
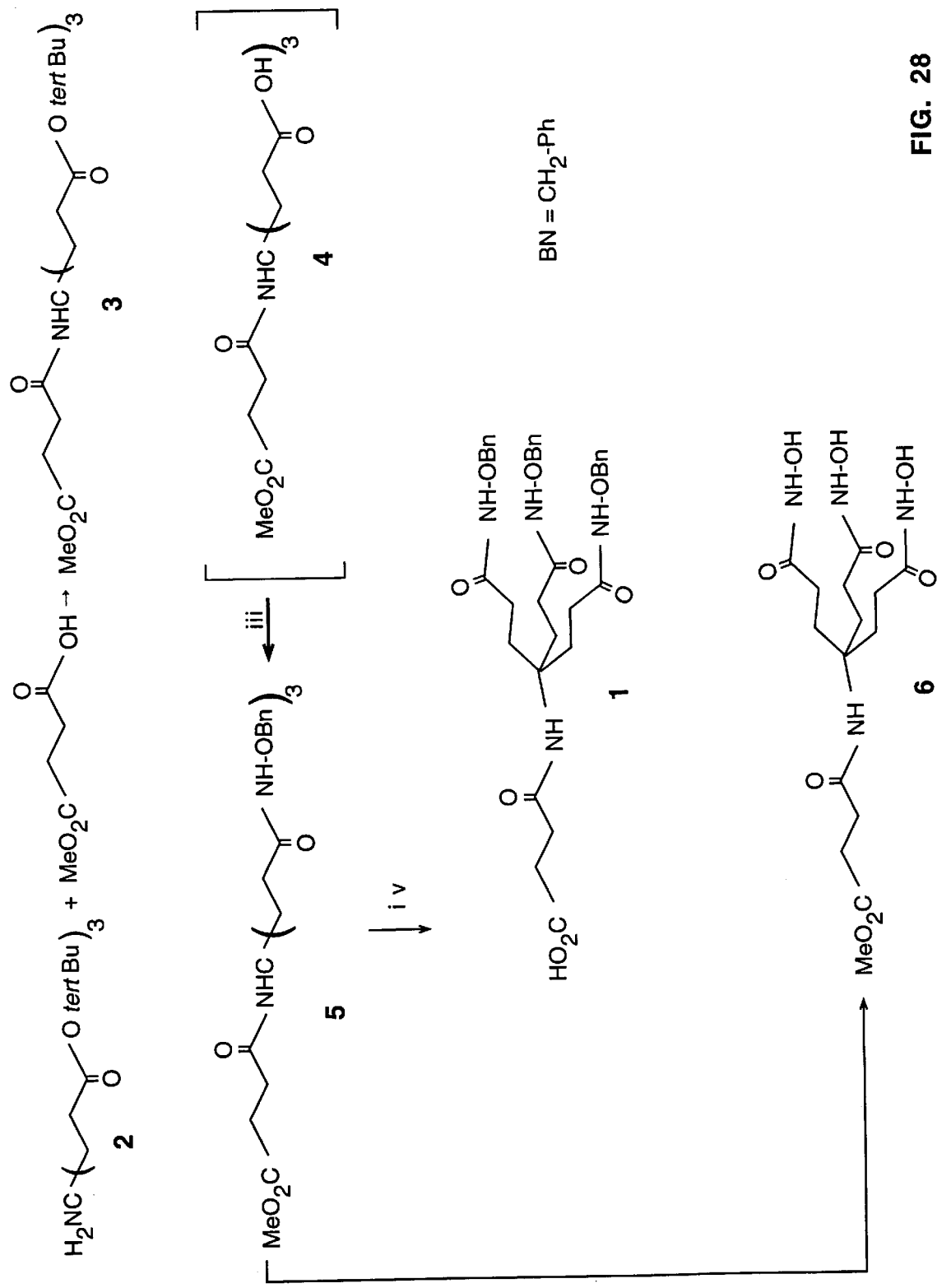

FIG. 28 shows the synthetic scheme of trisuccin.

Figure 29:
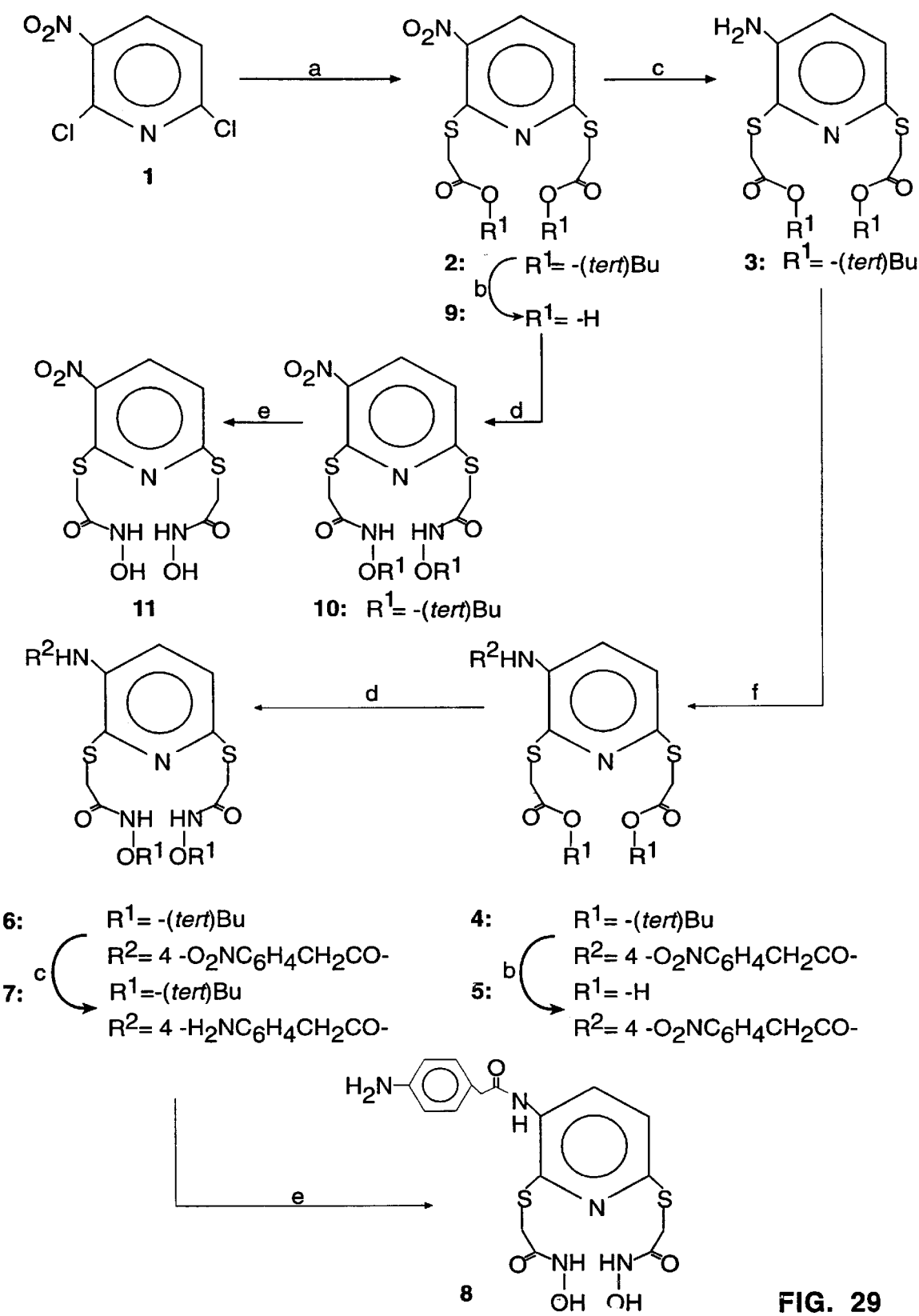

FIG. 29 shows the synthetic scheme of a new pyridine-derived hydroxamate bifunctional chelating agent.

DETAILED DESCRIPTION OF THE INVENTION

The present invention provides a composition of matter, comprising a recombinant fusion toxin comprising: a toxin fused to a targeting moiety which binds to a receptor overexpressed by tumor cells, wherein said toxin-targeting fusion moiety is labeled with a radionuclide. Although any toxin may be useful in the methods of the present invention, preferably, the toxin is selected from the group consisting of diphtheria toxin, ricin, gelonin and pseudomonas exotoxin. Similarly, various radionuclides may be used to radiolabel the fusion toxin. Representative examples of suitable radionuclide include $^{90}$Y, $^{186}$Re, $^{188}$Re, $^{64}$Cu, $^{67}$Cu, $^{212}$Pb, $^{212}$Bi, $^{123}$I, $^{211}$At, $^{213}$Bi and $^{131}$I. Representative examples of a targeting moiety that binds to receptors overexpressed by tumor cells is selected from the group consisting of the interleukin-4, interleukin-2, epidermal growth factor and the granulocyte macrophage colony stimulating factor. Such receptors are overexpressed on a wide variety of tumor cells, including acute myeloid leukemia cells, melanoma cells, small-cell carcinoma of the lung cells, breast cancer cells, renal carcinoma cells, glioma cells, gastric carcinoma cells, ovarian carcinoma cells, and colon cancer cells. In one embodiment, the recombinant fusion toxin is $DT_{390}$-mGM-CSF. In another embodiment, the recombinant fusion toxin is $DT_{390}$-mIL-4.

The present invention also provides a method of killing a tumor cell, comprising the step of contacting said cell with the composition of the present invention. The types of tumor cells which can be treated with this methods are similar to those above. The present invention also provides a method of treating a tumor cell in an individual in need of said treatment, comprising the step of administering to said patient an effective dose of the pharmaceutical composition.

It is specifically contemplated that pharmaceutical compositions may be prepared using the novel composition of the present invention. In such a case, the pharmaceutical composition comprises the novel radiolabeled fusion toxin of the present invention and a pharmaceutically acceptable carrier. A person having ordinary skill in this art would readily be able to determine, without undue experimentation, the appropriate dosages and routes of administration of the novel composition of the present invention.

The purpose of radiolabeling the entire recombinant fusion toxin molecule to produce a radiolabeled fusion toxin (RFT) is to synthesize a hybrid molecule that retains the cytotoxic advantages of both the radionuclide and the fusion toxin. RFT are capable of killing tumor cells by two different mechanisms, inhibition of protein synthesis due to the toxin and DNA damage due to the radiation. The addition of the radionuclide to the fusion toxin offers the potential for the killing of cells to which the fusion toxin does not bind due to the cross-fire effect of emitted radiation. The reason for not labeling the mGM-CSF separately with these cytotoxic agents and administering them as a mixture is that they would compete with each other for binding at the tumor site. Other investigators have constructed a RIT by conjugating ricin A chain to MoAb 791T/36 raised against a human osteogenic sarcoma cell line which was then radiolabeled with $^{125}$I or $^{131}$I, and the biodistribution of the RIT was determined in normal mice (131,132). A report of the biodistribution of an $^{111}$In-labeled ricin A chain IT against CEA in tumor-bearing animals indicated increased hepatic uptake as compared to radiolabeled MoAb (133).

The present invention provides 1) the synthesis of new recombinant fusion toxins made with DT and mGM-CSF or mIL-4; 2) details the binding and cytotoxicity of RFT in vitro; 3) demonstrates the use of an RFT as a colon cancer therapeutic agent in an animal model, and 4) optimizes the RFT therapeutic strategy in an animal model.

The RFT binding and therapy studies are carried out in 2 phases: (1) intraperitoneal colon tumors are stably or transiently transduced with the genetic constructs for mGM-CSF or mIL-4 receptor; and (2) intraperitoneal colon tumors that undergo direct intraperitoneal gene transfer in vivo followed by RFT therapy. The intraperitoneal administration of RFT should lead to high binding if the mGM-CSF-DT or mIL-4-DT binds rapidly to the genetically transduced receptor still in the peritoneal cavity. The following examples are given for the purpose of illustrating various embodiments of the invention and are not meant to limit the present invention in any fashion.

Construction, expression, and purification of murine GM-CSF-DT fusion toxin and testing of enzymatic and cytotoxic activity Vallera has produced and tested a recombinant fusion toxin consisting of mGM-CSF linked to DT (173). The DNA fragments encoding the structural gene for $DT_{390}$ and mGM-CSF were obtained by separate PCRs with the sizes of 1239 bp and 380 bp respectively. After the third PCR, the resulting SOE product, $DT_{390}$-mGM-CSF hybrid gene was generated with 1601 bp size. The $DT_{390}$-mGM-CSF hybrid gene encodes a Nco I restriction site, an ATG initiation codon, the first 389 amino acids of the DT, a 21 amino acid interchain spacer, the mature murine GM-CSF polypeptide, and an Xho I restriction site. After digestion, the $DT_{390}$-mGM-CSF hybrid gene was cloned into the pET21d plasmid under the control of the IPTG inducible T7 promoter to create pDT-GM-CSF. Restriction endonuclease digestion and DNA sequencing analysis were used to verify that $DT_{390}$mGM-CSF hybrid gene sequence had been cloned in frame. The plasmid was sequenced and the junctional region was found to encode for amino acids 333 to 389 of DT with one substitution of alanine at position 356 by serine. The linker was found to encode for the following amino acids, [(Gly)$_4$ Ser]$_2$ Gly Ala (Gly)$_2$ Ser (Gly)$_4$ Ser Phe (SEQ ID NO:1) joined by a sequence encoding amino acids 27 through 175 of mGM-CSF.

Expression of the fusion protein in E. coli was induced with IPTG at 37° C. Coomassie blue stained SDS-polyacrylamide gel of whole bacterial lysate post IPTG induction showed a protein migrating at 58 kDa, which corresponds to the expected size for $DT_{390}$-mGM-CSF protein. The localization study of the expressed fusion protein revealed that $DT_{390}$-mGM-CSF was retained in the inclusion bodies. To extract the $DT_{390}$-mGM-CSF protein, the inclusion bodies were isolated, denatured and refolded.

Following the renaturation procedure, the crude $DT_{390}$-mGM-CSF was purified by sequential chromatography. The elution from the anion-exchange Q-sepharose column showed an enrichment of a protein with an electrophoretic mobility corresponding to an apparent molecular mass of 58 kDa. In order to further purify this fusion protein, pooled peak fractions from the anion-exchange Q-sepharose column were subjected to HPLC using a TSK-250 size exclusion column. The final product was 80% pure. Additional analyses of this $DT_{390}$-mGM-CSF protein with immunoblotting was performed. Anti-DT antiserum was able to recognize the $DT_{390}$-mGM-CSF both in the crude bacterial lysate and after renaturation.

Protein synthesis inhibition by DT is due to fragment A catalyzed ADP-ribosylation of cytoplasmic EF-2. To determine whether the $DT_{390}$-mGM-CSF protein also displays such enzymatic activity, a cell free assay system was employed, in which rabbit reticulocyte lysate, a source of EF-2, was exposed to either native DT or $DT_{390}$-mGM-CSF in the presence of [$^{32}$P]-NAD. Incubation with either toxin revealed a similar dose dependent increase in [$^{32}$p] incorporation into the TCA-precipitable fraction (FIG. 3). This result confirmed that $DT_{390}$-mGM-CSF possesses ADP-ribosyl transferase activity. To characterize the cytotoxic activity of $DT_{390}$-mGM-CSF, a protein synthesis inhibition assay was devised using the mGM-CSF dependent myelomonocytic leukemia cell line FDCP2.1d. The cytotoxicity was evaluated by measuring the inhibition of [$^{3}$H] thymidine uptake. The ability of various concentrations of $DT_{390}$-mGM-CSF to inhibit the protein synthesis of FDCP2.1d cells was examined. FDCP2.1d cells were inhibited by $DT_{390}$-mGM-CSF in a dose dependent manner with an $IC_{50}$ of $5\times10^{-11}$ M or 3 ng/ml (FIG. 4). To determine if the cytotoxic activity of $DT_{390}$-mGM-CSF on FDCP2.1d cells was mediated by the binding of the mGM-CSF. moiety, other toxins including $DT_{390}$-hIL-2, $DT_{390}$-mIL-4, and native DT were assayed for their activity against FDCP2.1d. In contrast to $DT_{390}$-mGM-CSF, FDCP2.1d cells were resistant to $DT_{390}$-hIL-2, $DT_{390}$-mIL-4, and native DT up to a concentration of $1\times10^{-8}$ M. Furthermore, anti-mGM-CSF antibodies blocked the cytotoxic effect of $DT_{390}$-mGM-CSF in a dose dependent manner. Without addition of anti-mGM-CSF antibodies, $DT_{390}$-mGM-CSF at a concentration of $1\times10^{-9}$ M produced a 84% inhibition of protein synthesis of FDCP2.1d. The addition of 1 nM anti-mGM-CSF antibodies partially neutralized this cytotoxic effect. The addition of 10 nM or 100 nM anti-mGM-CSF antibodies completely neutralized this cytotoxic, effect (FIG. 5). The effect of $DT_{390}$-mGM-CSF on two GM-CSF non-responsive cell lines was tested to further examine the specificity of the cytotoxic effect. $DT_{390}$-mGM-CSF did not inhibit the T cell line EL4 or leukemia cell line C1498. These data indicate that $DT_{390}$-mGM-CSF is specifically cytotoxic to cells via the GM-CSF ligand-receptor complex.

The effect of different concentrations of $DT_{390}$-mGM-CSF on the proliferation of WT-19 mouse myelomonocytic leukemia cells (a clone of FDCPI cells) were evaluated. Concentrations of $10^{-6}$M and $10^{-7}$M $DT_{390}$-mGM-CSF produced 100% cell kill after 48 h exposure, while $10^{-8}$M fusion toxin produced 42% cell kill. Similar concentrations of fusion toxin resulted in 40 to 50% killing of CT-26 mouse colon cancer cells after 48 h exposure, but no killing of LS174T human colon cancer cells. These results demonstrate that the fusion toxin was cytotoxic to both mouse leukemia and colon cancer cells. Even higher cytotoxicity against CT-26 cells should result once they are transduced with the high affinity GM-CSF β receptor.

The $DT_{390}$-mGM-CSF fusion toxin has been radiolabeled with $^{125}$I. Four hundred μl (69 μg) fusion toxin was labeled with 1 mCi $^{125}$I using the iodogen method (316) and purified on a Sephadex G-25 column.

The final product was submitted to a SEC 250 column and showed 560 μCi of radioactivity in a single peak. The $^{125}$I-labeled $DT_{390}$-mGM-CSF was tested in an in vitro live cell binding assay for binding to WT-19 mouse myelomonocytic leukemia cells. There were $6.3\times10^{3}$ molecules of $DT_{390}$-mGM-CSF bound/cell, and the binding was inhibited to background levels in the presence of excess unlabeled $DT_{390}$-mGM-CSF or mGM-CSF. The fusion toxin did not bind to murine CT-26 colon cancer cells or human LS174T colon cancer cells. It is known that the α subunit binds GM-CSF with low affinity (256), whereas the β portion of the receptor does not directly bind the cytokine but forms high affinity receptors with α subunits (257).

Several desirable features of mGM-CSF receptor-RFT systems are envisioned. Xenogeneic RFT offers the potential to achieve a specific interaction with the corresponding xenogeneic receptor. In this context, a lack of cross-reactivity with the endogenous, human GM-CSF receptor-ligand system is an asset. Thus, non-tumor localization of RFT at these sites would not have deleterious clinical sequela since this RFT would not bind to human GM-CSF receptors present in bone marrow. For a purely xenogeneic system, the murine GM-CSF receptor is used. The murine GM-CSF receptor possesses an extremely high affinity for its cognate ligand, GM-CSF. In addition, the human and murine GM-CSF receptor-ligand systems exhibit absolutely no cross-reactivity.

Construction, expression, and purification of murine IL-4-DT fusion toxin and testing of cytotoxic activity Oligonucleotides were synthesized using cyanomethyl phosphoramidite chemistry on an Applied Biosystems model 380 A DNA synthesizer and purified by chromatography on Oligonucleotide Purification Cartridges (Applied Biosystems, Inc., Foster City, Calif.) as recommended by the manufacturer. Purified oligonucleotides were resuspended in TE buffer (10 mM Tris base, 1 mM EDTA, pH 8.0). The sequences of oligonucleotides used in this study are listed in Table 1. The hybrid gene encoding $DT_{390}$-mIL-4 was constructed by the method of gene splicing by overlap extension (SOE) and ligated into the pET21d plasmid (Novagen, Madison, Wis.). A DT gene fragment was generated in the first polymerase chain reaction by using a plasmid, containing the coding sequence for the DT mutant CRM 107 as a template with primers ‘a’ and ‘b’. Primer ‘a’ introduced an Nco I restriction site and an ATG initiation codon 5' to the DT coding sequence. Primer ‘b’ created a region of homology with the first six amino acids of the mature mIL-4 gene and placed them directly after the 389th amino acid of DT. An IL-4 fragment was generated in a second PCR reaction. A plasmid containing the cDNA of mIL-4 was used as a template with primers ‘c’ and ‘d’. Primer ‘c’ introduced a region of sequence homology with amino acids 384 to 389 of DT and placed it 5' to the coding sequence for the mature mIL-4 gene. Primer ‘d’ generated a Xho I restriction site at the end of the IL-4 molecule. The 1196 b.p. DT fragment and the 389 b.p. IL-4 fragment generated in the PCRs described above were then purified and used as templates in a SOE reaction using primers ‘a’ and ‘d’. This SOE formed the full length 1549 b.p. $DT_{390}$-mIL-4 hybrid gene. The $DT_{390}$-mIL-4 hybrid gene was digested with Nco I and Xho I and ligated into the Nco I and Xho I cloning sites in the pET21d plasmid. Using the Xho I cloning site placed the hybrid gene in frame with the 6X HIS residues present in the pET21d plasmid. The assembly of plasmid pDTIL-4 is shown in FIG. 16.

Plasmid, pDTIL-4, was transformed into the *Escherichia coli* strain BL21(DE3) (Novagen, Madison, Wis.) and protein expression was evaluated. Briefly, recombinant bacteria were grown in 500 ml Luria broth, supplemented with 100 mg/ml carbenicillin (Sigma, St. Louis, Mo.), in a 2 L flask at 37° C. When the absorbance ($A_{600}$) of culture reached 0.6, expression of the hybrid gene was induced by the addition of isopropyl-b-D-thiogalactopyranoside (IPTG) (Gibco BRL, Gaithersburg, Md.). Three hours after induction, the bacteria were harvested by centrifugation at 5000 g for min. To determine the localization of expressed protein, an aliquot of bacterial pellet was resuspended in 30 mM Tris, pH 7.5, 20% sucrose, 1 mM EDTA and osmotically shocked by placing in ice cold 5 mM $MgSO_4$. The periplasmic fraction (supernatant) was obtained by centrifugation at 8000 g for 10 min. Another aliquot of bacterial pellet was resuspended in sonication buffer (50 mM Sodium Phosphate, pH 7.8, 300 mM NaCl). After incubation at −20° C. for 16 hours, the resuspended sample was sonicated for minutes. The spheroplast fraction (pellet) and cytosolic fraction (supernatant) were collected separately by centrifugation at 10,000 g for minutes.

Crude, as well as purified fusion proteins were analyzed or sodium dodecyl sulfate polyacrylamide gel electrophoresis (SDS-PAGE). SDS-PAGE was performed using 4–20% gradient gels (Bio-Rad, Richmond., CA) and a Mini-Protein II gel apparatus (Bio-Rad, Richmond, Calif.). Proteins were stained with Coomassie brilliant blue. For immunoblotting, electrophoresed proteins were transferred to nitrocellulose membranes.

Membranes were blocked with 3% gelatin-containing TBS (20 mM Tris, 500 mM NaCl, pH 7.5) and washed with TTBS (TBS, 0.05% Tween-20, pH 7.5). Horse anti-DT antisera (Connaught Lab, Switwater, Pa.) and anti-IL-4 (a rat IgG monoclonal antibody 11B11 from ATCC) were used as a source of primary antibodies. The blots were processed using horseradish peroxidase conjugated protein-G (Protein G-HRP) and developed using HRP color reagents (Bio-Rad, Richmond, Calif.).

To isolate expressed protein from inclusion bodies, a bacterial pellet was resuspended in TE buffer (50 mM Tris, pH 8.0, 20 mM EDTA, 100 mM NaCl) and treated with 5 mg/ml lysozyme for 30 minutes. The pellet was then incubated in Triton X-100 buffer (11% v/v Triton X-100, 89% v/v TE) for 30 minutes at room temperature after briefly homogenizing with a tissuemizer (Thomas Scientifics, Germany). Inclusion bodies were collected by centrifugation at 24,000 g for 50 min. Solubilization of the inclusion body pellet was achieved in the presence of strong denaturants and reducing agents in a buffer consisting of 7 M guanidine, 0.1 M Tris, pH 8.0, 2 mM EDTA, and 65 mM dithioerythrito (DTE). The solution was incubated at room temperature for 16 hours. To remove insoluble material, the solution was centrifuged at 40,000 g for 10 min. Protein concentrations were determined according to Bradford method. To ensure proper tertiary folding, renaturation was initiated by a rapid 100-fold dilution of the denatured and reduced protein into refolding buffer consisting of 0.1 M Tris, pH 8.0, 0.5 M L-arginine, 0.9 mM oxidized glutathione (GSSG), and 2 mM EDTA. The samples were incubated at 10° C. for 48 hours. The refolded protein was diafiltrated and ultrafiltrated against 20 mM Tris, pH 7.8 using a spiral membrane ultrafiltration cartridge on Amicon's CH2 system (Amicon, Beverly, Mass.). Samples were loaded on a Q- Sepharose (Sigma, St. Louis, Mo.) column and eluted with 0.3 M NaCl in 20 mM Tris, pH 7.8. The protein was diluted five-fold and subsequently applied to another Q- Sepharose column and eluted with a linear salt gradient form 0 to 0.4 M NaCl in 20 mM Tris, pH 7.8. The main peak from the second Q-Sepharose column was purified by size-exclusion chromatography on a TSK 250 column (TosoHaas, Philadelphia, Pa.).

Figure 20:
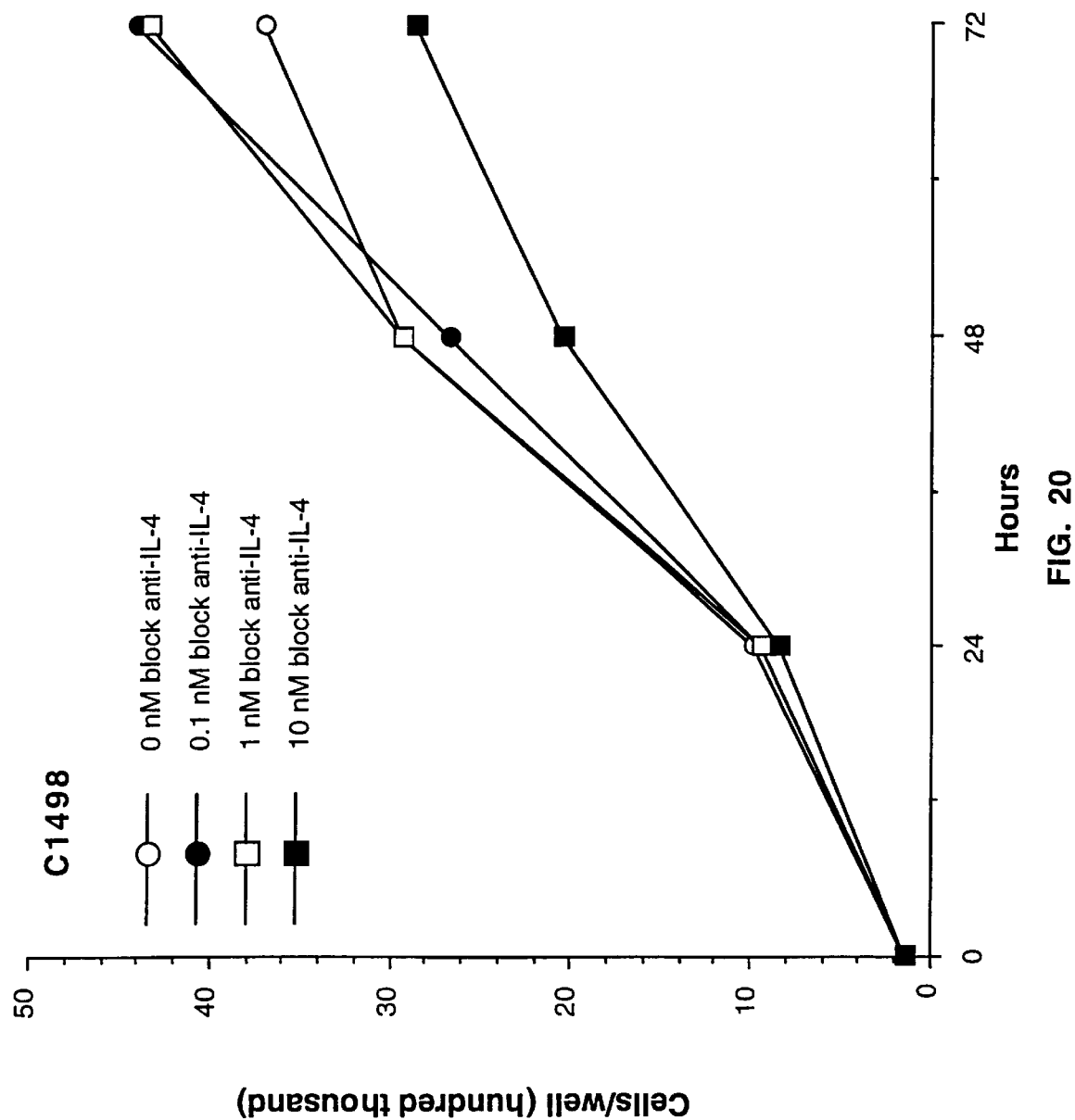
FIG. 20 shows blocking of cell proliferation inhibition activity of DT$_{390}$-mIL-4 fusion toxin on C1498 cells (shown in FIG. 19) by the addition of 11B11 rat anti-mIL-4 antibody before addition to cells.

The toxin was nicked by treating 15 mg of $DT_{390}$-mIL-4 with 0.04 mg of trypsin for 15 min at 37° C. The reaction was stopped with soybean inhibitor. Duplicate samples of nicked DT and DT390-IL-4 were examined for their ADP ribosyl transferase activity as previously described (Johnson et al., *J Biol Chem* 1988; 263:1295). Briefly, ADP-ribosylation was carried out in 80 $\mu$l reaction mixtures containing 40 ml of 0.01 M Tris -HCl buffer with 1.0 mM dithiothreitol, pH 8.0, 10 ml of rabbit reticulocyte lysate (containing the elongation factor-2, (EF-2), and 10 ml of toxin sample. The reaction was initiated by the addition of 10 ml of 0.57 mM [$^{32}$p] nicotinamide adenine dinucleotide (ICN Biomedicals, Irvine, Calif.). Reaction mixtures were incubated at room temperature for 1 hour and the reaction was stopped by the addition of 1 ml 10% trichloroacetic acid (TCA). The precipitate was collected by centrifugation and washed with 1 ml 10% TCA. The radioactivity was counted by standard scintillation techniques. The $DT_{390}$-IL-4 fusion toxin was cytotoxic in the ADP ribosylation assay (FIG. 17).

To characterize the cytotoxic activity of $DT_{390}$-mIL-4, the murine mastocytoma cell line P815 (American Type Culture Collection, Rockville, Md.) was used. Cultured P815 cells were maintained in complete culture media consisting of DMEM supplemented with 10% fetal bovine serum, 1% sodium pyruvate, 1.5% L-glutamine, 2% penicillin/streptomycin, 2% HEPES, 0.8% L-arginine, 2% folic acid and L-asparagine. The cytotoxic activity was assayed by measuring the ability of $DT_{390}$-mIL-4 to inhibit the proliferation of P815 cells. Cells were initially washed twice with plain DMEM followed by a 1 hour incubation at 37° C. A third wash was performed and the cells were resuspended. Cells were seeded at a concentration of $9\times10^4$ cells per tube in complete culture media and treated with the following toxins, $DT_{390}$-hIL-2 and $DT_{390}$-mIL-4, and ricin at concentrations ranging from 1×10–13 M to 1×10–8 M. The cells were treated for 4 hours at 37° C. in a 5% $CO_2$ atmosphere. Following incubation, the tubes were centrifuged for 10 min at 300 g and the supernatant decanted. The cells were washed with complete media three times and resuspended with 600 ml media after the third wash. Cells were seeded at $1\times10^4$ and $5\times10^4$ cells/well in 96-well flat-bottomed plates in a volume of 200 ml. One mCi [$H^3$]-Thymidine was added into each well. After a 24 hour incubation, the cells were harvested on glass fiber filters. Filters were washed, dried, and counted according to standard methods suggested by manufacturer. Cells cultured with media alone served as the control. $DT_{390}$-mIL-4 inhibited cell proliferation in a dose dependent manner. Excess 11B11 anti-IL-4 antibody blocked the cytotoxicity of the mIL-4 fusion toxin (FIG. 18).

To further characterize the cytotoxic activity of $DT_{390}$-mIL-4, a cell proliferation inhibition assay was devised using the C1498 mouse myeloid leukemia cell line (mIL-4 receptor positive) and the EL4 mouse T cell leukemia cell line as a negative control (mIL-4 receptor negative). The cytotoxicity was evaluated by measuring a reduction in viable cells/well. The ability of various concentrations of $DT_{390}$-mIL-4 to inhibit cell proliferation of C1498 cells was examined. C1498 cells were killed by $DT_{390}$-mIL-4 in a dose dependent manner (FIG. 19). To determine if the cytotoxicity of $DT_{390}$-mIL-4 on C1498 cells was mediated by the binding of the mIL-4 moiety, excess anti-mIL-4 receptor antibody (300 mg/ml) was added to the wells which completely neutralized the cytotoxic effect of $DT_{390}$-mIL-4 (FIG. 20). The effect of $DT_{390}$-mIL-4 on a mIL-4 receptor negative cell line (EL4) was tested to further examine the specificity of the cytotoxic effect. $DT_{390}$-mIL-4 did not inhibit the proliferation of the T cell line EL4 (FIG. 21). These data indicate that $DT_{390}$-mIL-4 is specifically cytotoxic to cells via the IL-4 ligand receptor complex.

The $DT_{390}$-mIL-4 fusion toxin, mIL-4, and CDw124 rat anti-mouse IL-4 receptor monoclonal antibody (Genzyme) were radiolabeled with $^{125}I$. Three hundred ml (300 mg) fusion toxin was labeled with 1.4 mCi $^{125}I$ using the iodogen method (316) and purified on an AG 1-X8 resin, chloride (100–200 mesh size) ion exchange column (Bio-Rad, Hercules, Calif.). The final product showed 747 mCi of radioactivity in a single peak. The $^{125}I$-labeled $DT_{390}$-mIL-4, IL-4, and CDw124 were tested in an in vitro-live cell binding assay for binding to P815 mouse mastocytoma cells (mIL-4 receptor positive) and MCA-106 mouse lymphoma cells (mIL-4 receptor positive). There was binding of each of these radioligands to P815 cells and MCA-106 cells, which was blocked by excess (10 mg) cold CDw124 antibody (FIG. 22).

For a purely xenogeneic system, the murine IL-4 receptor (mIL-4r) would be appropriate. It has been shown that the mIL-4-r possesses an extremely high affinity for its cognate ligand, IL-4. In addition, the human and murine IL-4 receptor-ligand systems exhibit absolutely no cross-reactivity. In this regard, the IL-4 ligand-receptor system is the only known interleukin whereby there is no human-murine cross-reactivity. Mosley et al. have cloned this receptor cDNA and expressed it in heterologous COS-7 cells. Expression of the IL-4 clone in COS-7 cells resulted in an IL-4 binding protein indistinguishable from the natural receptor at its normal levels. The binding of $^{125}I$-IL-4 to theses transduced cells exhibited a $K_a$ of $10^9$–$10^{10}$ $M^{-1}$. Puri has described the expression of IL-4r on various tumor cells determined by $^{125}I$-IL-4 binding. Importantly, the murine ligand does not exhibit binding to the human receptor while the human IL-4 does not exhibit binding to the murine receptor. Thus, the murine IL-4 receptor meets the criteria for a useful xenogeneic receptor. Murine IL-4 is a glycoprotein with an approximate molecular weight of 19 kD and contains six cysteines. These cysteines are all involved in intrachain bonds, which will cause the loss of biologic activity if they are reduced. Therefore, care must be taken when radiolabeling this ligand.

In vivo gene transfer into tumor cells

A variety of vector systems were evaluated to achieve in situ transduction of human breast cancer xenografts established subcutaneously in athymic nude mice (FIG. 23). Heterologous gene expression is accomplished in tumor cells by the method of direct in vivo transduction. Efficacious gene transfer method uses recombinant adenoviruses. This method of gene transfer offers advantages and its utility herein is explored.

In addition to the AdpL system, a number of vector systems for transduction of desired genes including adenoviruses, liposomes, RNA, and nucleic acids which have been introduced into clinical trials (255,315,341–345) are known. This technical capacity is demonstrated by the derivation of a recombinant adenoviral vector encoding the human carcinoembryonic antigen (CEA) gene (FIG. 25). To demonstrate utility, the gene transfer capacity of the CEA-encoding recombinant adenovirus was evaluated by transduction of CEA-negative murine colon carcinoma cells (FIG. 26).

For in vivo experiments to demonstrate the anti-tumor efficacy of the approach of genetically induced binding of radioligands, two human tumor xenograft systems are employed, i.e., the mouse colon cancer cell line CT-26 genetically transduced to express mGM-CSF and the human colon cell line LS174T as intraperitoneal transplants in mice.

In vivo gene transfer of mIL-4 receptor into tumor cells

The adenovirus expressing mIL-4 receptor (mIL-4r) was prepared employing the standard two plasmid homologous recombination technique of Graham (Graham FL, Prevec L., Manipulation of adenovirus vectors. In: Murray EJ ed. *Methods in Molecular Biology*, Vol. 7: Gene Transfer and Expression Protocols. Clifton, N.J.: The Humana Press, Inc., 1991:109–128 and Becker et al., *Meth Cell Biol* 1994; 43:161–189). Briefly, a DNA fragment containing the mIL-4r gene (provided by B. Mosley, Immunex Corp., Seattle, Wash.) was subcloned into the polylinker of the adenoviral shuttle vector pACCMVpLpARS (+) (provided by R. Gerard, Katholieke Universiteit Leuven, Leuven, Belgium). This plasmid provides promoter/initiation signals derived from the CMV early promoter/enhancer and polyadenylation signals from SV40. The resulting recombinant adenovirus shuttle plasmid pAC-mIL-4r was employed to derive an E1-deleted, replication-incompetent, recombinant adenovirus employing standard methodologies. Briefly, the shuttle plasmid and the adenoviral packaging plasmid pJM17 (provided by F. Graham, McMaster University, Hamilton, Ontario, Canada) were co-transfected into the E1A transcomplementing cell line 293 employing the commercial cationic liposome vector DOTAP (Life Technologies, Inc., Grand Island, N.Y.). Transfected cells were maintained until the onset of cellular cytopathic effects. The newly generated recombinant adenovirus was plaque purified three times. The recombinant adenovirus encoding the mIL-4r gene, AdCMVmIL-4r, was expanded within 293 cells and purified by CsCl gradient centrifugation. Genomic DNA derived from the recombinant adenovirus was subjected to digestion with various restriction endonucleases and analyzed by agarose gel electrophoresis. Wild-type adenovirus WT300 (provided by T. Shenk, Princeton University, Princeton, N.J.) was employed as a control for analysis of genomic DNA derived from AdCMVGRPr. Adenoviral vectors were titered within the cell line 293, employing plaque assay techniques for direct determination of viral pfu.

A427 human non-small cell lung cancer cells were infected with an adenovirus expressing mIL-4 receptor that was produced under control of the CMV promoter (AdIL-4r) at 10 plaque forming units (pfu)/cell for 2 days, and then tested for binding of radioligands. All 3 radioligands ($^{125}I$-labeled $DT_{390}$-mIL-4, mIL-4, and CDw124) showed greater binding to infected cells than control uninfected cells, which was blocked by excess unlabeled CDw124 antibody (FIG. 23). The results of the infection of LS174T and WiDr human and MC-38 mouse colon cancer cells with AdIL-4r at 10, 100, and 200 pfu/cell and binding 2 days later with 2 of the radioligands, which was blocked with excess unlabeled antibody, are shown in FIG. 24. Thus, the induction of mIL-4 receptor expression in several human tumor cell lines was at levels higher than control positive cell lines.

It was next determined whether the $DT_{390}$-mIL-4 fusion toxin at varying dilutions was cytotoxic to mIL-4 receptor transduced cells. The unlabeled $DT_{390}$-IL-4 showed a dose response effect with regard to growth inhibition of AdIL-4r infected (10 pfu/cell) A427 cells and noninfected P815 and MCA-106 cells, as compared to untreated control cells, at 1–3 days after exposure to fusion toxin (FIG. 25). This study was repeated following infection of LS174T cells with different pfu/cell, and there was a dose response relationship as shown in FIG. 26. These studies were repeated using P815 cells with $^{125}$I-labeled $DT_{390}$-mIL-4 fusion toxin and mIL-4 with similar cytotoxic results as shown in FIG. 27. The $DT_{390}$-mIL-4 fusion toxin (100 mg) was added to 200 mCi 125j-iodophenyl-N-hydroxysuccinimide ($^{125}$I-mIPNHS) residue prepared as described previously and incubated at room temperature for 2 hours.

After incubation, the mixture was purified on a Sephadex PD-10 column in 37% overall radiochemical yield. The $^{125}$I-mIP-$DT_{390}$-mIL-4 inhibited cellular proliferation of P815 cells in a dose dependent manner similar to that of unlabeled $DT_{390}$-mIL-4. Thus, the cytotoxic activity of the fusion toxin was preserved following radiolabeling.

```
Primers used to generate DT390-mIL-4 fusion protein (SEQ ID NO:2)

a            NcoI    DT...

5'      AGATATACCATGGGCGCTGATGATGTTGTTGAT start (SEQ ID NO:3)

b       IL-4              DT 389 388 387 ...

5'      GTCGCATCCGTGGATATGAAATGGTTGCGTTTTATG (SEQ ID NO:4)

c       DT                IL-4

384 385...

5'      CATAAAACGCAACCATTTCATATCCACGGATGCGAC (SEQ ID NO:5)

d            XhoI   IL-4...

5'      GCCGTACTCGAGCGAGTAATCCATTTG

Nco I        Met                         Xho I
                DT                          IL-4
```

Figure 9:
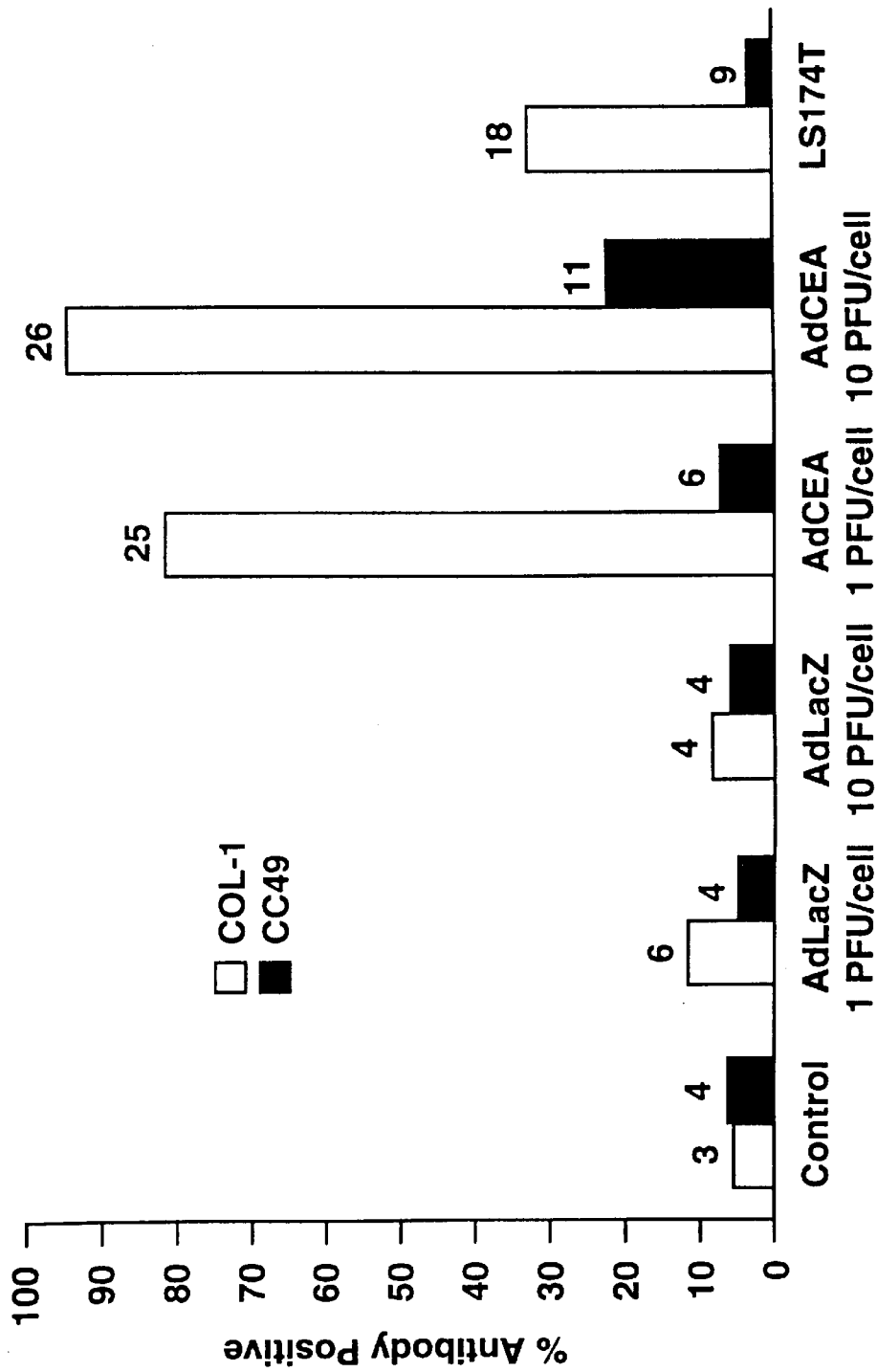
FIG. 9 shows the reactivity of MoAbs COL-1 or CC49 with D54 MG cells transduced with 1 or 10 PFU/cell of AdCMVCEA or AdCMVLacZ was determined by flow cytometry using fluorescein-conjugated goat anti-mouse IgG antibody. The mean percentage positive: cells is depicted by the bars and the mean fluorescence for the populations is given above the bars. For comparison, CEA-expressing LS174T colon carcinoma cells were similarly immunostained and analyzed.

The extent to which D54 MG cells could be induced by adenoviral mediated gene transfer to express cell surface CEA was analyzed by flow cytometry (266). D54 MG cells were transfected with 1, 10, 100, or 1,000 PFU/cell of AdCMVCEA. D54 MG cells transfected with AdCMVLacZ at 1 or 10 PFU/cell served as negative controls. Two-days post-transfection cell membrane-associated CEA was assayed with anti-CEA MoAb COL-1 or with CC49, a negative control antibody. The LS174T human adenocarcinoma cells, known to constitutively express CEA, were utilized as a positive control cell line. As shown in FIG. 9 there was a considerable, increase in CEA positive D54 MG cells following AdCMVCEA transduction. Compared with the AdCMVLacZ transduced cells which were 5–11% positive. for CEA by FACS, 82–95% of D54 MG cells infected with the AdCMVCEA construct were strongly positive even at the lowest MOI used (1 PFU/cell). Lower MOIs were not studied. At the lower viral particle numbers (e.g., 1 PFU/cell), cell viability remained high (>90%) but as the MOI was increased to 10 PFU/cell, cell viabilities fell (<90%). In comparison with the native expression of CEA on the human colon carcinoma cell line LS174T, AdCMVCEA transduced glioma cells expressed a higher level of CEA (mean fluorescence intensity=24.9 vs. 17.6 for LS174T, FIG. 9) and a greater proportion of the glioma cell population (81.8%) was judged positive compared with the LS174T cells (32.8%).

CEA expression was demonstrated by immunohistochemistry of AdCMVCEA transduced D54 MG cells (1 PFU/cell) maintained in culture which showed a strong specific reaction for the MoAb COL-1. By comparison, D54 MG cells transduced with AdCMVLacZ (1 PFU/cell) or uninfected showed no specific reaction with COL-1 MoAb.

Figure 10:
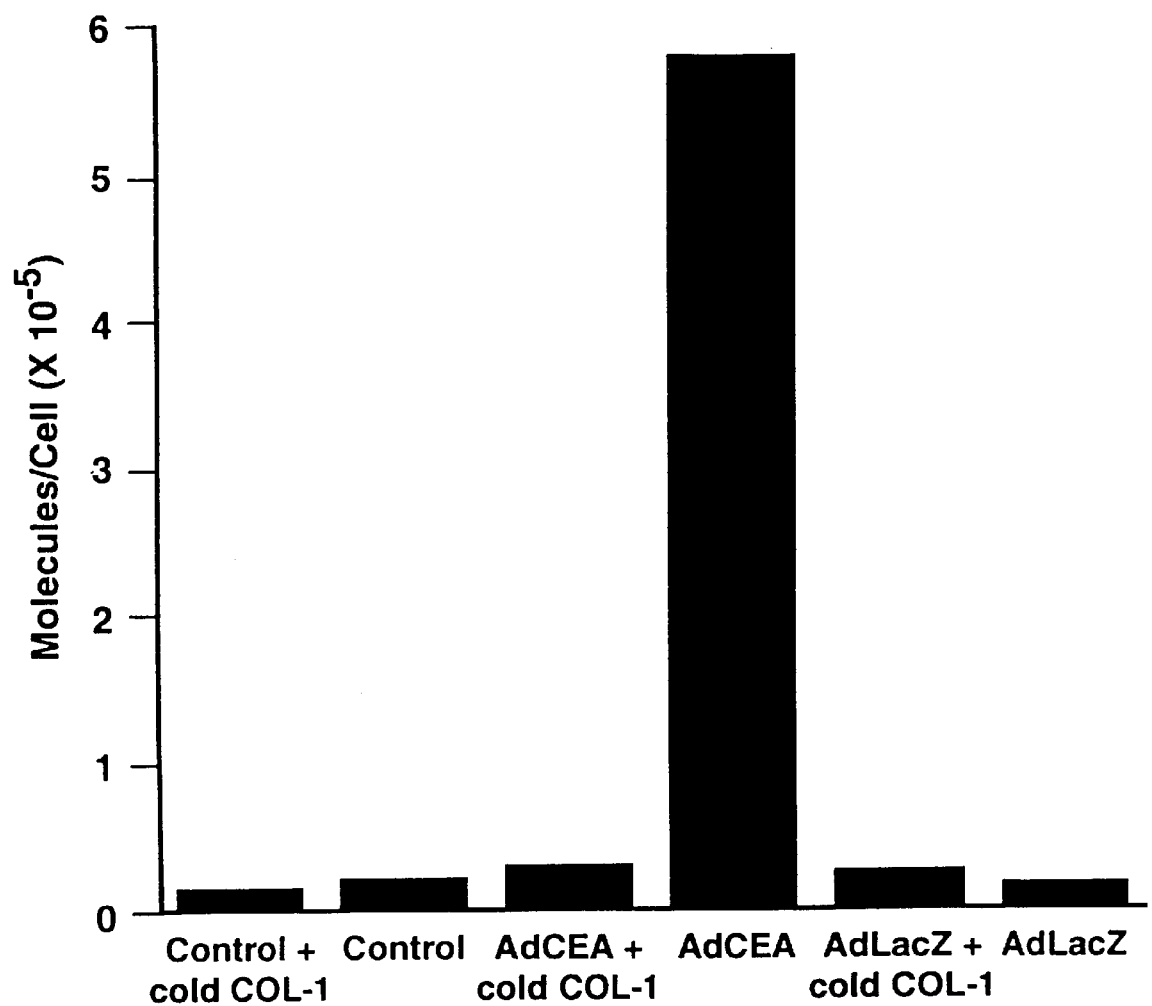
FIG. 10 shows an analysis of binding activity of $^{125}$I-labeled COL-1 MoAb to AdCMVCEA transduced D54 MG cells. D54 MG cells were transfected with 1 PFU/cell and assayed 48 hours post-transfection. Both control virus (AdCMVLacZ) and control antibody (CC49) as well as non-transduced D54 MG cells were analyzed in comparison. The bars depict the molecules of COL-1 bound/cell for a representative experiment run in duplicate. Nonspecific binding of $^{125}$I-labeled COL-1 antibody was measured in the presence of excess unlabeled COL-1 antibody.
Figure 11:
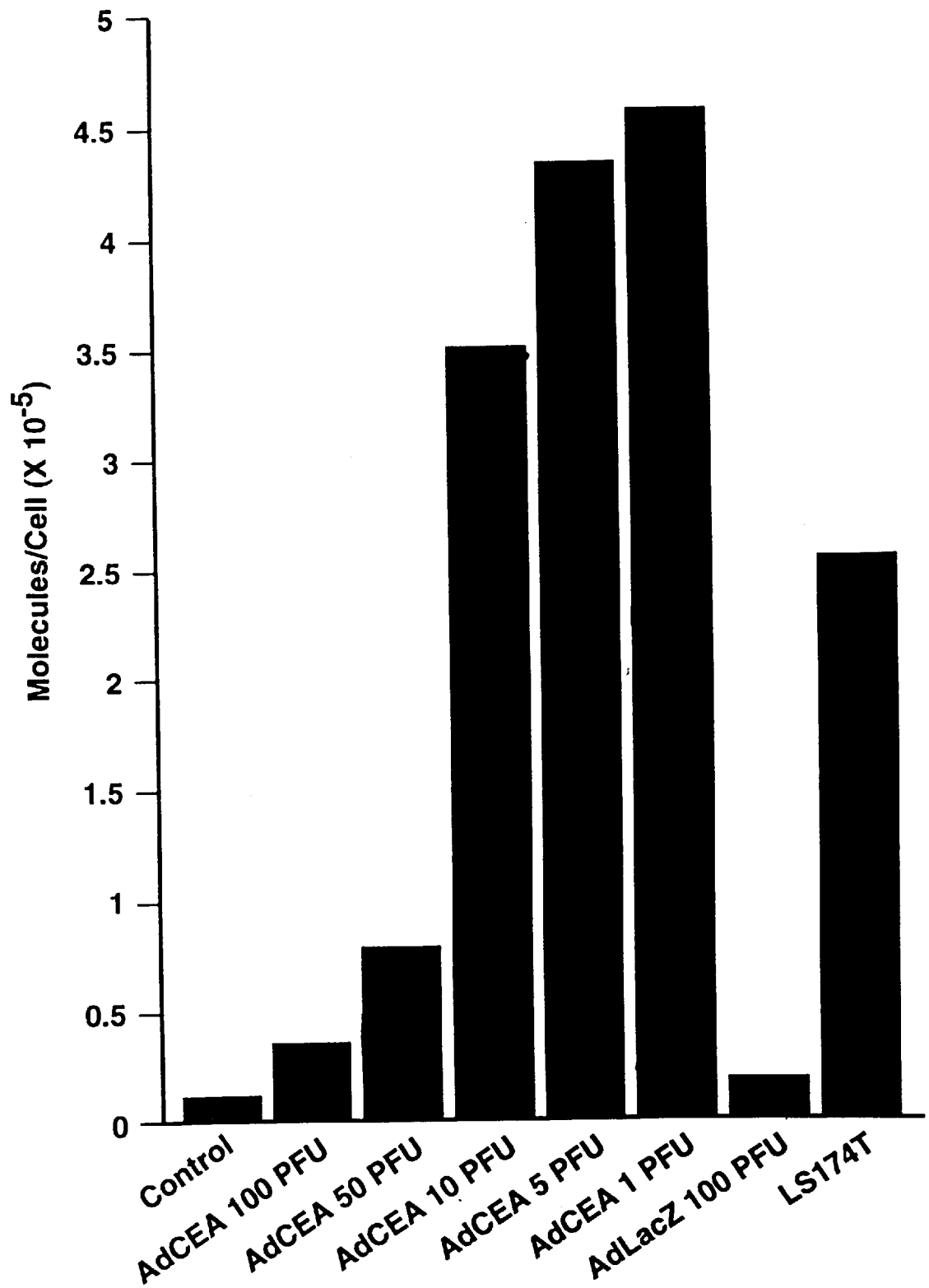
FIG. 11 shows an analysis of binding activity of $^{125}$I-labeled CoL-1 MoAb to D54 MG cells transfected with different particle rs ranging from 1 to 100 PFU/cell. Non-transduced D54 MG cells as well as LS174T cells constitutively expressing CEA were analyzed in comparison. The bars depict molecules of COL-1 bound/cell in duplicate samples. Nonspecific binding of $^{125}$I-labeled COL-1 antibody was measured in the presence of excess unlabeled COL-1 antibody.

Experiments were then conducted using an in vitro live cell radiolabeled antibody binding assay to quantify the level of CEA expression in AdCMVCEA transduced D54 MG cells. These results indicated high binding efficiency of $^{125}$I-labeled COL-1 anti-CEA MoAb to D54 MG cells that had been transduced to express CEA (FIG. 10). The number of molecules of CEA expressed on the cell surface membrane was calculated to be $5.8 \times 10^5$ molecules/cell. Unlabeled COL-1 antibody inhibited 125I-labeled COL-1 antibody binding to D54 MG cells transfected with AdCMVCEA to the level of nonspecific background binding (FIG. 10). Low background binding was seen with $^{125}$I-labeled CC49 control anti-TAG-72 MoAb and in the non-transfected D54 MG and AdCMVLacZ transfected D54 MG controls. In addition, the efficiency of radiolabeled COL-1 binding to AdCMVCEA transduced D54 MG cells was evaluated at 1, 5, 10, 50, and 100 PFU/cell. D54 MG cells transduced with AdCMVLacZ were used as negative controls and compared to LS174T human colon adenocarcinoma cells known to constitutively express CEA. Optimal expression of CEA, as measured by radiolabeled binding, was seen in D54 MG cells transfected with either 1 or 5 PFU/cell (FIG. 11). Furthermore, the number of molecules of CEA expressed on the cell surface of transfected D54 MG cells from six experiments with 1 PFU/cell at 48 h post-transfection ($4.7 \pm 0.5 \times 10_5$, n=20) was considerably higher than in the CEA positive LS174T cells ($2.7 \pm 0.5 \times 10^5$, n=10) (P<0.01), confirming our earlier FACS results. The COL-1 antibody did not internalize explaining the lack of cytotoxic activity of COL-1 IT.

Figure 12:
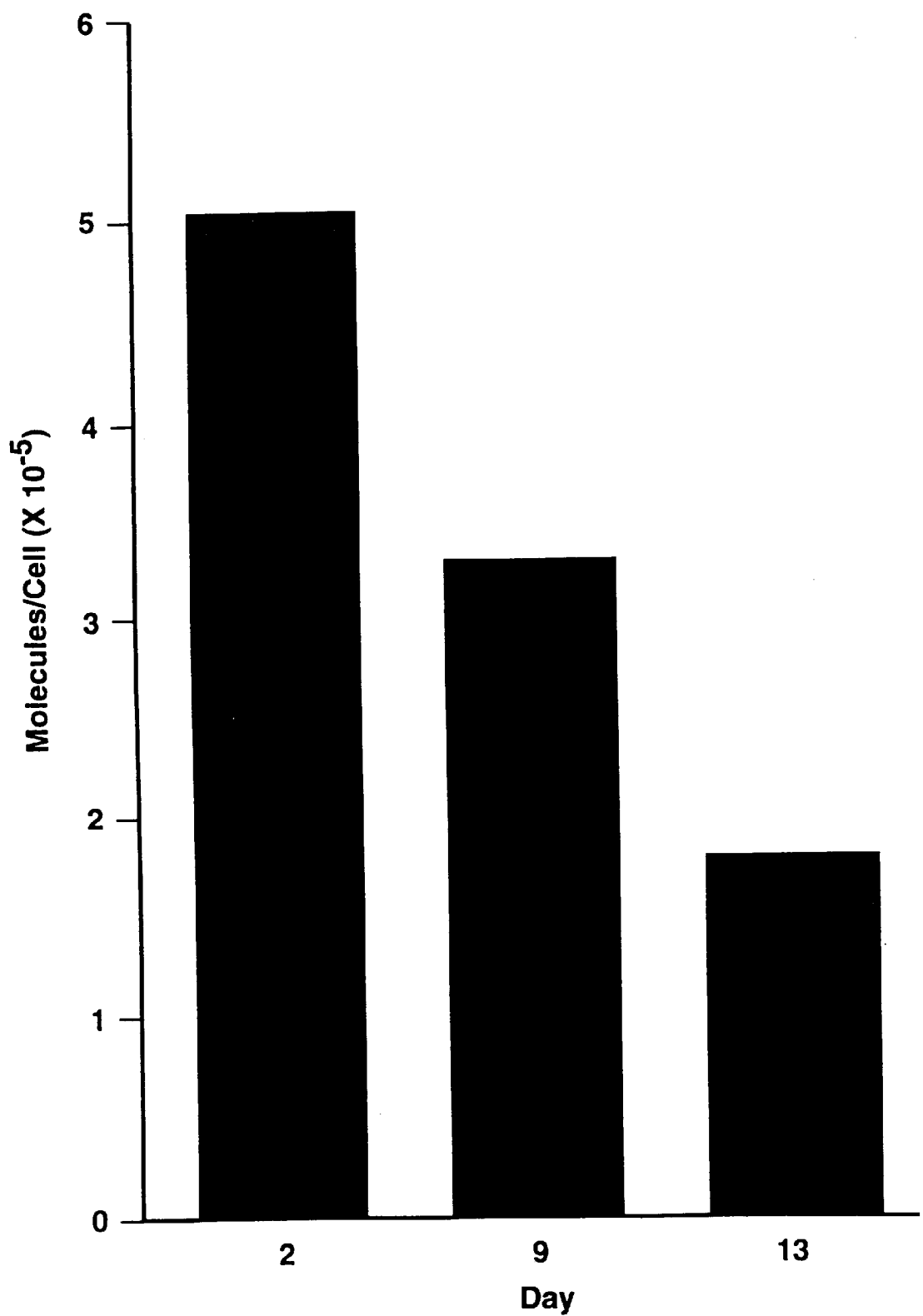
FIG. 12 shows an analysis of binding activity of $^{125}$I-labeled COL-1 MoAb to AdCMVCEA transduced D54 MG cells assayed at varying days post-transfection. The bars depit the molecules of COL-1 bound/cell at 2, 9, and 13 days post-transfection in duplicate samples.

Since recombinant adenoviral infection is known to allow for only transient levels of heterologous gene expression, persistence of cell surface CEA expression in AdCMVCEA transduced D54 MG cells was determined. Radiolabeled binding assays were performed at 2, 9, and 13 days post-transfection with AdCMVCEA at 1 PFU/cell. $^{131}$I-labeled COL-1 binding to CEA transduced cells was found to be $5.1 \times 10^5$ molecules/cell 2 days post-transfection decreasing 3-fold to $1.8 \times 10^5$ molecules/cell 13 days post-transfection (FIG. 12). Thus, even at 2 weeks post-transfection substantial levels of CEA expression could be detected.

Experiments were designed to evaluate the efficiency of AdCMVCEA transduction of D54 MG xenografts via intratumoral injections and immunohistochemical analysis of CEA expression. Paraffin fixed sections of AdCMVCEA transduced tumors were stained with the anti-CEA MoAb COL-1, and areas of positively stained cells were noted. Positively stained tumor cells varied between each group of mice and among individual tumors within each group. D54 MG tumors that were transduced with 1–3 intratumoral injections of $1 \times 10^7$ PFU AdCMVCEA expressed high numbers of CEA positive tumor cells but there were large areas of the tumors that were not CEA positive. In addition several areas of the same tumor specimen stained positive for CEA. Adjoining skin and stromal tissues did not stain positive for CEA. In contrast the D54 MG tumors that were transduced with 1 PFU AdCMVCEA in vitro expressed only a few small clusters of CEA positive tumor cells (1 to 4 cells) at 13 days after transplantation. Control AdCMVLacZ transduced D54 MG tumors did not stain positive for CEA. These results are consistent with those observed above using immunofluorescence and immunohistochemistry for CEA quantification of cells transduced in vitro and maintained in culture.

In vivo localization of radiolabeled antibody in tumors expressing genetically transduced CEA receptor In vivo tissue distribution of $^{131}$I-labeled COL-1 antibody in athymic nude mice bearing xenografts of D54 MG cells transduced with AdCMVCEA was undertaken to assess the extent of tumor localization.

Biodistributions of 100 or 300 μCi $^{131}$I-labeled COL-1 antibody in athymic nude mice bearing AdCMVCEA transduced D54 MG cells at 4–5 days postinjection are shown in Tables 1 and 2. As a specificity control for localization of $^{131}$I-labeled COL-1 anti-CEA antibody, athymic nude mice bearing AdCMVLacZ transduced D54 MG tumors were used. Athymic nude mice bearing xenografts of LS 174T human colon cancer cells served as a positive control. Radiolabeled COL-1 tumor localization was observed in CEA-transduced D54 MG tumors that were transduced with CEA both in vitro and in situ, as well as in the positive control LS174T tumor xenografts (Table 1). In contrast, no specific tumor localization was seen in the LacZ-transduced D54 MG tumors.

The concentration of COL-1 in in vitro CEA-transduced D54 MG tumors weighing 0.1–1.1 g that received 1 or 2 intratumor injections of 1×10$^9$ PFU AdCMVCEA was 4.8× 5.6%ID/g which was significantly higher at days after intraperitoneal injection in comparison to 1.8±0.7%ID/g with LacZ-transduced D54 MG tumors weighing 0.1–1.4 g (P=0.02). The concentration of COL-1 in LS174T human colon tumors weighing 0.5–1.5 g was 3.7±1.8%ID/g which was similar to that observed in CEA-transduced D54 MG tumors (P=0.35). Radiolabeled COL-1 concentration in blood for the three groups of animals was 5.2±3.0, 6.3±1.8, or 2.2±1.4%ID/g, respectively (Table 3). Blood levels of $^{131}$I-labeled COL-1 in the CEA-transduced D54 MG tumor group were similar to the LacZ-transduced D54 MG tumor group (P=0.38), but the blood level in the CEA-transduced D54 MG group was significantly higher than the LS174T tumor group (P=0.02). This may have been a result of circulating CEA in the LS174T tumor-bearing animals (267) resulting in the formation of $^{131}$I-labeled COL-1-CEA complexes that were rapidly cleared. The concentration of COL-1 in nontransduced D54 MG tumors weighing 0.4–0.6 g that received 1 intratumor injection of 2×10$^7$ PFU AdCMVCEA 2 days before intraperitoneal injection of 100 μCi $^{131}$I-labeled COL-1 was 1.5±0.7%ID/g at 4 days after antibody injection, which was similar to that in nontransduced D54 MG tumors in the same weight range after 1 intratumor injection of 2×10$^7$ PFU AdCMVLacZ (P>0.05) (Table 3). Thus, the highest uptake of COL-1 occurred in in vitro CEA-transduced D54 MG tumors following additional in situ injections of high titer AdCMVCEA.

The tumor/normal tissue (T/NT) uptake ratios from one experiment are shown in Table 4, and ranged from 0.9 to 8.8 in animals bearing CEA-transduced D54 MG tumors (P<0.01) to 1.9 to 11.5 in animals bearing LS174T tumors (P<0.01). Highest ratios were in muscle, bone, and small intestine. In contrast, T/NT uptake ratios in animals bearing LacZ-transduced D54 MG tumors were lower ranging from 0.3 to 2.2 although significant differences did exist among tissues (P<0.01). The differences of T/NT ratios among individual tissues also varied significantly among the three groups (Table 4). To determine the overall difference of T/NT ratios, experimental group means for the nine tissues in each group were calculated and found to be 4.2, 1.4, and 5.3. Significant differences were observed among these mean adjusted T/NT ratios (P<0.05 for all). The tissue specific differences of the T/NT ratios among the three experimental groups were also compared. Except for spleen, significantly lower ratios were observed in the LacZ-transduced D54 MG tumor group compared to the CEA-transduced D54 MG tumor group or the group of animals bearing LS 174T tumors. There were also lower ratios of tumor/blood, tumor/lung, and tumor/liver in the animals bearing CEA-transduced D54 MG tumors compared to the animals bearing LS174T tumors. Thus, the biodistribution of $^{131}$I-labeled COL-1 resulted in similar T/NT uptake ratios in most tissues in animals bearing CEA-transduced D54 MG tumor xenografts as in animals bearing LS174T tumors.

TABLE 3

Biodistribution of $^{131}$I-labeled COL-1 MoAb in tumor-bearing athymic nude mice[a]

| Tissue | % ID/g (mean ± SD) at 4 or 5 days postinjection | |
|---|---|---|
| Blood | 5.2 ± 3.0 | (n = 7) |
| AdCEA D54 MG | 4.8 ± 5.6 | (n = 7) |
| (1 × 10$^9$ PFU AdCEA/tumor) | | |
| Blood | 6.3 ± 1.8 | (n = 11) |
| AdLacZ D54 MG | 1.8 ± 0.7 | (n = 11) |
| (1 × 10$^9$ PFU AdLacZ/tumor) | | |
| Blood | 8.4 ± 3.4 | (n = 4) |
| AdCEA D54 MG | 2.5 ± 0.9 | (n = 4) |
| Blood | 9.5 ± 0.6 | (n = 3) |
| AdLacZ D54 MG | 2.1 ± 0.2 | (n = 3) |
| Blood | 9.3 ± 4.9[b] | (n = 5) |
| D54MG | 1.5 ± 0.7[b] | (n = 5) |
| (2 × 10$^7$ PFU AdCEA/tumor) | | |
| Blood | 9.9 ± 3.0 | (n = 4) |
| D54MG | 1.8 ± 0.9 | (n = 4) |
| (2 × 10$^7$ PFU AdLacZ/tumor) | | |
| Blood | 2.2 ± 1.4 | (n = 11) |
| LS174T | 3.7 ± 1.8 | (n = 11) |

[a]Athymic nude mice bearing in vitro and/or in situ transduced D54 MG tumor xenografts or LS174T colon cancer xenografts were injected intraperitoneally with 100 or 300 μCi $^{131}$I-labeled COL-1 and sacrificed 4 or 5 days after injection.
[b]Sacrificed at 4 days after intraperitoneal injection of $^{131}$I-labeled COL-1.

TABLE 4

Tumor/normal tissue uptake ratios of $^{131}$I-labeled COL-1 MoAb in tumor-bearing athymic nude mice[a]

| | T/NT uptake ratio[b] (mean ± SD) at 5 days postinjection | | |
|---|---|---|---|
| Tissue | AdCEA D54 MG (n = 7) | AdLacZ D54 MG (n = 11) | LS174T (n = 11) |
| Blood | 0.9 ± 0.6[c] | 0.3 ± 0.1 | 1.9 ± 0.6 |
| Lung | 1.6 ± 1.1 | 0.6 ± 0.4 | 2.8 ± 0.9 |
| Liver | 3.5 ± 2.4 | 1.3 ± 1.1 | 5.4 ± 2.2 |
| Small Intestine | 6.4 ± 4.5* | 1.9 ± 0.6 | 8.7 ± 3.8* |
| Spleen | 2.3 ± 1.8* | 1.5 ± 1.9* | 2.0 ± 1.4* |
| Kidney | 4.8 ± 3.7* | 1.8 ± 1.8 | 5.9 ± 2.1* |
| Skin | 3.0 ± 2.0* | 0.8 ± 0.3 | 2.9 ± 1.0* |
| Bone | 6.9 ± 5.8* | 2.0 ± 1.0 | 6.2 ± 3.4* |
| Muscle | 8.8 ± 6.2* | 2.2 ± 1.0 | 11.5 ± 9.3* |

[a]Athymic nude mice bearing in vitro and in situ transduced D54 MG tumor xenografts or LS174T human colon cancer xenografts were injected intraperitoneally with 300 μCI $^{131}$-labeled COL-1 and sacrificed 5 days after injection.
[b]Tumor/normal tissue uptake ratio is the % ID/g of the tumor divided by the % ID/g of the normal tissues.
[c]The T/NT ratios for each tissue were compared among the three groups of animals. They were significantly different (P < 0.05) except for groups that are noted by an asterisk.

Indirect immunofluorescence and flow cytometric analysis of unlabeled MoAbs with human colon cancer cells were performed using fluorescein-conjugated goat anti-mouse IgG. Murine MoAbs COL-1 and 35 (anti-CEA), 17-1A (reactive with a 35–40 kDa gastrointestinal cancer associated antigen), and CC49 reactive with the TAG-72 antigen on adenocarcinomas bound to human colon cancer cell lines LS174T, SW948, and C0112 cells but not to control human melanoma MEL-1 cells (203,204,266).

Radiolabeling of monoclonal antibodies reactive with tumor cell lines

Several radiolabeling techniques have been established for the radionuclides selected. Buchsbaum et al. have radiolabeled anti-carcinoma MoAbs with $^{125}$I and $^{131}$I (203,204), and with $^{111}$In and $^{90}$Y by the bicyclic DTPA anhydride method of Hnatowich (201,202,250,268,269) or with the isothiocyanate derivative of DTPA supplied by Gansow (270,271). MoAb 17-1A was radiolabeled with $^{111}$In using the SCN-Bz-DTPA anhydride supplied by Dr. Otto Gansow at the NCl (270,271). IA radiolabeling efficiency of about 40% was found using a 3:1 molar ratio of anhydride to antibody. Chromatograms obtained by HPLC analysis cf unlabeled and radiolabeled MoAbs and gel electrophoresis results indicated homogeneous preparations of unlabeled and radiolabeled products. The $^{125}$I- and $^{131}$I-labeled products showed minimal (<2%) free iodine in the preparations. With these techniques, the radiolabeled MoAbs retained immunoreactivity as determined by live cell assay, as well as binding to purified antigens (203).

Radiolabeling with $^{99m}$Tc, $^{188}$Re, and $^{186}$Re.

Hydroxamic acids were used as bifunctional chelating agents (B CA) for the radiolabeling of MoAbs with $^{188}$Re or $^{186}$Re. The first compound of the hydroxamate BCAs, trisuccin, (1, FIG. 28) has beena synthesized (217). Hydroxamate compounds with improved properties were synthesized and the synthesis of a new pyridine-derived hydroxamate BCA is now reported (FIG. 29) (273). Labeling of this new ligand system with potentially therapeutic metals and $^{99m}$Tc, and conjugation to mouse polyclonal IgG (MPIgG), are reported below.

Commercially supplied 2,5-dichloro-3-nitropyridine (1, FIG. 29) was converted to compound 2 in a one-pot reaction with thiolacetic acid and then tert-butyl bromoacetate. Reduction of 2 to the corresponding amine 3 and its coupling to 4-nitrophenyl acetic acid afforded intermediate 4. The latter compound was incubated with 96% formic acid to afford the dicarboxylic acid 5 which was then coupled to two equivalents of O-tert-butyl hydroxylamine to form the protected dihydroxamate 6. Catalytic hydrogenation of 6 followed by removal of O-tert-butyl protecting groups with boron trifluoroactetate in trifluoroacetic acid afforded the target compound 8. Another compound 2,6-bis[((N-hydroxyamino)carbonyl) methyl]-5-nitropyridine, 11, was synthesized to study the ligand-metal complexation of the free, non-conjugated ligand. Steps for the synthesis of 11 were similar to those for 8 and are shown in Scheme II. The purpose for synthesizing 11 was elimination of the effect of the free $NH_2$ group of 8 in metal chelation ensuring the pure effect of the hydroxamate moieties.

Metal-Complex Formation Non-radioactive Metals: Compound 11 was used to chelate cold copper, cobalt and lutetium. The chloride salts of all three metals were used since their radioactive isotopes are also supplied as chlorides. The aqueous solutions of these metals were added to that of compound 11 in a 1:4 (v/v) mixture of DMSO and phosphate buffer at a slightly basic pH. The formation of an insoluble precipitate at room temperature was instantaneous. The complexes showed the same colors with copper and cobalt as reported by others (274) and and they formed at more acidic pHs. The lutetium complex had a bright yellow color. All three complexes were of extremely low solubilities in water and organic solvents including DMF, DMSO and TFA. The only solvent which dissolved these compounds was formic acid. Both the mass spectra and colors of these complexes remained unaffected in this solvent, showing a high stability for these complexes.

Radiolabeling of the new pyridine-dihydroxamate and its MPIgG conjugate with technetium-99m With this radiometal, labeling of compound 8 was carried out as, a conjugate to MPIgG, a protein similar to the MoAbs in terms of 3-dimensional structure and molecular weight. MPIgG was used as a model antibody. The ligand was conjugated to the oxidized MPIgG, through the Schiff base chemistry (272). Radiolabeling was performed by the in sited reduction of sodium [$^{99m}$Tc]-pertechnetate with stannous chloride. An unconjugated MPIgG was used as the control. This procedure resulted in about 30% radiolabeling yield compared to the control MPIgG without ligand (<0.05%) as monitored by radio-HPLC. Analytical studies with this conjugate, for the measurement of ligand:antibody ratio showed a ratio of only about 0.4. On the other hand, technetium labeling of the free, unconjugated ligand, reveals>95% binding of the pyridine dihydroxamate to $^{99m}$Tc, as evidenced by ITLC and silica gel TLC. The experiment was carried out under the same conditions as for the conjugate, except for the use of unconjugated ligand. This low level of substitution might be due to the low carbohydrate content of the MPIgG. The low ligand:Ab ratio is improved by increasing one or more of the following variables: concentration of the oxidizing agent $NaIO_4$, concentration of the ligand in the conjugation reaction, the time of incubation for the oxidation reaction, and the time of incubation for the conjugation reaction. A derivative of this ligand, one containing a free carboxylate function, capable of conjugating through active ester chemistries (see trisuccin conjugation), is prepared.

Antibody Conjugation

The MPIgG antibody (500 μl of a 10 mg/ml solution) was dialyzed against 0.1M acetate buffer (pH 4.4). Fifty μl of $NaIO_4$ in water was added to a final concentration of 25 mM in $NaIO_4$. The mixture was incubated in the dark at room temperature for 90 minutes and quenched with 10 μl of ethylene glycol and dialyzed against the same buffer. Two-hundred μl of the solution of the ligand in 0.2M carbonate buffer (pH 7.8) was added. After 25 minutes, 10 μl of a sodium cyanoborohydride solution in water was added to a final concentration of 20 mM. The mixture was dialyzed after 3.5 h against PBS.

A second method of conjugation has been recently developed through active ester chemistries. In this method, compound 5 of FIG. 28 was hydrogenated to liberate the hydroxamic functions. The resulting ligand was stirred with excess ortho nitrophenol (ONP) or N-hydroxysuccimimide (NHS) and an equivalent (relative to the ligand) of DCC in DMF for 24 h. The solids were separated by filtration and the solvent was removed in vacuum. The solid residue was washed with excess dry THF and dried in vacuum. The conjugation reaction was tested by the use of a model peptide (P-448), a 20-mer linear chain, containing three lysine residues. This peptide was used to check the reactivities of the ligand towards lysine amino groups with no possible steric hindrance in a large Ab molecule. When two separate radiolabeling tests ($^{99m}$Tc) of the P-448 conjugate were positive, the conjugation and labeling protocols were extended first to MPIgG and then to MoAb CC49. To the solution of P-448/Ab in PBS (pH 7.4) and at 0° C. was add 50 µl of the ligand solution in DMF to an overall mole ratio of 15:1, L:P-448/Ab. After 1.5 h, the Ab conjugate was passed through a PD-10 column eluted with DPBS. The P-448 conjugate was purified by dialysis.

Both preparations were radiolabeled with $^{99m}$Tc in high yields. The MPIgG and CC49 conjugates have also been labeled with $^{188}$Re. Generator-produced Na[$^{188}$Re]-ReO$_4$ was reduced with SnCl$_2$ and added to the solution of the antibody in PBS (pH 7.2) and the mixture was incubated at 45°–50° C. for 1 hour. Radiolabeling yields of at least 60% were consistently observed based on the purified labeled conjugates. This yield may be significantly improved by labeling with lower-pH buffers to prevent the rapid hydrolysis of the reduced rhenium species. The $^{188}$Re-labeled CC49 conjugate showed an immunoreactivity of 91% by the method of Lindmo.

Reactivity/Stability Studies of Trisuccin towards Rhenium

Concerning the ability of binding of the ligand systems to rhenium, the following experiment was carried out. The methyl ester of trisuccin (Compound 6, FIG. 28, designated as tris-OMe) was used. The choice of this derivative is due to its blocked carboxy terminus by an ester group. This will ensure the lack of participation of the free carboxyl function in the chelation mechanism, thus mimicking a situation encountered when trisuccin is conjugated to the antibodies. The solution of mg of citric acid in 1 ml of metal-free (chelexed) water was deoxygenated under vacuum and purged with argon. Crystalline stannous chloride dihydrate was added and the mixture was kept under argon. The solution of aluminum perrhenate (50 µl, 4 mCi) was deoxygenated under argon and was mixed with 100 µl of the stannous chloride solution and the mixture was heated to 90° C. in a water bath for 1 h. Two mg of the ligand was dissolved in 200 µl of 0.1 M phosphate buffer (pH 7.8), and the solution was deoxygenated. The pH of the rhenium solution, after cooling to room temperature, was raised to pH 6 with addition of 10 µl portions of 2.5 N sodium hydroxide solution. One mCi of the label was added to the ligand solution and the mixture was stirred on a hot plate at 40° C. for 30 minutes.

The labeling reactions were monitored by thin-layer chromatography (TLC). Aluminum-backed silica gel plates (Merck) and 20% ethanol in acetone were chosen for the radiolabeling studies. In this system, unreduced aluminum perrhenate moved with the solvent front while the reduced species remained at the origin. At least 94.6% of the metal was reduced within 1 h. Addition of the ligand to the reduced metal removed the R$_f$=0 species showing a radiolabeling yield of 80%. The labeled lioand mixture was challenged with EDTA, trisodium salt, and NaOH as follows: Forty µl of either a 0.1 M solution of EDTA, or 0.5 M NaOH in chelexed water, were added to 100 µl of water containing 20 µl of $^{186}$Re-tris-OMe solution and the mixture was incubated at room temperature. A control solution was also prepared by duplicating the same procedure except with no ligand. TLC runs were carried out after 30 minutes, 24 h, and 72 h, against the controls and also against the original reduced rhenium solution. The original sample of reduced species, kept under argon and at room temperature, was stable under these conditions for at least 72 h. The EDTA challenge had reduced the activity content of the labeled ligand by about 10% after the 72 h period. The NaOH challenge had no detectable effect on the labeled complex. The EDTA control showed 48.6% of the activity at the origin, which might be due to either EDTA-rhenium complexation or the uncomplexed reduced metal. These results clearly indicate that our reducing procedure with SnCl$_2$ and citric acid is a suitable one to prepare low-valence rhenium species for labeling with a suitable ligand, and the trihydroxamic acid system, trisuccin, is an efficient chelator for this metal.

Ligand:antibody substitution levels

Figure 13:
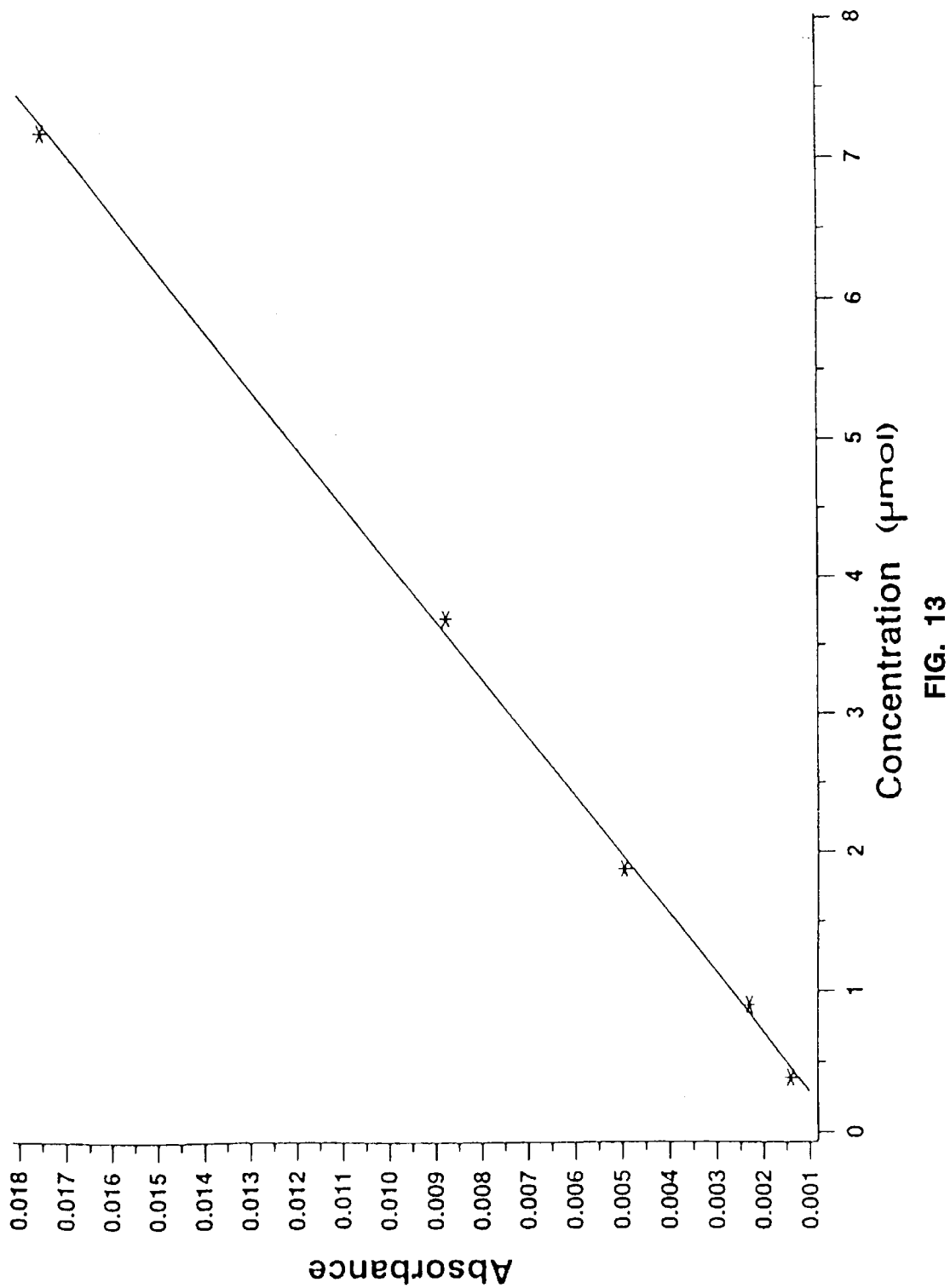
FIG. 13 shows the dependence of the visible (500 nm) absorbance of compound 6-Fe$^{3+}$ on the ligand concentration as a measure of the iron complex formation. Each data point is the average of three independent runs.

The number of ligand molecules per molecule of antibody (L:Ab) was determined using the well-known and highly colored complex of hydroxamates with ferric cation. A 2.5 mM solution of ferric chloride (FeCl$_3$) in water was prepared and used as stock solution. A 400–700 nm visible spectrum of sample (6, FIG. 28) in this solution showed a maximum increase in the absorbance at 500 nm. This wavelength was therefore chosen for the single-wavelength measurements of all samples. To 1 ml of the FeCl$_3$ solution in a sample cuvette were added 5, 10, 20, 40 and 80 µl of a 98.5 µM solution of compound 6 in water and the resulting increases in absorbance were recorded. Data points were collected from three different runs. The absorbances were plotted against molar concentrations of 6 with corrections for each volume increase. The resulting linear plot (R=0.9995, FIG. 13) was used as the standard plot for calculating the L:Ab values. Thus to a fresh sample of the FeCl$_3$ solution was added the ligand-antibody conjugate (20–50 µl) and the absorbance was recorded at 500 nm. The concentration of the protein in each sample had been determined spectrophotometrically at 280 nm (275) in PBS. Using this method L:Ab values of 0.65–1.1 have so far been observed.

Pilot radiolabeling, stability, and biodistribution studies have been done with trisuccin conjugates labeled with $^{186}$Re. The in vivo stability of $^{186}$Re-CC49 was determined by injection of a 100 µCi aliquot i.v. into two NZW rabbits. The rabbits were bled from the other ear and radioactivity was determined in a 1 ml plasma sample. The data indicated that the $^{186}$Re-CC49 had an expected plasma clearance half-life in rabbits. The $^{186}$Re-labeled CC49 conjugate was injected intraperitoneally into athymic nude mice implanted with LS174T human colon cancer xenografts. The animals were then subjected to imaging with a gamma camera. The $^{186}$Re-CC49 had optimal imaging at the third and fourth day. Thus, the trisuccin agent binds $^{186}$Re to an intact MoAb with retention of immunoreactivity and ability to localize to colon cancer xenografts.

The biological effect of either a single injection or 3 injections of 300 µCi of $^{131}$I-labeled 17-1A was assessed. In the first radioimmunotherapy experiments, animals were injected with LS174T tumor cells and when they were 5–11 mm in diameter the mice received either a single intraperitoneal dose of 300 µCi of $^{131}$I-labeled MoAb 17-1A, an equal protein concentration of unlabeled MoAb 17-1A, or no treatment. Injection of $^{131}$I-labeled 17-1A produced a marked decrease in the rate of tumor growth. Tumor regrowth was delayed by approximately 14 days. Another method of expressing the therapeutic effect of $^{131}$I-labeled 17-1A is by an increase in the tumor doubling times. Doubling time increased from 8 days, in the untreated animals, to 15 days after injection with $^{131}$I-labeled 17-1A (195).

In the subsequent radioimmunotherapy experiments, animalls received either 3 injections of 300 µCi of $^{131}$I-labeled 17-1A MoAb (days 9, 16, and 28 after tumor cell injection), unlabeled 17-1A MoAb, or no treatment. Tumor growth was inhibited to a greater degree in the mice that received 3 injections of $^{131}$I-labeled 17-1A MoAb as compared either to the control groups or to the group that received a single injection of $^{131}$I-labeled 17-1A. The rate of tumor growth in the group that received 3 injections did not return to that of the control group during the entire observation period (60 days). The tumor doubling time was estimated Ito be increased to 22 days.

In another tumor growth inhibition experiment, nude mice bearing LS174T colon carcinoma xenografts were injected i.p. with 300 µCi (65.2 µg) of $^{131}$I-labeled human chimeric IgG1 17-1A MoAb, 65.2 µg of unlabeled human chimeric IgG1 17-1A MoAb, or no antibody. At 20 days after $^{131}$I-labeled chimeric IgG1 17-1A MoAb administration, the average tumor size was 133 mm$^2$. In contrast, the average tumor size in the mice receiving unlabeled chimeric IgG1 17-1A MoAb was 531 mm$^2$ and the average tumor size in mice receiving no antibody was 909 mm$^2$. The 131I-labeled chimeric IgG1 17-1A MoAb, following a single i.p. injection of 300 µCi, produced tumor growth inhibition comparable to that of multiple doses of $^{131}$I-labeled murine 17-1A.

$^{125}$I-labeled MoAbs are useful for radioimmunotherapy (278) because of the high LET Auger electrons emitted by $^{125}$I are cytotoxic if the $^{125}$I-labeled MoAb gets into the nucleus (279). The binding of 125I-labeled murine 17-1A to LS174T and SW948 colon cancer cells was investigated in vitro, along with the kinetics of internalization of the 125I into the cells. Using a subsaturating concentration of $^{125}$I-labeled 17-1A, it was found that a much greater percentage of $^{125}$I-labeled 17-1A incubated with cells from 0–72 hours was internalized than was irrelevant control MoAbs. Approximately 44 to 80% of the $^{125}$I-labeled 17-1A bound to cells was internalized, as determined by low pH or trypsin treatment of the cells.

In a recent study (81), the tumor localization and therapy of $^{131}$I- and $^{90}$Y-labeled MoAb 17-1A was compared. The response of nude mice bearing LS174T tumor xenografts to treatment with 131I- or $^{90}$Y-labeled 17-1A MoAb was assessed. Tumor size was calculated as the product of the length times the width, and is expressed as the average for groups of at least eight animals. $^{90}$Yttrium-labeled 17-1A produced tumor growth inhibition. Both tumor growth inhibition and animal lethality were proportional to the quantity of $^{90}$Y-labeled 17-1A administered.

$^{131}$Iodine-labeled 17–1 A decreased LS174T tumor growth in a dose-dependent fashion without lethality. In contrast, the doses of $^{90}$Y -labeled 17-1A which were required to produce a significant increase in tumor doubling time also caused marked toxicity (lethality and hematologic). A 400 µCi injection inhibited tumor growth for the first 19 days. Subsequent growth proceeded at a slower rate than that of untreated tumors. Tumors from the control mice, given no antibody at all, experience rapid growth, and were approximately twice as large as the tumors from the mice injected with 400 µCi 131I-labeled 17-1A MoAb at 12–26 days after antibody injection. Hematological toxicity was evaluated as follows. Fifty µl of peripheral blood was obtained by retroorbital puncture under ether anesthesia on days 9, 20, 27, 36, and 43 after radiolabeled MoAb injection. Leukocyte number was determined using a Coulter counter. Treatment with $^{131}$I- and $^{90}$Y-labeled 17-1A depressed the peripheral. leukocyte counts in a dose dependent manner. The results indicate that 300 and 400 µCi $^{131}$I-labeled 17-1A produced a minor leukopenia relative to untreated control animals at 9 days after injection, which rebounded by day 20. $^{90}$Yttrium-labeled 17-1A reduced the peripheral leukocyte count with approximately the same time course. Counts were decreased at 9 days after injection relative to untreated control animals, and returned to or exceeded normal values at day 20. These studies suggest that $^{131}$I-labeled 17-1A is superior to $^{90}$Y-labeled 17-1A, since $^{131}$I-labeled antibody produced less hematological and animal toxicity and was more effective at inhibiting LS174T tumor growth than $^{90}$Y-labeled antibody across the range of radionuclide doses tested.

Figure 14A:
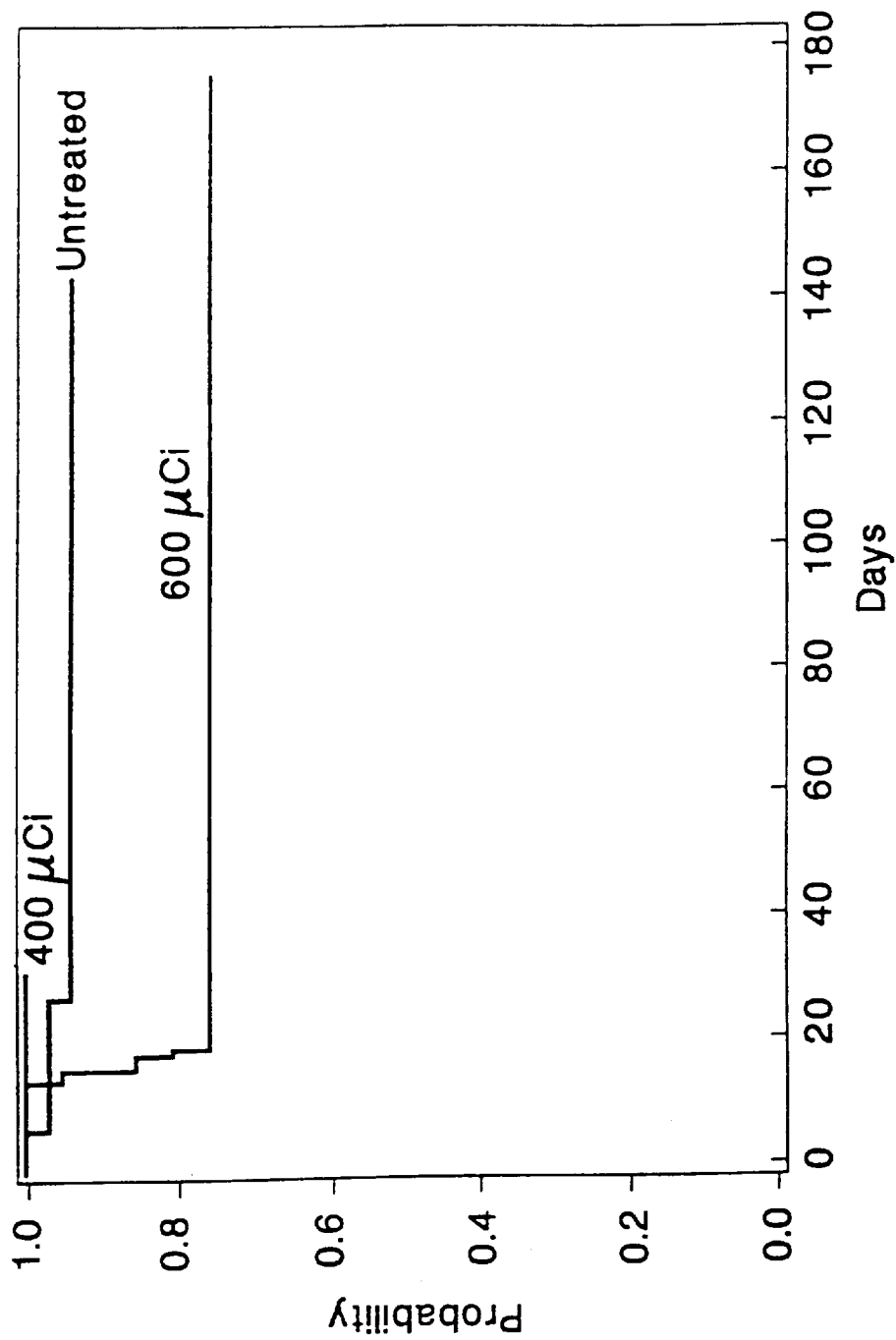
FIG. 14 shows the survival analysis of athymic nude mice bearing LS174T human colon carcinoma xenografts versus time after (A) a single $^{131}$I-labeled CC49 injection of 400 μCi, 600 μCi, or (B) multiple injections of 2×300 μCi $^{131}$I-labeled CC49 MoAb on days 0 and 3 or 0 and 7, or 3×300 μCi $^{131}$I-labeled CC49 on days 0, 3, and 7.
Figure 14B:
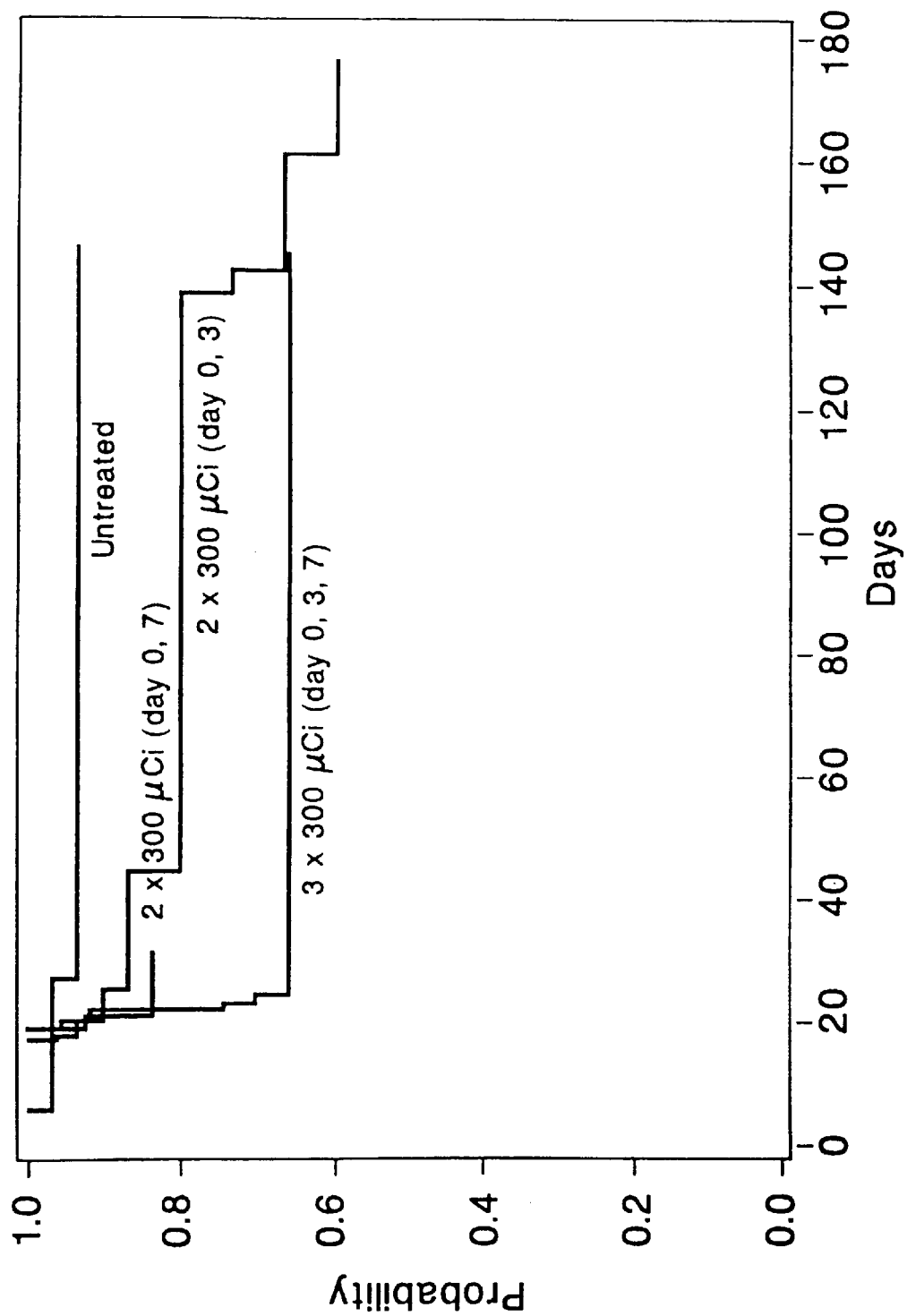

The use of multiple injections of $^{131}$I-labeled CC49 MoAb as a means to increase the therapeutic effect compared to a single administration (209) was examined. Athymic nude mice bearing established 7–9 day old LS174T s.c. tumor xenografts measuring 5–10 mm in diameter were injected intraperitoneally either singly with 400 or 600 µCi $^{131}$I-labeled CC49 (day 0) or multiply (days 0 and 3, 0 and 7, or days 0, 3, and 7) with 300 µCi $^{131}$I-labeled CC49 antibody. The animal lethality resulting from such treatment is shown in Table 5 and FIG. 14. Lethality usually occurred 2–4 weeks after radiolabeled antibody injection. The time to death from tumor or treatment, to tumor regression, and to tumor recurrence was recorded in days for each animal in every treatment group. A log rank test was performed to compare the difference in radiolabeled antibody treated animals with an untreated group of tumor-bearing animals (280). Animals with tumors equal to 10% of the animal's body weight or that ulcerated were euthanized, and were treated as censored data in the survival analysis. No lethality resulted after a single injection of 400 µCi $^{131}$I-labeled CC49. A single injection of 600 µCi $^{131}$I-labeled CC49 produced 24% (5/21) lethality which was not significantly different than untreated control animals (p=0.072). Two injections of 300 µCi $^{131}$I-labeled CC49 on days 0 and 3 produced 25% (8/32) lethality which did not differ significantly from untreated controls (p=0.083). There was 6% (2/35) lethality in untreated animals. When 300 µCi $^{131}$I-labeled CC49 antibody was injected on days 0 and 7, the lethality was 15% (2/13) which did not differ from untreated controls (p=0.303). When three injections of 300 µCi $^{131}$I-labeled CC49 were injected on days 0, 3, and 7, the lethality was 33% (8/24) which did differ significantly from untreated control animals (p=0.017).

TABLE 5

Animal lethality following treatment with $^{131}$I-labeled CC49[a]

| Group | No. Animals | Total Deaths[b] |
| --- | --- | --- |
| 400 µCi | 6 | 0 (0%) |
| 600 µCi | 21 | 5 (24%) |
| 2 × 300 µCi (Day 0, 3) | 32 | 8 (25%) |
| 2 × 300 µCi (Day 0, 7) | 13 | 2 (15%) |
| 3 × 300 µCi (Day 0, 3, 7) | 24 | 8 (33%) |
| Untreated | 35 | 2 (6%) |

[a]Groups of athymic nude mice bearing LS174T s.c. tumors were injected with $^{131}$I-labeled CC49 at the doses shown. Day 0 is the first day of antibody administration which was 9–11 days after tumor cell injection. The results of 1 to 3 studies were combined for each treatment group.
[b]Animals with tumors equal to 10% of the animal's body weight or that ulcerated were euthanized, and are omitted from this table.

Figure 1:
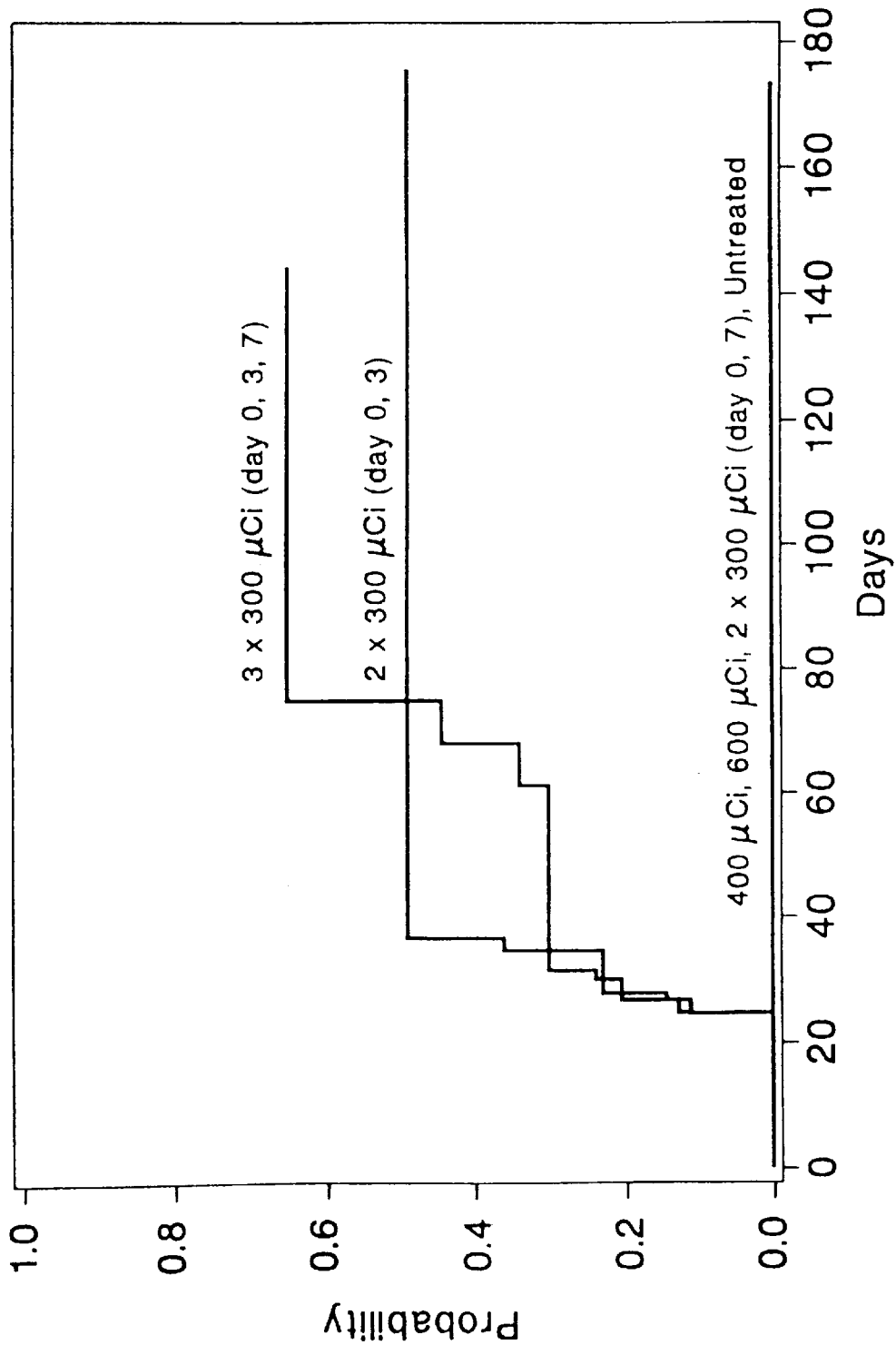
FIG. 1 shows the complete tumor regressions in athymic nude mice bearing established LS174T human colon carcinoma xenografts versus time after multiple injections of 300 μCi $^{131}$I-labeled CC49 on days 0 and 3 or 0, 3, and 7 as compared to a single injection of 400 or 600 μCi $^{131}$I-labeled CC49 or two injections of 300 μCi $^{131}$I-labeled CC49 on days 0 and 7. The number of animals/group is shown in Table I.

The LS174T tumor regression following $^{131}$I-labeled CC49 antibody treatment is shown in Table 1 and FIG. 1. No tumor regression was observed in animals treated with a single injection of 400 or 600 µCi $^{131}$I-labeled CC49 antibody. In animals injected with 300 µCi $^{131}$I-labeled CC49 on days 0 and 3, there was 31% (10/32) complete tumor regressions which was significantly different from untreated control animals (p=0.0001). By contrast, there were no tumor regressions when 300 µCi $^{131}$I-labeled CC49 was injected on days 0 and 7. No regressions occurred in untreated animals.

When 300 µCi $^{131}$I-labeled CC49 was injected on days 0, 3, and 7, complete tumor regression occurred in 42% (10/24) of animals which was significantly different than the untreated group (p=0.0001). Taking into account that 8/24 animals in this treatment group died by day 28 (Table 5), complete tumor regressions occurred in 63% (10/16) of the animals that survived the treatment.

TABLE 1

Tumor regression following treatment with $^{131}$I-labeled CC49[a]

| Group | No. Animals | Total Regressions |
|---|---|---|
| 400 µCi | 6 | 0 (0%) |
| 600 µCi | 21 | 0 (0%) |
| 2 × 300 µCi (Day 0, 3) | 32 | 10 (31%) |
| 2 × 300 µCi (Day 0, 7) | 13 | 0 (0%) |
| 3 × 300 µCi (Day 0, 3, 7) | 24 | 10 (42%) |
| Untreated | 35 | 0 (0%) |

[a]Groups of athymic nude mice bearing LS174T s.c. tumors were injected with $^{131}$I-labeled CC49 at the doses shown. Day 0 is the first day of antibody administration which was 9–11 days after tumor cell injection. The results of 1 to 3 studies were combined for each treatment group.

Figure 2:
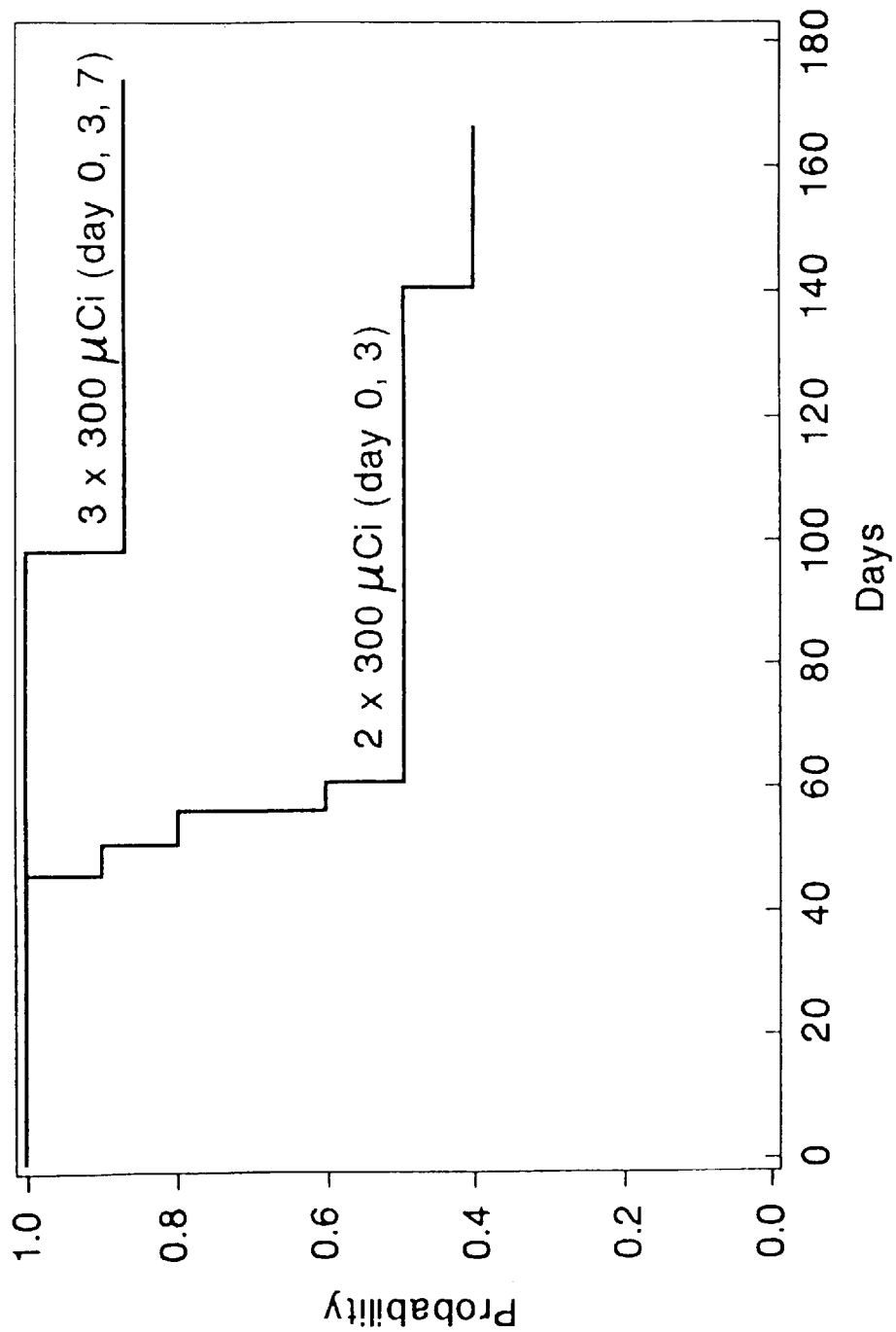
FIG. 2 shows the tumor recurrence free survival of animals treated with multiple injections of 300 μCi $^{131}$I-labeled CC49 on days 0 and 3 or 0, 3, and 7 versus time after treatment. The number of animals/group is shown in Table II.
Figure 3:
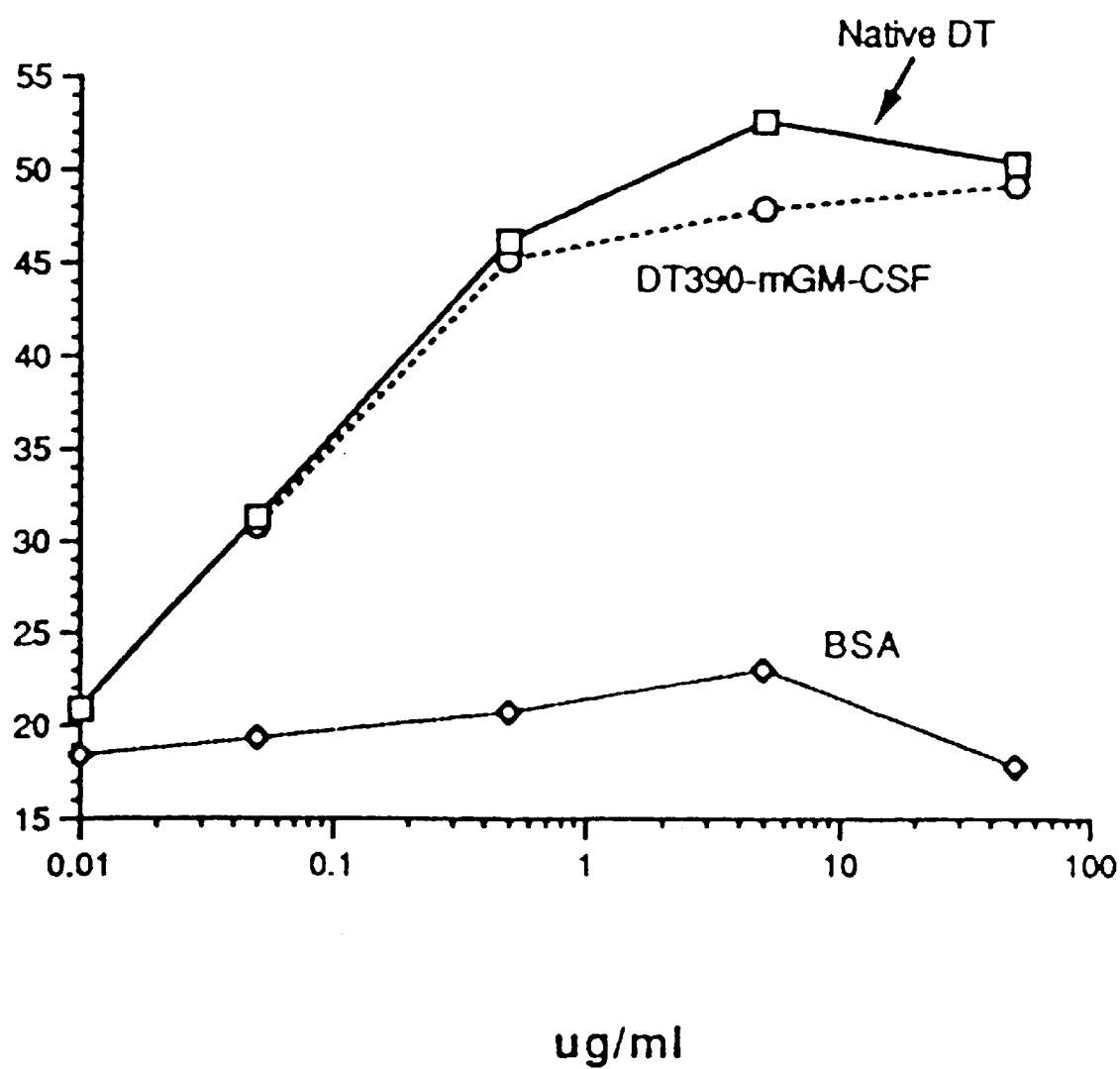
FIG. 3 shows the ADP ribosyl transferase activity of $DT_{390}$-mGM-CSF. Trypsin-nicked $DT_{390}$-mGM-CSF, trypsin nicked native diphtheria toxin, or bovine serum albumin was studied in a cell-free assay. Protein was added at various concentrations to the reaction system. The activity was measured as the cpm of bound $^{32}$P-AD-ribose to rabbit reticulocyte lysate (elongation factor 2).
Figure 4:
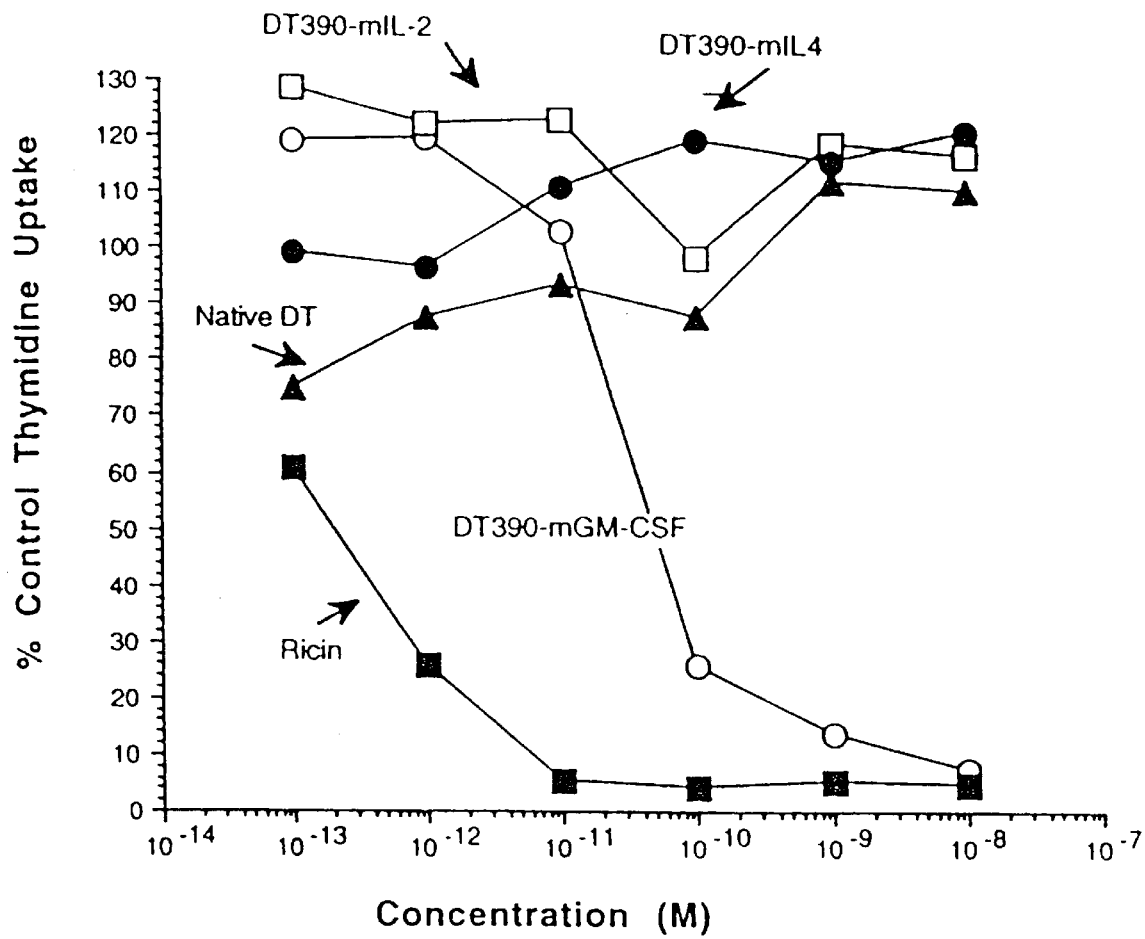
FIG. 4 shows protein synthesis inhibition activity of fusion toxins on FDCP2.1d cells. Fusion toxins were added at various concentrations to FDCP2.1d cells for 4 hours. After washing out toxin, the percent incorporation of [$^3$H] thymidine relative to untreated controls was determined.
Figure 5:
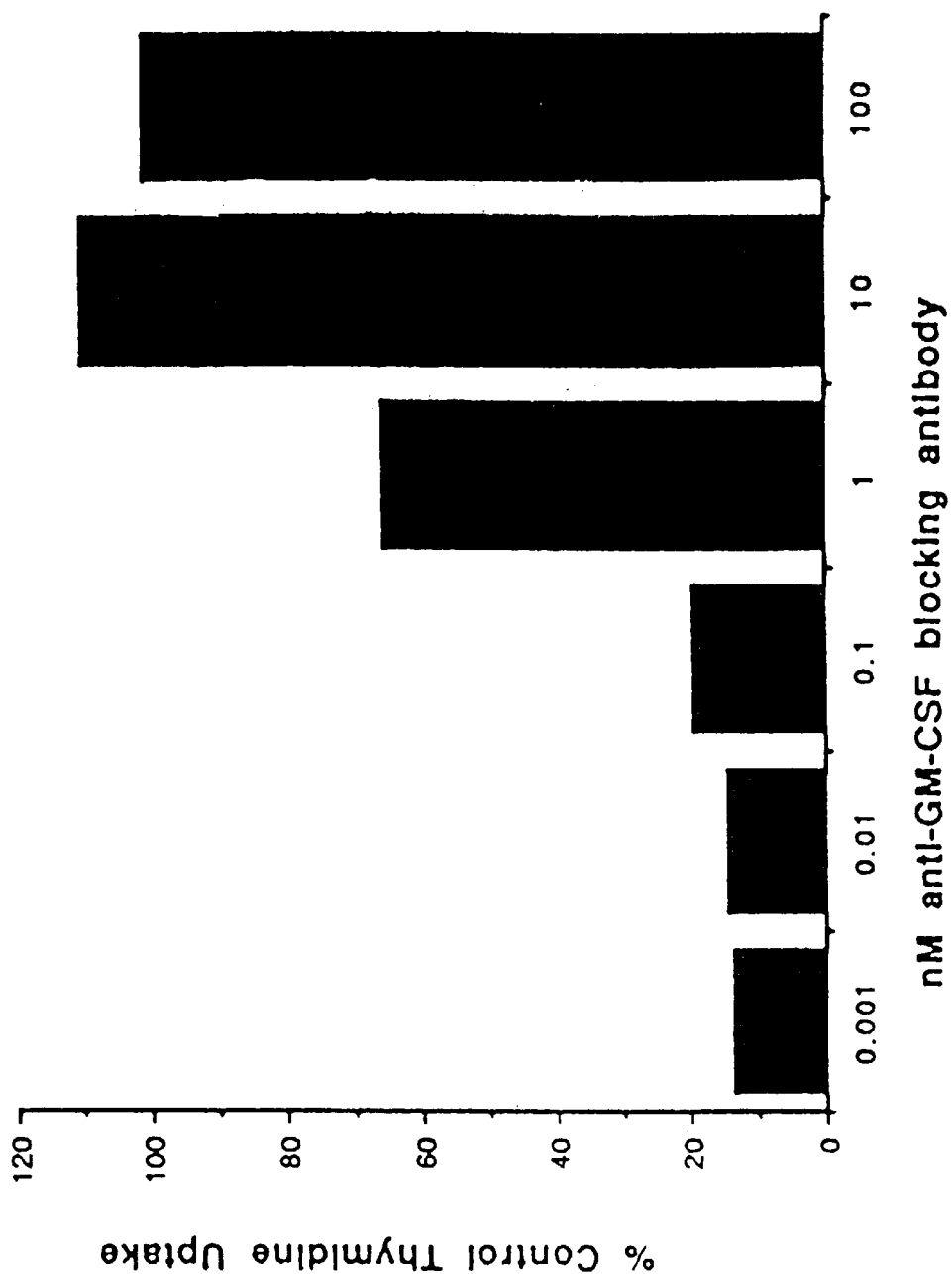
FIG. 5 shows the neutralization of $DT_{390}$-mG-CSF by anti-mGM-CSF antibody. $DT_{390}$-mGM-CSF ($10^{-9}$M) was incubated with various concentrations of anti-mGM-CSF antibody or with no antibody and added to FDCP2.1d cells. Results percent of thymidine uptake of untreated control cells.
Figure 6:
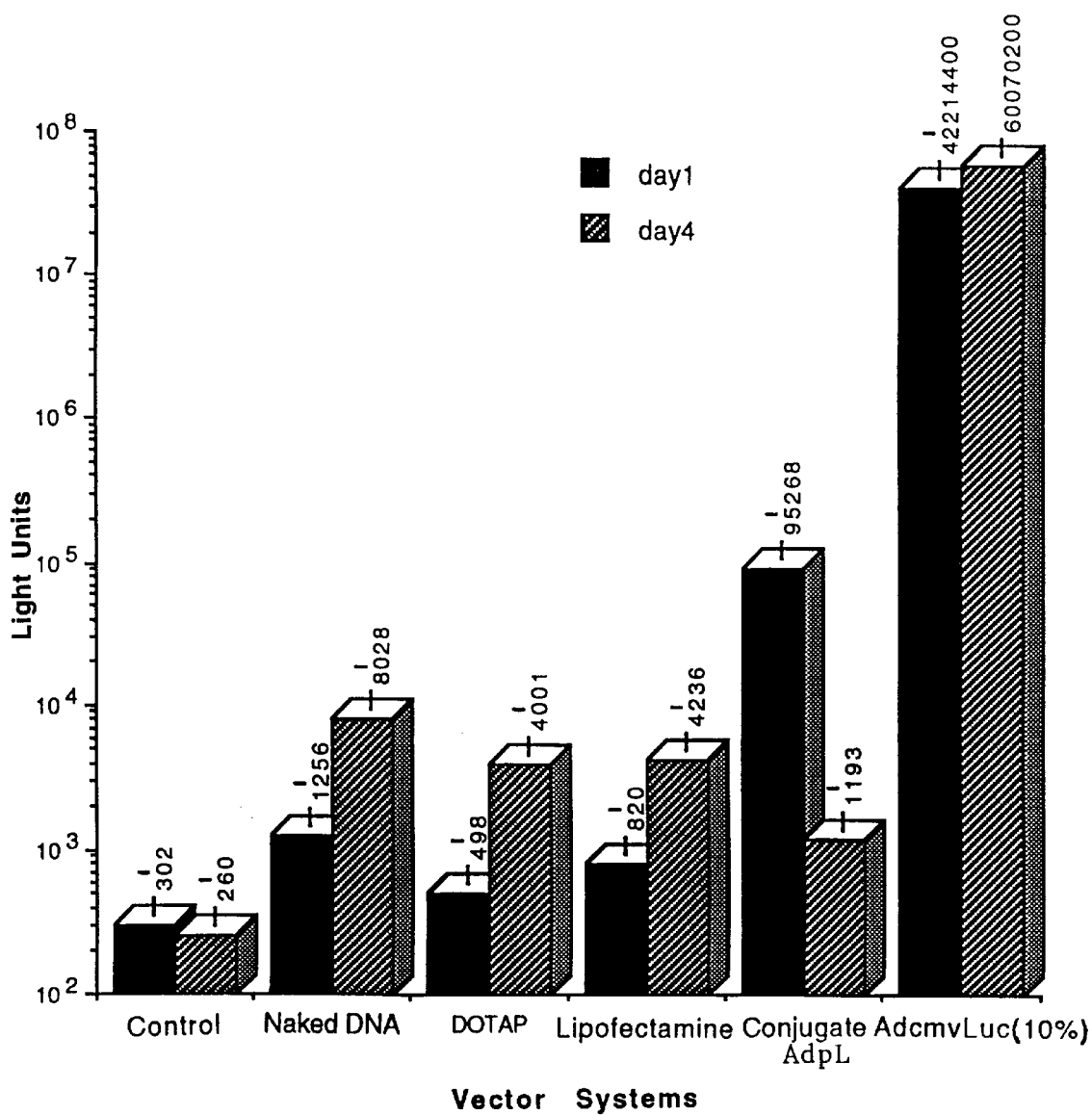
FIG. 6 shows the direct in vivo gene transfer to breast cancer tumor xenografts. Various vector systems were delivered to subcutaneous tumor xenografts of the human breast cancer cell line MDA-MB-435 in athymic nude mice by direct injection. The vectors employed delivered reporter gene firefly luciferase. At various intervals post-transduction tumor nodules were harvested and analyzed for activity of the encoded luciferase enzyme. Evaluated vectors included naked DNA, liposome-DNA complexes (DOTAP and Lipofectamine), adenovirus-polylysine-DNA complexes (conjugate), and recombinant adenoviruses (AdCMVLuc).
Figure 7:
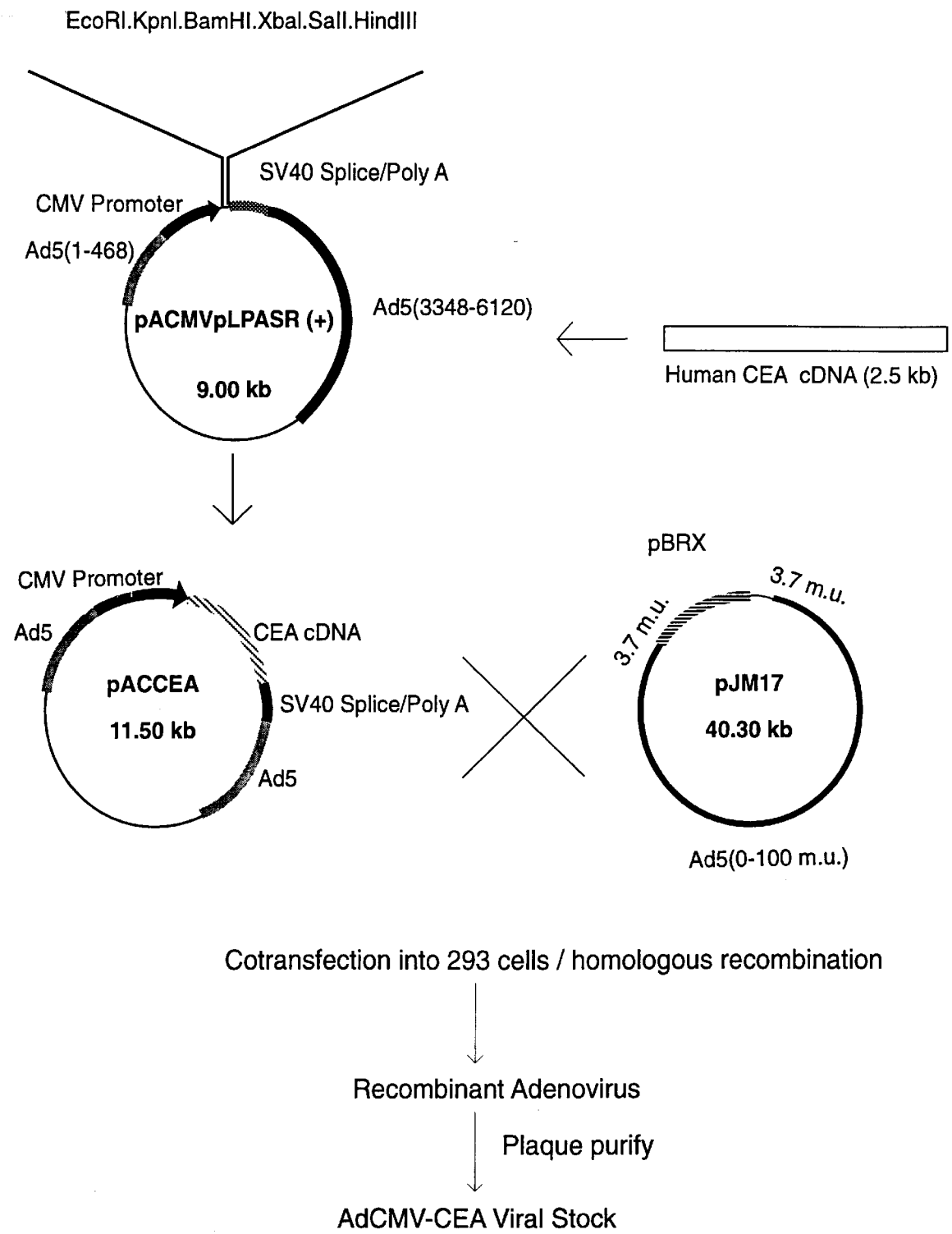
FIG. 7 shows the schema for deriving recombinant adenoviral vector encoding the human CEA gene. For the construction of recombinant adenoviral vectors, the plasmids shown were obtained from Dr. Frank Graham of the McMaster University, Hamilton, Ontario.
Figure 8:
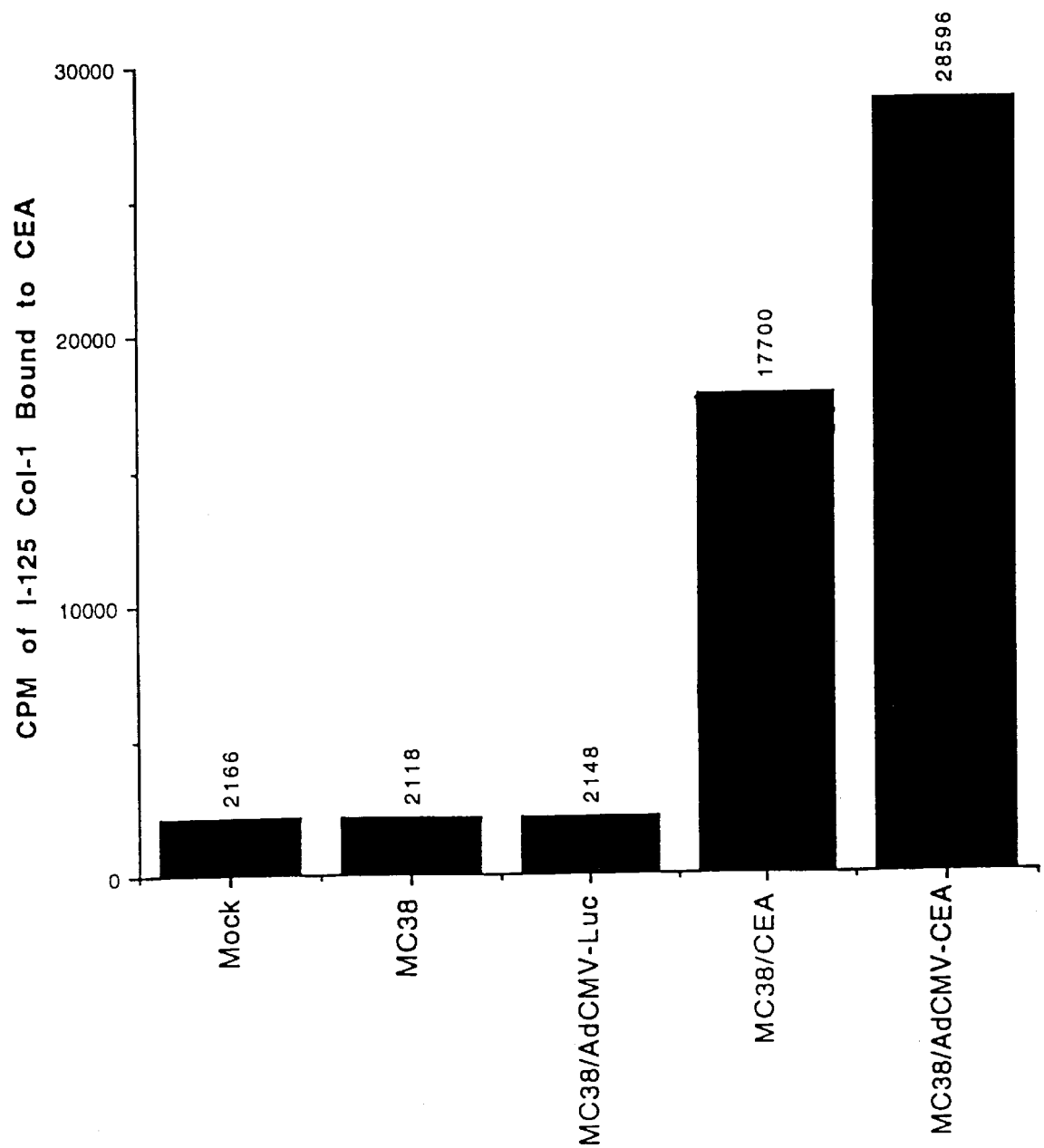
FIG. 8 shows the gene transfer of human CEA mediated by CEA-encoding recombinant adenovirus. Various target cells were evaluated for cell surface expression of human CEA employing binding of the anti-human CEA MoAb Col-1. Murine colonic carcinoma cell line MC-38, MC-38 transduced with a firefly luciferase encoding adenovirus (AdCMV-Luc), MC-38 stably transfected to constitutively express the human CEA cDNA (MC38/CEA), and MC-38 cells transduced with the human CEA-expressing recombinant adenovirus (MC38/Adcmv-CEA).

To analyze serial measurements of tumor size over time, mathematical models were fitted to data to estimate the slope of the growth curves. The goodness of fit of the models was examined through scatter graph and statistical analysis of residues (281). Tumor recurrence occurred in some of the animals treated with $^{131}$I-labeled CC49 antibody, as shown in Table 2 and FIG. 2. In animals injected with 300 µCi $^{131}$I-labeled CC49 on days 0 and 3, 60% (6/10) of previously regressed tumors recurred. Only 20% (2/10) of the tumors that regressed after receiving 300 µCi $^{131}$I-labeled CC49 on days 0, 3, and 7 recurred by day 150. The difference in recurrence between this group and the other one was close to significant (p=0.056).

TABLE 2

Tumor recurrence in animals treated with $^{131}$I-labeled CC49 that showed complete tumor regression[a]

| Group | No. Animals | Total Recurrences |
|---|---|---|
| 2 × 300 µCi (Day 0, 3) | 10 | 6 (60%) |
| 3 × 300 µCi (Day 0, 3, 7) | 10 | 2 (20%) |

[a]Groups of athymic nude mice bearing LS174T s.c. tumors were injected with $^{131}$I-labeled CC49 at the doses shown. Day 0 is the first day of antibody administration which was 9–11 days after tumor cell injection.

Figure 15:
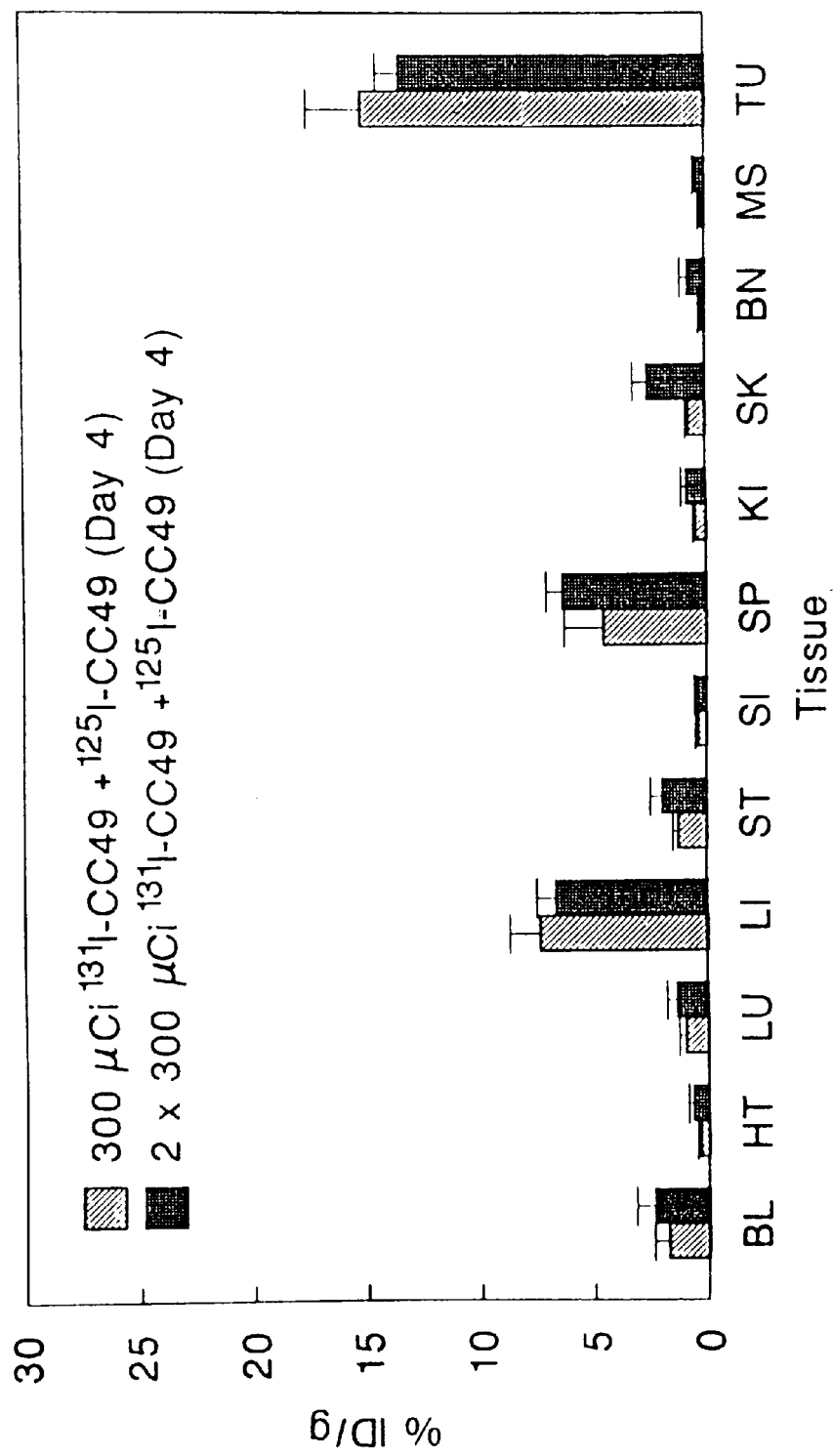
FIG. 15 shows the biodistribution of 1 μCi (0.1 μg) 125I-labeled CC49 injected i.p. in groups in 8 or 7 athymic nude mice bearing approximately 1 g s.c. LS174T human colon carcinoma xenografts and receiving respectively (□) 300 RCi $^{131}$I-labeled CC49 or (■) 2×300 μCi $^{131}$I-labeled CC49 MoAb with a 3-day interval between injections. $^{125}$I-labeled CC49 was administered i.p. 24 hours after the first or second $^{131}$I-labeled CC49 injection, and the biodistribution of $^{125}$I-labeled CC49 was determined 4 days later with the % ID/g in tissues calculated 3 months later to allow for $^{131}$I decay; bars, SEM. BL, Blood; HT, heart; LU, lung; LI, liver; ST, stomach; SI, small intestine; SP, spleen; KI, kidney; SK, skin; BN, bone; MS, muscle; TU, tumor.
Figure 16:
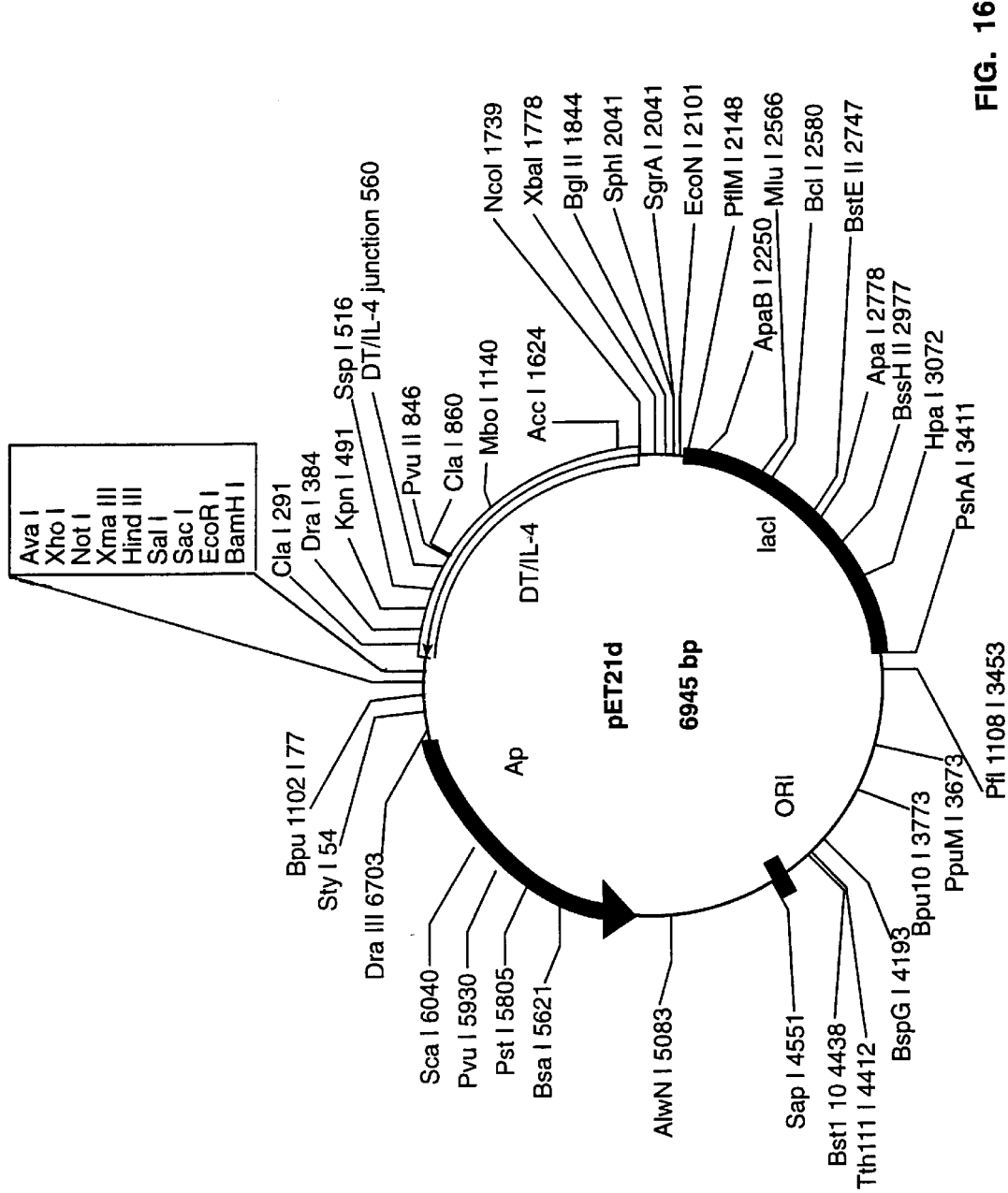
FIG. 16 shows the assembly of the DT$_{390}$-mIL-4 gene in the pET21d vector to form the plasmid pDTIL-4.
Figure 17:
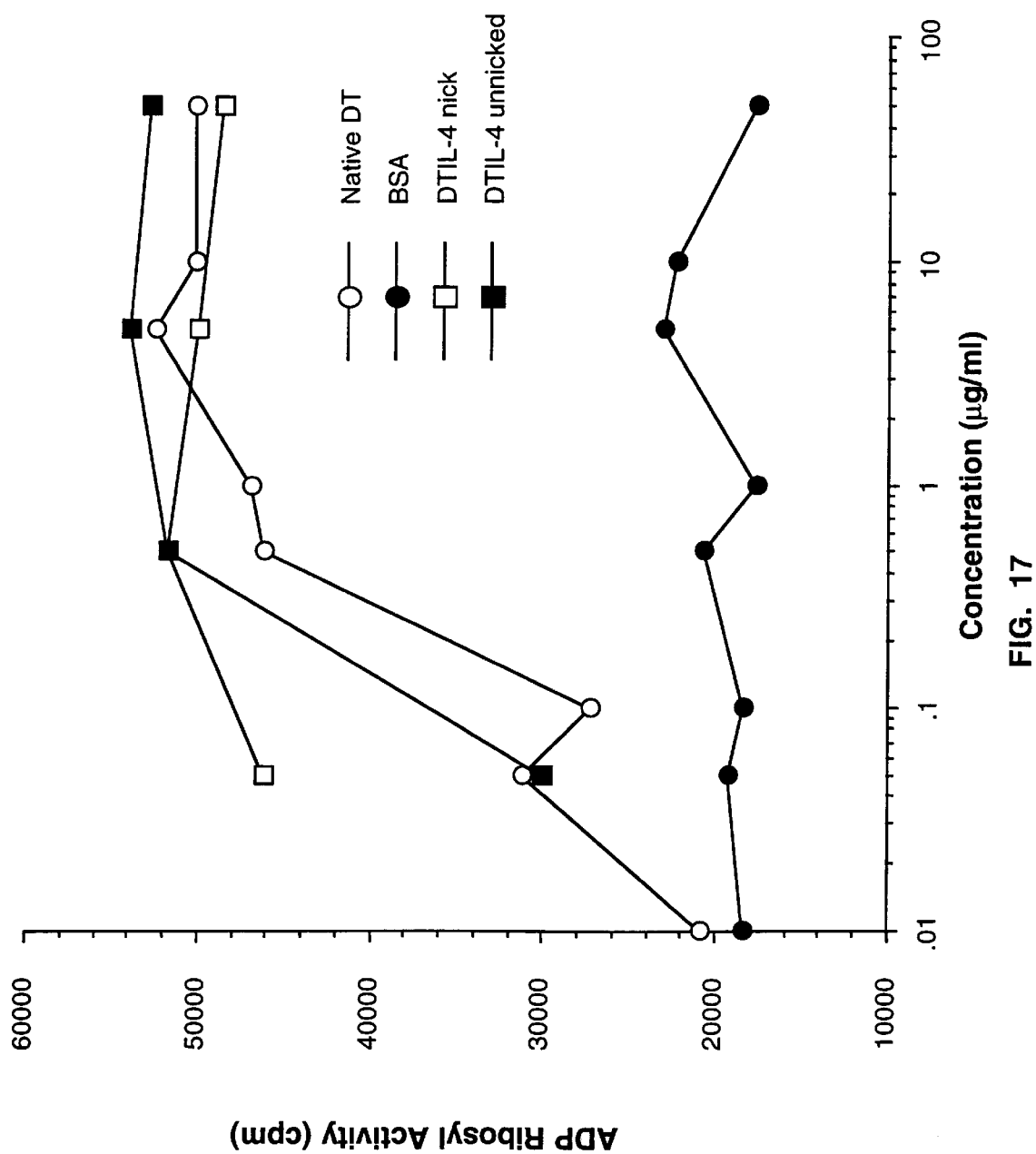
FIG. 17 shows the ADP ribosyl transferase activity of DT$_{390}$-mIL-4. Trypsin-nicked DT$_{390}$-mIL-4, unnicked DT$_{390}$-mIL-4, trypsin nicked native diphtheria toxin, or bovine serum albumin was studied in a cell-free assay. Protein was added at various concentrations to the reaction system. The activity was measured as the cpm of bound $^{32}$p AD-ribose to rabbit reticulocyte lysate (elongation factor 2).
Figure 18:
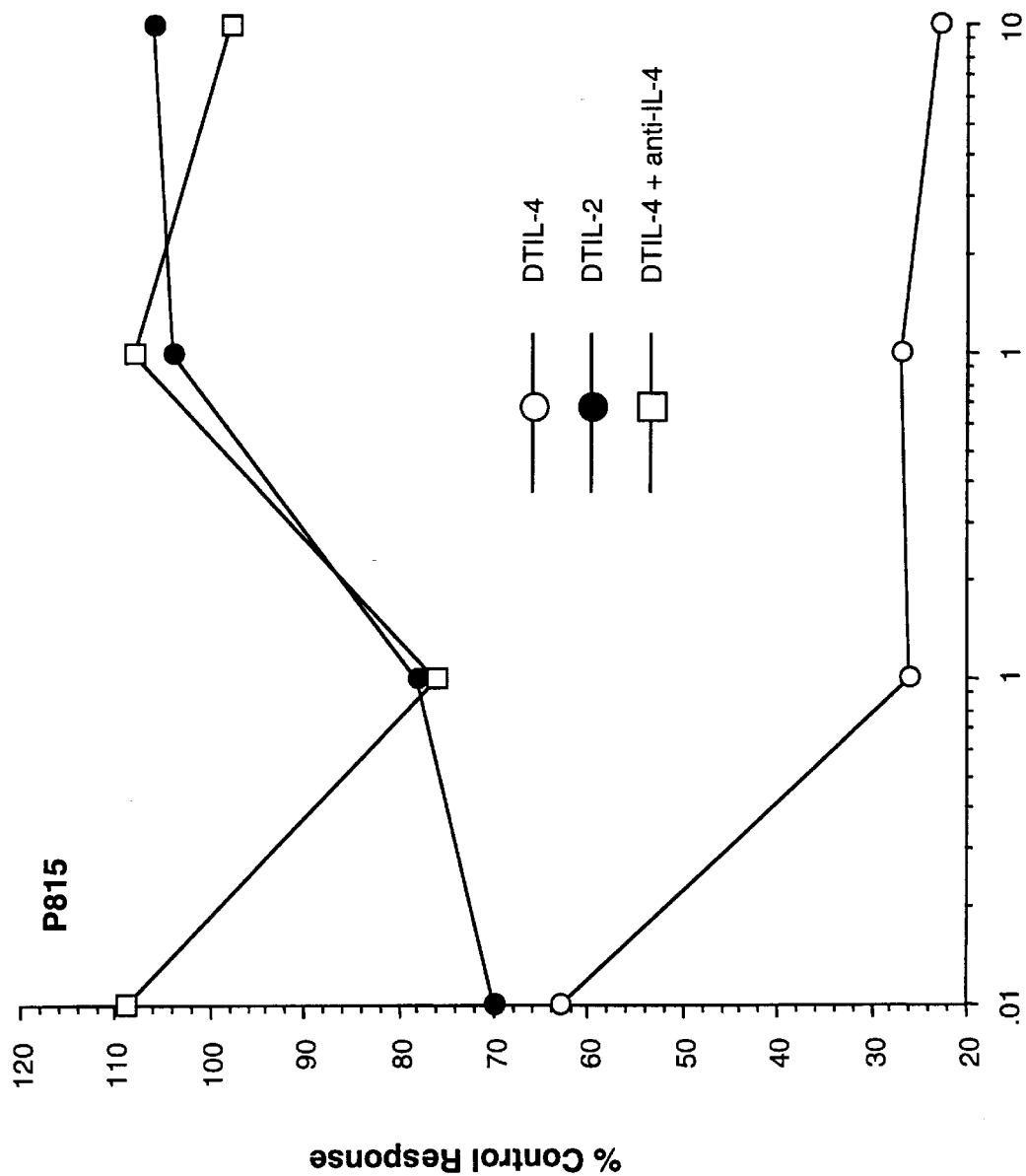
FIG. 18 shows cell proliferation inhibition activity of fusion toxins on P815 cells. Fusion toxins DT$_{390}$-mIL-4 and DT$_{390}$-hIL-2 were added at various concentrations to P815 cells for 24 hours. The percent reduction in cell number relative to controls treated with 0.01 nM fusion toxin was determined. Cytotoxic activity of DT$_{390}$-mIL-4 was inhibited by the addition of excess 11B11 rat anti-mouse IL-4 antibody for 15 min before addition to cells.
Figure 19:
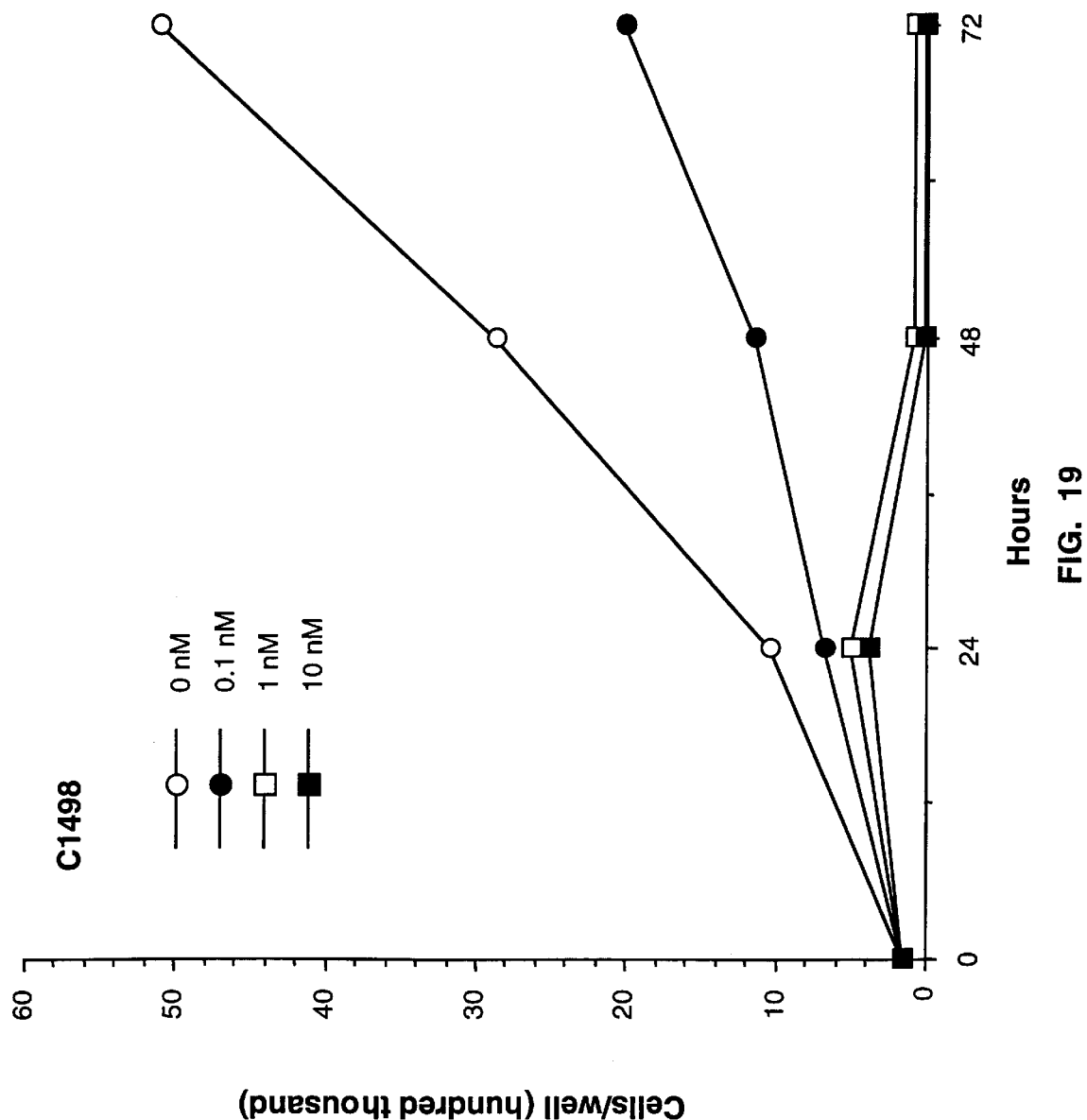
FIG. 19 shows cell proliferation inhibition activity of DT$_{390}$-mIL-4 fusion toxin on C1498 cells. DT$_{390}$-mIL-4 fusion toxin was added al various concentrations to C1498 cells for 24, 48, or 72 hours. Control untreated cells were cultured also. The number of cells/well was determined.

The results of treatment with one or two injections of 300 µCi $^{131}$I-labeled CC49 on the biodistribution of 1 µCi $^{125}$I-labeled CC49 in athymic nude mice bearing LS174T tumor xenografts are shown in FIG. 15. There was a similar tumor concentration of $^{125}$I-labeled CC49 four days after one (15.2±2.4% ID/g) or two (13.5±1.0% ID/g) treatments with $^{131}$I-labeled CC49. A t-test was used to analyze differences in the biodistribution of $^{125}$I-labeled CC49 following one or two injections of 300 µCi $^{131}$I-labeled CC49. These values were not significantly different (t-test, p>0.05). The concentrations of $^{125}$I-labeled CC49 in normal tissues were not significantly different (except skin, p=0.03) following exposure to one or two injections of 300 µCi $^{131}$I-labeled CC49.

Why two administrations of 300 µCi $^{131}$I-labeled CC49 would be more effective than a single administration of 600 µCi $^{131}$I-labeled CC49 is that the second administration of radiolabeled antibody is deposited initially at the periphery of the tumor where cells that survive the first dose are proliferating, whereas following a single administration the activity at the periphery decreases with time due to diffusion into the central region of the tumor resulting in a lower radiation absorbed dose at the periphery (226).

Estimation of radiation absorbed dose in tumor

Three-dimensional reconstructions of activity density distributions were developed for LS174T human colon cancer xenografts at 1, 3, 4, 7, and 10 days postinjection of 300 µCi $^{131}$I-labeled 17-1A MoAb. The reconstructions were based on autoradiographs of 32-µm sections taken at 200–400 µm section intervals. Dose-rate calculations were performed using a dose point kernel for $^{131}$I and the activity density distributions using the fast Fourier technique.

Dose calculations for the case of a 1 cm diameter LS174T human colon tumor xenografts in athymic nude mice using biodistribution data and 3-D dose-rate distributions indicated a greater dose deposition for 131-relative to $^{90}$Y-labeled 17-1A MoAb for equal injected activities (81). The shorter half-life of $^{90}$Y combined with the 3 to 4 day lag between injection and penetration into the tumor interior reduced both the total dose and dose nonuniformity. A greater proportion of dose escaped from the tumor with $^{90}$Y while the greatest $^{90}$Y activity concentration was at the tumor surface. The diffusion of the labeled antibody into the tumor interior had a dominant effect on the cumulative dose distribution.

Calculations were performed to help predict relative therapeutic outcome for $^{131}$I, $^{186}$Re, and $^{90}$Y. The data for the time-dependent uptake and 3-D activity density reconstructions for tumor collected for $^{131}$I were used. The activity densities for the other isotopes were calculated by accounting for the different radioactive decay properties and normalizing to total dose to bone marrow. For 1-cm diameter tumors, the dominant effect was the beta particle depth penetration. The $^{186}$Re and $^{90}$Y total dose distributions were successively more uniform, the total doses were also successively smaller (208). More energy escaped the tumor for the more penetrating beta particles. The differences in the isotope half-lives contributed to an observable, but lesser extent. Of importance is the approximately four day delay to achieve maximum uptake in tumor and the 7 to 10 day time lag to achieve optimum uniformity of uptake, favoring the longer half-life isotopes. At early times, the higher activity densities present at the tumor surface for $^{90}$Y was not an advantage because of the proportionately larger amount of energy leaving the tumor. The conclusion was that $^{131}$I, with the lowest beta energies and longest half-life performed best. However, when the additional dose to bone marrow in humans for the gamma contributions was included, both 131I and $^{186}$Re were comparably effective. The inclusion of the time-dependent 3-D activity reconstruction data provided a more realistic basis for the isotope comparison than previous studies (282). These calculations also agreed with the direct comparison of 131I and $^{90}$Y discussed above (81).

Derivations of stable transfected colon cancer cell lines

Stable transfectants of the CT-26 mouse colon cancer cell line are produced using standard cationic liposome techniques and the plasmid vectors. Transfected cell lines are maintained with G418 selection media and non-transfected control cells in standard media. Novel reagents such as AdpL to make vectors for the production of stably transfected cell lines (309) are used. Another option is the use of CELO virus (350).

Design and production of radioactive fusion toxins.

To utilize radioactive metals, it is necessary to efficiently and stably attach them to the fusion toxins. For the proposed radiometals (i.e., $^{90}$Y, $^{188}$Re and $^{186}$Re) two different types of bifunctional chelating agents (BCAs) are used. Yttrium is chelated with 1, 4, 7, 10-tetraazacyclododecane N, N', N", N'''-tetraacetic acid (DOTA) while rhenium is chelated with N-[tris[2-[[N-(benzyloxy)amino]carbonyl]ethyl] methyl] succinamic acid (trisuccin).

The process of radiolabeling with $^{90}Y$ is accomplished through standard procedures with commercially supplied yttrium [$^{90}Y$]-chloride. This involves buffering the hydrochloride solution of the radiometal to an appropriate pH and incubating the resulting preparation with the fusion toxin carrying DOTA. For $^{186}Re$ and $^{188}Re$, the perrhenate form of the metal is reduced to the lower oxidation forms and chelated to the trisuccin-conjugated fusion toxin. The mGM-CSF-DT or mIL-4-DT fusion toxin is radiolabeled with $^{125}I$ or $^{131}I$ by the standard Iodogen method (157). Gansow and co-workers have experimented extensively with chelate systems that could be used to radiolabel antibodies with $^{212}Bi$ and its parent, $^{212}Pb$ (106–109). A derivative of DTPA can bind $^{212}Bi$ effectively. This chelate does not bind $^{212}Pb$. DOTA, a macrocycle that contains carboxylate groups, can be used to bind the $^{212}Pb$. Solutions of 1 mM $HNO_3$ can be combined with the DOTA chelate and brought to pH 9 by NaOH. The mixture is heated to 50%C for 5 minutes and pH adjusted to 6 with $HNO_3$. Free metal or hydroxides are removed from the solution by passing the solution through a Chelex-100 column (BioRad). After determining satisfactory conditions for chelation, one examines the DOTA-fusion toxin complexes for stability and retention of cell binding properties after exposure to these conditions. Both $^{203}Pb$ and $^{206}Bi$ as radionuclide standards are available and can be quantitated by measurement of intensity of gamma ray emissions at 279 (80%) and 803 (99%) keV respectively. The $^{212}Pb$ radioactivity can be determined by measurement of its 239 keV (44%) gamma radiation. The determination of $^{212}Bi$ is done by counting the 583 keV (32%) gamma radiation at its $^{208}Ti$ daughter (t½=3.07 minutes) at transient equilibrium with the parent.

To screen and characterize RFT, certain animals receive the control tumor cell line in the peritoneum and the matched stable gene expressing cell line in the peritoneum of other mice, e.g. CT-26 in one group and CT-26-mGM-CSF receptor in the other group. Animals are sacrificed at multiple early time points (30 minutes, 2, 4, 6, 12, 24, 36 and 48 hours) following intraperitoneal injection for quantification of tumor, blood and normal organ radioactivity by standard techniques (81, 195). Initial screening is done with $^{125}I$-labeled ligands but all preparations which have tumor localizing ability have comparative studies done with $^{125}I$ versus $^{186}Re$, $^{188}Re$, $^{64}Cu$, $^{67}Cu$, $^{212}Pb$, $^{212}Bi$ to establish whether dehalogenation is causing an underestimate of the degree of localization and to analyze whether metal chelates are superior to iodinated ligands. For imaging studies, $^{131}I$-,$^{188}Re$-, $^{64}Cu$- and $^{186}Re$-labeled fusion toxins are used with 4, 12 and 24 hours imaging analysis.

Development of treatment strategies with radioactive fusion toxins

Once a prospective RFT has been characterized and found to have attractive tumor localization/biodistribution and dosimetry estimates, studies are carried out in a therapeutic mode to establish the (1) maximal tolerated dose using single and multiple dose regimens; (2) to analyze the effects of protein dose; and (3) to determine the antitumor:toxicity ratio of the therapeutic RFT formulations ($^{131}I$, $^{90}Y$, $^{186}Re$, $^{188}Re$, $^{64}Cu$, $^{68}CU$ $^{212}Pb$, and $^{212}Bi$). These studies use standard toxicity monitoring and animal survival parameters in mice carrying control versus tumors with stable expression of the mGM-CSF or mIL-4 receptor.

Methods to genetically induce tumor cell membrane expression of mGM-CSF receptors (xenogeneic to human tumor cells).

Human tumor cells are transduced with xenogeneic cell surface receptors to allow selective binding of RFT. This involves the use of the murine receptors for GM-CSF or IL-4 in conjunction with the corresponding radiolabeled fusion toxin. The expression pattern of the xenogeneic receptor in human tumor target cells is analyzed. The induced binding specificities of human tumor target cells transduced with the murine receptor cDNAs is analyzed.

Expression pattern of the xenogeneic receptors in human tumor targets

For these studies, the human tumor lines are transduced with the murine GM-CSF or IL-4 cDNAs employing the high efficiency adenoviral vector method as before. Cells are analyzed for the expression of the corresponding xenogeneic murine receptor employing immunohistochemistry and FACS. Rat monoclonal antibodies specific for mouse GM-CSF or IL-4 receptor are used along with peroxidase or fluorescein labeled rabbit anti-rat immunoglobulin reagents. These studies determine the level of cell surface expression of these heterologous receptors. In addition, the temporal pattern of receptor expression after transient transfection is determined.

Analysis of the induced binding specificities of human tumor target cells transduced with the murine receptor cDNA For these studies, the human tumor cell lines are transduced with the murine GM-CSF or IL-4 receptor cDNA employing the adenoviral vector methodology as before. Cells are analyzed for binding of the corresponding mGM-CSF or recombinant mGM-CSF-DT fusion toxin. This is accomplished employing $^{125}I$-labeled recombinant murine GM-CSF or IL-4 (Immunex) or $DT_{390}$-mGM-CSF for cells expressing the murine GM-CSF or IL-4 cDNA. This allows quantitation of the number of receptors/cell and an estimate of the binding affinity.

Animal models to demonstrate the antitumor efficacy using intraperitoneal transduction and optimal radiolabeled fusion toxins The pattern of gene expression of the heterologous surface membrane receptor (murine GM-CSF or IL-4 receptor), the binding, biodistribution, kinetics and dosimetry estimates utilizing the optimized radiolabeled fusion toxins and the antitumor efficacy versus toxicity are analyzed. These studies provide information of the specific methods whereby genetic transduction may be combined with RFT binding to achieve in vivo tumor targeting and therapy.

Pattern of gene expression of the heterologous membrane receptors

To optimize any in vivo targeting protocol based upon genetic transduction with the RFT constructs, a prior determination must be made of heterologous gene expression at tumor sites post-transduction. For these studies, tumor xenografts are established intraperitoneally or subcutaneously in athymic nude mice employing the human tumor cell lines. Tumor samples are transduced in situ by intraperitoneal or intravenous injection. Recombinant adenoviral vectors are derived encoding the gene constructs for mGM-CSF or IL-4 receptor. These vectors are employed to deliver the corresponding gene constructs to the tumor cells. At various time points post-transduction, the tumor cells are harvested for analysis of the expression of the transferred gene. These studies of gene expression include: a) Northern blot analysis of the transcripts encoding the genes; b) immunohistochemistry and FACS analysis and c) radioligand binding for quantitating binding sites per cell.

Biodistribution, pharmacokinetics, and dosimetry estimates using the optimal radiolabeled fusion toxins These studies are directed to the expression of the mGM-CSF or IL-4 receptor binding constructs in vivo and their coupling to an enhanced in vivo RFT binding. Human tumor xenografts are established in athymic nude mice employing the human tumor cell lines. Experimental groups (N=6 animals) receive an intraperitoneal injection of the genetic construct for the high affinity mGM-CSF or IL-4 surface receptor while control groups (6 animals each) receive a non-specific genetic construct expressing lacZ. At the time of optimal gene expression, both groups receive intraperitoneal injection(s) of the appropriate RFT ($^{90}$Y, $^{186}$Re, $^{188}$Re, $^{64}$Re, $^{67}$Re, $^{212}$Pb, $^{212}$Bi or $^{131}$I-labeled) at the optimal dose, construct and schedule derived. Animals are sacrificed at appropriate intervals for quantitation of radioactivity in tumor, blood and normal tissues for biodistribution, pharmacokinetics, and dosimetry estimates. Tumor and normal tissues undergo radioautography to analyze distribution of radioactivity.

Efficacy of Genetic Radio-Isotope Targeting Strategies in vivo

Intraperitoneal or subcutaneous xenografts of human tumor cell lines are established and groups of 10 animals receive intraperitoneal or intratumoral injections of the genetic construct expressing the high affinity mGM-CSF or IL-4 membrane receptor (experimental) or lacZ (control), and subsequently both groups receive therapy with the radioligand carrying therapeutic doses of radioisotopes ($^{90}$Y, $^{131}$I, $^{186}$Re, $^{188}$Re, $^{64}$Re, $^{67}$Re, $^{212}$Pb and $^{212}$Bi) established to be optimal. Animal survival data of experimental and control groups of animals provide in vivo confirmation of the efficacy and toxicity.

Specific Methods

For the derivation of stably transfected colon cancer cell lines, stable cell lines are derived which constitutively express the GM-CSF receptor cDNA. To accomplish this, cells are transfected with cationic liposomes (Lipofectin, BRL) by standard methodologies. As the receptor cDNA construct possesses a neomycin selectable marker, G418 selection is used for selection of transfected clones. Briefly, approximately 1×10$^5$ cells of each cell type are seeded into 6 cm tissue culture dishes. Complexes are formed between Lipofectin (20.0 μg) and plasmid DNA (2.0 μg) and delivered to the cells in serum-free medium (Optimen, BRL). After six hours, the lipid DNA mixture are removed and replaced with complete tissue culture medium. After an additional 24 hour incubation, cells are split into appropriate medium supplemented with G418 (1 mg/ml) and propagation continued until colonies appear. These clones are isolated and expanded. The harvested stably modified clones are evaluated for the presence of the GM-CSF cell surface receptor.

Derivation of gene transfer vectors

Recombinant adenoviral vectors are derived encoding the GM-CSF, EGF or IL-4 receptor. The techniques employed for this construction are based upon the method of in vivo homologous recombination developed by Graham et al. (311). A DNA fragment encoding the gene is derived from parent plasmid by appropriate restriction endonuclease digestion followed by gel purification. This cDNA is cloned into the polylinker sites of the adenoviral shuttle vector pACMVPLPARS (+) provided by F. Graham. The recombinant shuttle vector containing the GM-CSF receptor gene in the appropriate orientation is then co-transfected with the adenoviral vector plasmid pJM17 into the EIA transcomplementing cell line 293 (transformed human embryonic kidney) employing lipofectin (BRL) using the manufacture's recommendations. The above strategy is designed to allow the derivation of replication-incompetent, recombinant adenoviral vectors deleted of the E1A region. Transfected cells are over-layered with soft-agar and plates monitored for formation of plaques. Isolated plaques are expanded, re-plaqued×3 and viruses purified for analysis. Confirmation of recombinant adenoviral identity will be by analysis with polymerase chain reaction employing primers specific for the GM-CSF or IL-4 receptor gene constructs, restriction analysis, and sequencing employing the di-deoxy chain termination method.

After incubation, cells are harvested for analysis of expression of the luciferase or lacZ reporter genes. For the detection of luciferase activity of in vitro transfected cells, cell lysates are harvested and luciferase assay carried out using the Promega luciferase kit employing conditions recommended by the manufacturer. Cell lysates normalized for total protein content (10 μg cytoplasmic protein) is analyzed for luciferase activity using a Lumat LB 950 (Berthold) and counted over a 10 second interval. For in vivo study of exogenous mRNA expression, tumor xenografts are removed 18 hours after intratumoral injection and immediately homogenized in lysis buffer. After removing cellular debris by centrifugation, 100 μg of cytoplasmic protein containing lysate are analyzed for luciferase activity as before.

For the detection of β-galactosidase expression, transfected cells are stained using two methods for lacZ activity: (1) X-gal chromogenic substrate, and (2) Fluorescein β1-(β-D-Galactopyranoside) (FDG) fluorogenic substrate. For the X-gal analysis, transfected cells are fixed for 10 minutes at room temperature with 0.5% glutaraldehyde in IX PBS, rinsed twice with PBS containing 1 mM MgCl$_2$ and stained for 4 hours at 37° C. in 1X PBS containing 1 mM X-gal (Sigma), 5 mM K$_3$Fe(CN)$_6$, 5 mM K$_4$Fe(CN)$_6$ and 1 mM MgCl$_2$. For the fluorescence-activated cell sorting (FACS) analysis, transfected cells are washed with 1X PBS supplemented with 4% FCS and 10 mM Hepes, then stained at 37%C with FDG (Sigma) for 2 minutes. Stained cells are harvested and fixed in 1% paraformaldehyde and 8.5% NaCl, pH7.4 prior to analysis in FACsort (Becton Dickinson).

Construction of hybrid gene and plasmid

Oligonucleotides are synthesized using cyanomethyl phosphoramidite chemistry on an Applied Biosystems model 380 A DNA synthesizer and purified by chromatography on Oligonucleotide Purification Cartridges (Applied Biosystems Inc., Foster City, Calif.) as recommended by the manufacturer. Purified oligonucleotides are resuspended in TE buffer (10 mM Tris base, 1 mM EDTA, pH 8.0). The hybrid gene encoding DT$_{390}$-mGM-CSF is constructed by the method of gene splicing by overlap extension (SOE) as described (312). Briefly, a DT gene fragment is generated in the first polymerase chain reaction (PCR) by using 5.5 ng plasmid containing the cDNA of DT mutant CRM107 as a template with primers 'a' and 'b' (Table 7). Primer 'a' creates an Nco I restriction site and an ATG initiation codon 5' to the DT coding sequence. Primer 'b' introduces a coding sequence for a linker [Ser(Gly)$_4$]$_4$ (SEQ ID NO: 6) directly after amino acid 389 of the mature DT molecule. A murine GM-CSF gene fragment is generated in the second PCR by using 1.8 ng plasmid containing the cDNA of murine GM-CSF as a template with primers 'c' and 'd'. Primer 'c' creates sequence homology with the linker at the 3' end of the DT fragment generated in the first PCR. This region of homology is placed 5' to the sequence encoding amino acid 26 of the GM-CSF molecule. Primer 'd' introduces a Xho I restriction site at the end of the GM-CSF molecule. The two fragments generated in the PCRs described above are purified and used as templates in a SOE reaction using primers 'a' and 'd'. This SOE forms the full-length

TABLE 7

| Sequence of oligonucleotides used herein | | |
|---|---|---|
| (a) The sense primer introduced an Nco I site with an initiation codon ATG and the initial 5 condons of DT. | 5'AGATATACCATGGGCGCTGATGTTGTTGAT3' | (SEQ ID NO:7) |
| (b) The antisense primer introduced the codons 386 to 389 of DT and codons of a linker [(Gly)4Ser]$^4$. | 5'CGACCCACCACCGCCCGAGCCACCGCCAC CGCTTCCACCGCCTCCAGATCCGCCGCCACC AAATGGTTGCGTTTTATG3' | (SEQ ID NO:8) |
| (c) The sense primer introduced the codons 26 to 31 of GM-CSF and codons of part of the linker. | 5TCGGGCGGTGGTGGGTCG GTCACCCGGCCTTGGAAG3' | |
| (d) The antisense primer introduced an Xho I site and the last 7 codons of GM-CSF. | 5'CGTGCGCTCGAG TTTTTGGCTTGGTTTTTTGCA3' | |

The sequence of the restriction site is in bold text.

$DT_{390}$-mGM-CSF hybrid gene. The $DT_{390}$-mGM-CSF hybrid gene is digested with restriction enzymes Nco I and Xho I (Gibco BRL, Gaithersburg, Md.) and ligated into the Nco I and Xho I cloning sites in the pET21d plasmid (Novagen, Madison, Wis.).

Expression and localization of fusion proteins

Plasmid, pDTGM-CSF, is transformed into the *E. coli* strain BL21 (DE3) (Novagen, Madison, Wis.) and protein expression is evaluated. Briefly, recombinant bacteria is grown in 500 ml Luria broth, supplemented with 100 $\mu$g/ml carbenicillin (Sigma, St. Louis, Mo.), in a 2 L flask at 37° C. When the absorbance ($A_{600}$) of the culture reaches 0.6, expression of the hybrid gene are induced by the addition of isopropyl-β-D-thiogalactopyranoside (IPTG) (Gibco BRL, Gaithersburg, Md.). Three hours after induction, the bacteria are harvested by centrifugation at 5000 g for 10 minutes. To determine the localization of expressed protein, an aliquot of bacterial pellet is resuspended in 30 mM Tris, pH7.5, 20% sucrose, 1 mM EDTA and osmotically shocked by placing in ice cold 5 mM $MgSO_4$. The periplasmic fraction (supernatant) is obtained by centrifugation at 8000 g for 10 minutes. Another aliquot of bacterial pellet is resuspended in sonication buffer (50 mM Sodium Phosphate, pH 7.8, 300 mM NaCl). After incubation sat −20° C. for 16 hours, the resuspended sample is sonicated for 5 minutes. The spheroplast fraction (pellet) and cytosolic fraction (supernatant) is collected separately by centrifugation at 10,OOOg for 20 minutes.

SDS-PAGE and Immunoblotting

Crude and purified fusion proteins are analyzed on sodium dodecyl sulfate polyacrylamide gel electrophoresis (SDS-PAGE). SDS-PAGE is performed using 4–20% gradient gels (Bio-Rad, Richmond, Calif.) and a Mini-Protein II gel apparatus (Bio-Rad, Richmond, Calif.). Proteins are stained with Coomassie brilliant blue. For immunoblotting, electrophoresed proteins are transferred to nitrocellulose membranes. Membranes are blocked with 3% gelatin containing TBS (20 mM Tris, 500 mM NaCl, pH 7.5) and washed with TTBS (TBS, 0.05% Tween-20, pH 7.5). Horse anti-DT antisera (Connaught Lab, Switwater, Pa.) and anti-GM-CSF (a rat IgG monoclonal antibody from clone 22E9.11 supplied by Dr. John Abrams (DNAX, Palo Alto, Calif.) are used as a source of primary antibodies. The blots are processed using horseradish peroxidase conjugated protein-G (Protein G-HRP) and developed using HRP color reagents (Bio-Rad, Richmond, Cailf.).

Isolation of inclusion bodies and purification of the fusion proteins

To isolate expressed protein from inclusion bodies, a bacterial pellet is resuspended in TE buffer (50 mM Tris, pH 8.0, 20 mM EDTA, 100 mM NACl) and treated with 5 mg/ml lysozyme for 30 minutes. The pellet is then incubated in Triton X-100 buffer (11% v/v Triton X- 100, 89% v/v TE) for 30 minutes at room temperature after briefly homogenizing with a tissuemizer (Thomas Scientifics, Germany). Inclusion bodies are collected by centrifugation at 24,000 g for 50 minutes. Solubilization of the inclusion body pellet are achieved in the presence of strong denaturants and reducing agents in a buffer consisting of 7 M guanidine, 0.1 M Tris, pH 8.0, 2 mM EDTA, and 65 mM dithioerythritol (DTE). The solution is incubated at room temperature for 16 hours. To remove insoluble material, the solution is centrifuged at 40,000 g for 10 minutes. Protein concentrations are determined according to Bradford method (35). Renaturation is initiated by a rapid 100-fold dilution of the denatured and reduced protein into refolding buffer consisting of 0.1 M Tris, pH 8.0, 0.5 M L-arginine, 0.9 mM oxidized glutathione (GSSG), and 2 mM EDTA. The samples are incubated at 10° C. for 48 hours. The refolded protein is diafiltrated and ultrafiltrated against 20 mM Tris, pH 7.8 using a spiral membrane ultrafiltration cartridge on Amicon's CH2 system (Amicon, Beverly, Mass.). Samples are loaded on a Q-Sepharose (Sigma, St. Louis, Mo.) column and eluted with 0.3 M NaCl in 20 mM Tris, pH 7.8. The protein is diluted fivefold and subsequently applied to another Q- Sepharose column and eluted with a linear salt gradient form 0 to 0.4 M NaCl in 20 mM Tris, pH 7.8. The main peak from the second Q-Sepharose column is purified by size-exclusion chromatography on a TSK 250 column (TosoHass, Philadelphia, Pa.).

ADP ribosylation assay

The toxin is nicked by treating 15 $\mu$g of $DT_{390}$-mGM-CSF with 0.04 $\mu$g of trypsin for 15 minutes at 37° C. The reaction is stopped with soybean inhibitor. Duplicate samples of nicked DT and $DT_{390}$-GM-CSF is examined for their ADP ribosyl transferase activity (313). Briefly, ADP-ribosylation is carried out in 80 $\mu$l reaction mixtures containing 40 $\mu$l of 0.01 M Tris -HCl buffer with 1.0 mM dithiothreitol, pH 8.0, 10 P1 of rabbit reticulocyte lysate (containing the elongation factor-2, (EF-2), and 10 $\mu$l of toxin sample. The reaction is initiated by the addition of 10 $\mu$l of 0.57 mM [$^{32}$p] nicotinamide adenine dinucleotide (ICN Biomedicals, Irvine, Cailf.). Reaction mixtures are incubated at room temperature for 1 hour and the reaction is stopped by the addition of 1 ml 10% trichloroacetic acid (TCA). The precipitate is collected by centrifugation and washed with 1 ml 10% TCA. The radioactivity will be counted by standard scintillation techniques.

Cytotoxicity assay

To characterize the cytotoxic activity of $DT_{390}$-mGM-CSF, one can use the murine myelomonocytic cell line FDCP2.1d (Immunex, Inc., Seattle, Wash.) which is dependent on mGM-CSF for proliferation. Cultured FDCP2.1 d cells are maintained in complete culture media consisting of DMEM supplemented with 10% fetal bovine serum, 1% Sodium Pyruvate, 1.5% L-Glutamine, 2% Penicillin/Streptomycin, 2% HEPES, 0.8% L-Arginine, 2% Folic Acid and L-Asparigine, and exogenous mGM-CSF at a final concentration of 1 ng/ml. The cytotoxic activity is assayed by measuring the ability of $DT_{390}$-mGM-CSF to inhibit the proliferation of FDCP2.1d cells. Cells initially are washed twice with plain DMEM to remove the exogenous cytokine followed by a 1 hour incubation at 37° C. A third wash is performed and the cells are resuspended. Cells are seeded at a concentration of $9\times10^4$ cells per tube in complete culture media and treated with the following toxins, $DT_{390}$-mGM-CSF, $DT_{390}$-hIL-2, $DT_{390}$-mIL-4, native DT and ricin at concentrations ranging from $1\times10^{-13}$ M to $1\times10^{-8}$ M. The cells are treated for 4 hours at 37° C. in a 5% $CO_2$ atmosphere. Following incubation, the tubes are centrifuged for 10 minutes at 300 g and the supernant decanted. The cells are washed with complete media three times and resuspended with 600 µl media after the third wash. Cells are seeded at $3\times10^4$ cells/well in 96-well flat-bottomed plates in a volume of 200 µl. One µCi [$H^3$]Thymidine and exogenous mGM-CSF at a final concentration of 1 ng/ml are added into each well. After a 24 hour incubation, the cells are harvested on glass fiber filters. Filters are washed, dried, and counted according to standard methods. Cells cultured with media alone serve as the control. All assays are performed in triplicate. Two additional murine cell lines EL4, a T cell leukemia/lymphoma and the myeloid leukemia C1498 (American Type Culture Collection, Rockville, N.Mex.) are used which did not respond to mGM-CSF.

Radiolabeling of fusion toxins

Relatively efficient radiolabeling of proteins (e.g., monoclonal antibodies) with $^{111}$In and $^{90}$Y has been reported through both acyclic (DTPA) and cyclic (DOTA) bifunctional chelating agents (85, 314). Due to the better stability of yttrium-DOTA complexes as compared to those of DTPA, the former is used for the $^{90}$Y-labelings. The macrocyclic chelating agent DOTA is prepared according to a procedure reported by Renn and Meares (314) which results in the production of a nitrophenyl derivative of this compound. The nitro derivative is reduced to the corresponding amine by catalytic hydrogenation and derivatized to the N-(2-bromoacetyl) derivative. The latter step is done by a dicyclohexyl carbodiimide (DCC)/1-hydroxybenzotriazole (HOBT) reaction between the amino-DOTA and 2-bromoacetic acid. The resulting compound is conjugated to fusion toxins according to a procedure reported by McCall et al. (359). In this procedure the protein, the DOTA derivative and Traut's reagent, 2-iminothiolane (2-IT), are mixed in phosphate buffer (pH 8–8.5) in a 1:10:20 (protein:2-IT:DOTA) ratio and incubated at 37° C. for 30 minutes. The conjugate is separated and purified by chromatography.

The radiolabeling of the DOTA conjugates with $^{90}$Y (in chloride form from the DOE Hanford Facility) are carried out. Briefly, the solution of the radiometal (supplied as the metal chlorides in 0.1M or 0.05M HCl solutions) will be added to 0.1M acetate buffer (pH 6), stirred for 10 minutes, and the resulting solution is mixed with the solution of the conjugate in the acetate buffer and incubated at 37° C. for 1 h or until maximum labeling efficiency is reached, as evidenced by radio-HPLC or ITLC analyses.

For radiolabeling with $^{186}$Re or $^{188}$Re, the trihydroxamic acid derivative, trisuccin is used as the chelating agent. Trisuccin is an efficient chelating agent for $^{186}$Re and $^{188}$Re. The conjugation of this compound to the fusion toxin is carried out through the procedure described previously (49) Briefly, the active ester of trisuccin with tetrafluorophenol (TFP-OH) is generated in dimethyl sulfoxide (DMSO) using DCC. This active ester is then added to the solution of the fusion toxin in carbonate buffer at pH 8.5 and the mixture is incubated from 0° C. to room temperature for 2 h. The conjugate is then purified by HPLC chromatography. The benzyl protecting groups of the hydroxamate functions are removed by catalytic hydrogenation prior to radiolabeling.

Rhenium-186 is supplied by the University of Missouri : Research Reactor (MURR), in the form of aluminum [$^{186}$Re]-perrhenate with high specific activities. A labeling study of trisuccin with this isotope using the MURR's preparation was carried out with high labeling yields. The perrhenate is reduced by stannous chloride in the presence of citric acid and the pH is adjusted to pH 7. The solution of the radioisotope is then mixed with the conjugate at about the same pH and incubated at 40° C.

The TETA-$DT_{390}$-mGM-CSF and TETA-$DT_{390}$-mIL-4 conjugates are labeled with $^{64/67}$Cu according to the following method. $^{64/67}CuCl_2$ in 0.1 M HCl is converted to $^{64/67}$Cu-acetate by diluting with a 10-fold excess of 0.1 M $NH_4OAc$ at pH 5.5. This is added to TETA-peptide (1–10 mg) containing gentisic acid to reduce radiolysis. The mixture is incubated at room temperature for 1 h and then purified if necessary using the method of Anderson et al., *J Nucl Med.* 1995; 36:2315–2325.

The following procedures are used for labeling with $^{212}$Bi or $^{212}$Pb. Bismuth is generated and chelated as previously described (93,98,102,103,106). $^{212}$Bi is eluted in dilute HI. The solution is neutralized to pH 4 with acetate. The solution is combined with the chelate conjugate, mixed and allowed to react at 37° C. until the chelation is complete for 15–30 minutes. At the end of this period, the mixture is purified. Lead is generated and chelated as previously described (98,109,340). $^{212}$Pb is eluted from the generator in HCl. The HCl will be taken to dryness twice with $HNO_3$ and re-dissolved in 1 mM $HNO_3$. The solution is added to the chelate conjugate and immediately adjusted to pH 9 with base. The mixture is brought to 50° C. and allowed to react for 5–30 minutes. Care is taken to insure that the conjugate is not affected by changes in temperature or pH outlined in these procedures. The mixture is purified by the procedure outlined below.

Radioiodination of native fusion toxins

The fusion toxins are radioiodinated by standard techniques through their tyrosine residues. GM-CSF-DT or IL-4-DT is labeled with $^{125}$I or $^{131}$I using the Iodogen method (316). Briefly, 100 μg (or 1 mg for therapy studies) of fusion toxin are incubated with 100 μCi (or 1 mCi) of $^{125}$I or $^{131}$I in 100 μl (or 1 ml) of 200 mM phosphate buffer, pH 8.1, for minutes at room temperature. Iodogen-coated tubes (10 μg or 100 μg/tube) are prepared by evaporating the chloroform solution of Iodogen by nitrogen gas.

Purification of radiolabeled fusion toxins.

Excess radionuclide is removed from the radiolabeled fusion toxins by Sephadex G-25 gel filtration. The radiolabeled fusion toxins are tested by size-exclusion (SE) HPLC on a TSK S-2000 column to determine the percentage of radioactivity associated with the fusion toxins. Alternatively, the various RFT are electrophoresed on 4–12% polyacrylamide gels according to the Laemmli method (317). These gels are autoradiographed to visualize the labeled RFT and verify the efficiency of transblotting. The transblotting method follows the Towbin et al. methodology (318) using 25 mM Tris, 192 mM glycine pH 8.3 and 20% v/v methanol onto nitrocellulose membranes. The membranes are stained and then applied to x-ray film with a plastic barrier for autoradiography.

Binding of radiolabeled fusion toxin to transduced cells

The binding activity of radiolabeled fusion toxins are measured by determining the percent absorption of labeled fusion toxin to genetically transduced colon cancer cells, lung cancer cells, mouse myelomonocytic leukemia cells, and non-transduced colon and lung cancer cells as controls, as described elsewhere (81, 195, 319). Briefly, cells are harvested using EDTA/PBS and resuspended in RPMI 1640 medium with 10% FBS and 1% L-glutamine at $2 \times 10^7$ cells/ml. Cells are then aliquoted in duplicate for each fusion toxin being tested at $10 \times 10^6$ cells/tube. Radiolabeled fusion toxins ($10^5$ cpm) are then added and incubated at 4° C. for 1 hour with shaking. The cells are then washed with 4 ml PBS-1% BSA, 0.001 M EDTA and the cell pellet counted in a well-type gamma counter. The % binding is then calculated. In all binding assays, nonspecific binding of radiolabeled fusion toxins will be measured in the presence of a 200-fold or greater molar excess of unlabeled fusion toxin. For equilibrium binding studies, transduced cells will be incubated with various concentrations of radiolabeled fusion toxin for 1 hr at 4° C. and assayed for binding as described above. Data will be corrected for nonspecific binding, and the data plotted for Scatchard analysis (319).

Stability of radiolabeled fusion toxins

The in vitro stabilities of the radiolabeled fusion toxins are evaluated by adding the solution of the radiolabeled fusion toxin (50 μl–100 μl) to phosphate-buffered saline (pH 7.4, 500 μl), mixed at 4° C. and analyzed by SE-HPLC. A 20 μl aliquot is withdrawn at equal time intervals (6 to 24 hours) and screened by SE-HPLC. A second sample is analyzed in the same way only at 37° C. All samples are screened by HPLC and the radioactivity content of the fusion toxins is plotted against time.

To test the in vitro serum stability of the fusion toxins, the labeled fusion toxin solution (50 μl–100 μl) is added to 500 μl of human serum and the mixture is incubated at 37° C. At 6 to 24 hour time intervals, 20 μl aliquots are injected into the HPLC to follow the stability kinetics compared to a standard of the added activity kept at 4° C. Biological activity of the product is assessed with time by protein synthesis inhibition assays. To check for retention of binding activity, the protein fractions are tested by the in vitro cell binding assay.

Protein synthesis inhibition

Protein synthesis inhibition (PSI) assays are used to 1) measure changes in protein synthesis within hours/days of RFT treatment, 2) generate useful information relative to the potency, stability and selectivity of RFT, 3) generate information regarding comparative rates of protein synthesis inactivation relative to each RFT. The PSI assay is carried out as described above. Control studies are carried out with $DT_{390}$-hIL-2, $DT_{390}$-mIL-4, and native DT.

Localization and imaging studies

In order to properly interpret the results of preclinical therapy studies, it is important to test each new RFT preparation for its tumor localizing ability. The degree of localization of the various radiolabeled fusion toxins is quantifed and the level of their persistence within the tumor mass over time is documented using described procedures (81,195,200–202). Mice bearing i.p. transplants of CT-26 or LS174T colon tumor or MEL-1 melanoma are established as described above. Groups of 6 mice receive a single i.p. or i.v. injection of 10 to 100 μCi (10 to 200 μg) of radiolabeled fusion toxin. In selected experiments, dual radionuclide studies are performed in which the test fusion toxin is labeled with one radionuclide and control fusion toxin is labeled with another radionuclide, and they are injected simultaneously and the tissues counted at settings appropriate for the detection of the energies of the different radionuclides. Paired-label studies are essential to factor out differences in tumor size, receptor density and permeability as well as catabolic rate, that often exist among a group of experimental animals. At 2 hours to 5 days after injection, the mice are bled by cardiac puncture, dissected, and the tissues rinsed with saline and counted in a well-type gamma counter to determine the radioactivity in the tumors and normal tissues. A standard of the injectate is also counted. For each radiolabeled fusion toxin, the following parameters are determined using previously published, standard methods:

percent injected dose per organ (%ID/organ) and gram of tissue (% ID/g), tumor to normal tissue ratios and localization index. Representative sections of organs and tissues are fixed in fresh 2% paraformaldehyde, paraffin-embedded and sectioned to provide an estimate, by autoradiography, of the architectural localization of radiolabeled fusion toxin in relation to expressed receptor using previously described procedures (224–226). Histologic sections adjacent to the one used for autoradiography are stained for receptor using the avidin-biotin immunoperoxidase method as described below. For scintigraphic imaging studies, mice with colon tumors are given i.p. or i.v. injections of 100 μCi of $^{131}$I-, $^{186}$Re-, or $^{111}$In-labeled ligand. Mice are anesthetized with Ketamine and Xylazine, and analog and digital images are acquired from the dorsal view with a Sopha DSX rectangular gamma camera equipped with a 4 mm pinhole collimator. Images are acquired for approximately 100,000 5 counts at 2 hours after labeled ligand administration. The time required to reach this level is used at subsequent times. To permit visual assessment of relative tumor specificity, digital images are count normalized using a Sopha 32-bit microcomputer to produce visually identical levels of activity in a large region of interest covering the central torso. Mice are dissected following the images for distribution analysis.

The amount of label which is incorporated into protein is determined by both HPLC analysis and TCA precipitation and counting, to help address the issue of metabolic dehalogenation or loss of radiometal, versus loss of fusion toxin binding activity. It should be noted that fusion toxin metabolism (including dehalogenation or loss of radiometal) may work for, rather than against, tumor localization. The proportion of serum-borne radionuclide associated with protein is determined by precipitation of total protein with an equal volume of 10% w/v TCA (323). The precipitates forming overnight at 4%C are washed three times in 10% TCA before counting. The proportion of radionuclide associated with fusion toxin is determined by precipitation with a rabbit anti-GM-CSF antiserum.

Dosimetry

Tissue and organ doses for the radiolabeled fusion toxins will be computed using the RFT biodistribution data for tumor and normal tissues over time and the energy deposition properties of the radionuclides ($^{131}$I, $^{90}$Y, $^{186}$Re) in a MIRD-type formalism.

In a similar protocol, determination of dose for the $^{212}$p b and/or $^{212}$Bi conjugates utilizes a MIRD-type formalism. The photon and beta emissions by Pb and its daughters enable one to obtain biodistribution data and to perform autoradiography on tissue samples. The MIRD calculations provide first pass estimates of dosimetry. One can utilize the formalism of Stinchcomb and Roeske (360) to better model the dose distribution for a high LET emitter. At worst, the MIRD formalism provides an estimate of dosimetry that can be used to compare results with the low LET emitters and to determine dose response.

Therapy studies and statistical analysis

Therapy studies with $^{131}$I, $^{186}$Re, $^{212}$Bi, or $^{90}$Y-labeled RFT are performed in mice bearing i.p. transplants of colon cancer cell lines. Tumor-bearing mice are randomly divided into groups of 10 mice, housed 5/cage, at the time of treatment. Therapy studies with radiolabeled fusion toxins are performed. Animals are given injections of radiolabeled fusion toxin when the intraperitoneal tumors are established. The animals are injected with a range of doses (0.5, 1, 1.5 etc. mCi) of radiolabeled fusion toxin (50 to 200 µg) in a single injection, to determine whether tumor growth is specifically inhibited and whether regressions occur. The maximal tolerated dose of each fusion toxin are compared. Fractionated RFT studies are performed, by administering different quantities of radiolabeled fusion toxin at varying time intervals. Fractionation studies are conducted with one-half the quantity of radioactivity administered in a single injection (i.e. 0.25, 0.5, 0.75, 1 etc. mCi) given in two or three injections spaced 1, 2, and 3 days between injections to determine the optimal dose and fractionation interval in terms of tumor regression and toxicity. The maximal tolerated dose of each fusion toxin is compared. An untreated control group and groups inoculated with unlabeled fusion toxin or free radionuclide are included. Negative control tumors or tumors injected with control genetic constructs are tested using the most effective dose of radiolabeled fusion toxin. Animals with i.p. tumors are randomized into groups according to similar distributions of tumor sizes. A test group consists of 10 mice. Survival is estimated to be the day the animal is killed.

A recombinant replication-incompetent adenoviral vector encoding the human epidermal growth factor receptor gene (AdCMVhEGFr) was constructed and showed it induces the expression of human epidermal growth factor receptor (hEGFr) in PC-3 and LNCaP human prostate cancer cells. Expression of hEGFr was evaluated using [$^{125}$I]-hEGF in a live cell binding assay using uninfected cells or with cells that were infected at a MOI of 10 or 100 pfu/cell. Uninfected PC-3 and LNCaP cells showed 16.4±2.8% and 10.5±8.4% binding of [I-125]-hEGF respectively. Infection of PC-3 and LNCaP cells with 10 pfu/cell of AdCMVhEGFr resulted in 25.3±3.3% and 47.1±1.0% binding of [I-125]-hEGF, while an MOI of 100 resulted in 48.3±2.7% and 45.0±1.7% binding. he relative degree of internalization of [I-125]-hEGF was investigated in normal and adenoviral vector infected LNCaP cells. [I-125]-hEGF had a higher level of radioactivity retained intracellularly after 2 hours in infected cells than in normal cells (42.2±3.6% vs. 26.6±3.3% respectively). Also, the amount of radioactivity released into the supernatant was greater in normal cells than in infected cells (70.2±3.7% vs. 45.4±1.0% at 4 hours respectively). These results demonstrate a higher level of radioligand internalization and retention in genetically transduced cells, and suggest that genetic induction of receptors in tumors will result in greater therapeutic efficacy with unlabeled or radiolabeled fusion toxins such as DT-hEGF as a result of higher tumor cell binding, internalization and hence retention. Since [I-125]-hEGF has been produced, one would be able to radiolabel the DT-hEGF fusion toxin also.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

SEQUENCE LISTING

```
<160> NUMBER OF SEQ ID NOS: 10

<210> SEQ ID NO 1
<211> LENGTH: 21
<212> TYPE: PRT
<213> ORGANISM: artificial sequence
<220> FEATURE:
<223> OTHER INFORMATION: Amino acid sequence encoded by DNA linking
                        mGM-CSF to DT after restriction endonuclease
                        digestion of pDT-GM-CSF.

<400> SEQUENCE: 1

Gly Gly Gly Gly Ser Gly Gly Gly Gly Ser Gly Ala Gly Gly Ser
                5                   10                  15
Gly Gly Gly Gly Ser Phe
                20

<210> SEQ ID NO 2
<211> LENGTH: 33
<212> TYPE: DNA
<213> ORGANISM: artificial sequence
<220> FEATURE:
<221> NAME/KEY: primer
```

```
<223> OTHER INFORMATION: Primer used to generate DT390-mIL-4 fusion
                         protein

<400> SEQUENCE: 2
agatatacca tgggcgctga tgatgttgtt gat                                    33

<210> SEQ ID NO 3
<211> LENGTH: 36
<212> TYPE: DNA
<213> ORGANISM: artificial sequence
<220> FEATURE:
<221> NAME/KEY: primer
<223> OTHER INFORMATION: Primer used to generate DT390-mIL-4 fusion
                         protein

<400> SEQUENCE: 3
gtcgcatccg tggatatgaa atggttgcgt tttatg                                 36

<210> SEQ ID NO 4
<211> LENGTH: 36
<212> TYPE: DNA
<213> ORGANISM: artificial sequence
<220> FEATURE:
<221> NAME/KEY: primer
<223> OTHER INFORMATION: Primer used to generate DT390-mIL-4 fusion
                         protein

<400> SEQUENCE: 4
cataaaacgc aaccatttca tatccacgga tgcgac                                 36

<210> SEQ ID NO 5
<211> LENGTH: 27
<212> TYPE: DNA
<213> ORGANISM: artificial sequence
<220> FEATURE:
<221> NAME/KEY: primer
<223> OTHER INFORMATION: Primer used to generate DT390-mIL-4 fusion
                         protein

<400> SEQUENCE: 5
gccgtactcg agcgagtaat ccatttg                                           27

<210> SEQ ID NO 6
<211> LENGTH: 20
<212> TYPE: PRT
<213> ORGANISM: artificial sequence
<220> FEATURE:
<223> OTHER INFORMATION: Amino acid sequence encoded by DNA linking
                         mGM-CSF to DT.

<400> SEQUENCE: 6

Ser Gly Gly Gly Gly Ser Gly Gly Gly Gly Ser Gly Gly Gly Gly
                5                   10                  15
Ser Gly Gly Gly Gly
                20

<210> SEQ ID NO 7
<211> LENGTH: 30
<212> TYPE: DNA
<213> ORGANISM: artificial sequence
<220> FEATURE:
<221> NAME/KEY: primer
<223> OTHER INFORMATION: Sense primer used to introduce an Nco I site
                         with an initiation codon ATG and initial five
                         codons of DT

<400> SEQUENCE: 7
agatatacca tgggcgctga tgttgttgat                                        30
```

-continued

```
<210> SEQ ID NO 8
<211> LENGTH: 78
<212> TYPE: DNA
<213> ORGANISM: artificial sequence
<220> FEATURE:
<221> NAME/KEY: primer
<223> OTHER INFORMATION: Anti-sense primer used to introduce the codons
      386 to 389 of DT and codons of linker

<400> SEQUENCE: 8
cgacccacca ccgcccgagc caccgccacc gcttccaccg cctccagatc cgccgccacc     60
aaatggttgc gttttatg                                                   78

<210> SEQ ID NO 9
<211> LENGTH: 36
<212> TYPE: DNA
<213> ORGANISM: artificial sequence
<220> FEATURE:
<221> NAME/KEY: primer
<223> OTHER INFORMATION: Sense primer used to introduce the codons 26
                         to 31 of GM-CSF and codons of part of the
                         linker

<400> SEQUENCE: 9
tcgggcggtg gtgggtcggt cacccggcct tggaag                               36

<210> SEQ ID NO 10
<211> LENGTH: 33
<212> TYPE: DNA
<213> ORGANISM: artificial sequence
<220> FEATURE:
<221> NAME/KEY: primer
<223> OTHER INFORMATION: Antisense primer used to introduce an Xho I
                         site and the last 7 codons of GM-CSF

<400> SEQUENCE: 10
cgtgcgctcg agtttttggc ttggtttttt gca                                  33
```

What is claimed is:

1. A composition of matter, comprising a recombinant fusion toxin comprising:

a toxin fused to a targeting moiety which binds to a receptor overexpressed by tumor cells, wherein said toxin-targeting fusion moiety is labeled with a radionuclide.

2. The composition of claim 1, wherein said toxin is selected from the group consisting of diphtheria toxin, ricin, gelonin and pseudomonas exotoxin.

3. The composition of claim 1, wherein said radionuclide is selected from the group consisting of $^{90}Y$, $^{186}Re$, $^{188}Re$, $^{64}Cu$, $^{67}Cu$, $^{212}Pb$, $^{212}Bi$, $^{123}I$, $^{211}At$, $^{213}Bi$ and $^{131}I$.

4. The composition of claim 1, wherein said targeting moiety that binds to receptors overexpressed by tumor cells is selected from the group consisting of the interleukin-4, interleukin-2, epidermal growth factor and the granulocyte macrophage colony stimulating factor.

5. The composition of claim 1, wherein said tumor cell is selected from the group consisting of an acute myeloid leukemia cell, a melanoma cell, a small-cell carcinoma of the lung cell, a breast cancer cell, a renal carcinoma cell, a glioma cell, a gastric carcinoma cell, an ovarian carcinoma cell, a prostate cancer cell and a colon cancer cell.

6. The composition of claim 1, wherein said recombinant fusion toxin is $DT_{390}$-mGM-CSF.

7. The composition of claim 1, wherein said recombinant fusion toxin is $DT_{390}$-mIL-4.

8. A pharmaceutical composition, comprising the composition of claim 1.

9. A method of killing a tumor cell, comprising the step of contacting said cell with the composition of claim 1.

10. The method of claim 9, wherein said cell is selected from the group consisting of an acute myeloid leukemia cell, a melanoma cell, a small-cell carcinoma of the lung cell, a breast cancer cell, a renal carcinoma cell, a glioma, a gastric carcinoma cell, an ovarian carcinoma cell, and a colon cancer cell.

11. A method of treating a tumor cell in an individual in need of said treatment, comprising the step of administering to said patient an effective dose of the composition of claim 8.

* * * * *